(12) United States Patent
Loewke et al.

(10) Patent No.: US 11,735,302 B2
(45) Date of Patent: Aug. 22, 2023

(54) MACHINE LEARNING FOR OPTIMIZING OVARIAN STIMULATION

(71) Applicant: Alife Health Inc., Cambridge, MA (US)

(72) Inventors: Kevin Loewke, Menlo Park, CA (US); Paxton Maeder-York, Cambridge, MA (US); Melissa Teran, San Francisco, CA (US); Mark Lown, Castro Valley, CA (US); Arielle Sarah Rothman, Woodmere, NY (US); Veronica Isabella Nutting, Wheeling, WV (US); Michael Fanton, Chicago, IL (US); Jordan Tang, San Francisco, CA (US)

(73) Assignee: Alife Health Inc., Cambridge, MA (US)

( * ) Notice: Subject to any disclaimer, the term of this patent is extended or adjusted under 35 U.S.C. 154(b) by 0 days.

(21) Appl. No.: 17/707,369

(22) Filed: Mar. 29, 2022

(65) Prior Publication Data

US 2022/0399091 A1 Dec. 15, 2022

Related U.S. Application Data

(60) Provisional application No. 63/256,343, filed on Oct. 15, 2021, provisional application No. 63/209,327, filed on Jun. 10, 2021.

(51) Int. Cl.
*G16H 20/10* (2018.01)
*G16H 50/70* (2018.01)
*G16H 50/30* (2018.01)

(52) U.S. Cl.
CPC ............ *G16H 20/10* (2018.01); *G16H 50/30* (2018.01); *G16H 50/70* (2018.01)

(58) Field of Classification Search
None
See application file for complete search history.

(56) References Cited

U.S. PATENT DOCUMENTS 6,660,531 B2  12/2003  Stewart et al.
7,643,969 B2   1/2010  Soto et al.
(Continued)

FOREIGN PATENT DOCUMENTS

CN  112101657 A  * 12/2020
EP   1 960 929 A1    8/2008
(Continued)

OTHER PUBLICATIONS

US 10,339,267 B2, 07/2019, Elashoff et al. (withdrawn)
(Continued)

*Primary Examiner* — Shahid Merchant
*Assistant Examiner* — Karen A Hranek
(74) *Attorney, Agent, or Firm* — Cooley LLP

(57) ABSTRACT

Systems and methods for implementing machine-learning models for ovarian stimulation is described herein. In some variations, a computer-implemented method may include optimizing an ovarian stimulation process may include receiving patient-specific data associated with a patient, and predicting an egg outcome for the patient for each of a plurality of treatment options for an ovarian stimulation process based on at least one predictive model and the patient-specific data, where the at least one predictive model is trained using prior patient-specific data associated with a plurality of prior patients.

30 Claims, 34 Drawing Sheets

(56) References Cited

U.S. PATENT DOCUMENTS

| | | | |
|---|---|---|---|
| 8,285,525 | B2 | 10/2012 | Soto et al. |
| 8,560,281 | B2 | 10/2013 | Soto et al. |
| 8,744,815 | B2 | 6/2014 | Soto et al. |
| 9,177,098 | B2 | 11/2015 | Elashoff et al. |
| 9,348,972 | B2 | 5/2016 | Yao |
| 9,458,495 | B2 | 10/2016 | Yao et al. |
| 9,690,907 | B2 | 6/2017 | Soto et al. |
| 9,961,304 | B2 | 5/2018 | Kim et al. |
| 10,127,664 | B2 | 11/2018 | Govindjee et al. |
| 10,162,800 | B2 | 12/2018 | Elashoff et al. |
| 10,426,442 | B1 | 10/2019 | Schnorr |
| 10,438,686 | B2 | 10/2019 | Yao et al. |
| 10,467,382 | B2 | 11/2019 | Karchmer et al. |
| 10,515,188 | B2 | 12/2019 | Soto et al. |
| 10,552,576 | B2 | 2/2020 | Campbell |
| 10,580,516 | B2 | 3/2020 | Eiashoff et al. |
| 10,646,156 | B1 | 5/2020 | Schnorr |
| 2003/0149597 | A1 | 8/2003 | Zaieski |
| 2004/0243614 | A1* | 12/2004 | Boone ............ G16Z 99/00 707/999.102 |
| 2005/0071087 | A1 | 3/2005 | Anderson |
| 2006/0173663 | A1* | 8/2006 | Langheier ............ G16H 50/20 703/11 |
| 2010/0036192 | A1 | 2/2010 | Yao et al. |
| 2010/0312798 | A1* | 12/2010 | Dutta ............ G16H 50/70 707/E17.014 |
| 2011/0251834 | A1 | 10/2011 | Fearon et al. |
| 2011/0313790 | A1* | 12/2011 | Yao ............ G16H 50/50 705/2 |
| 2014/0107934 | A1* | 4/2014 | Elashoff ............ G16H 10/20 702/19 |
| 2015/0018664 | A1* | 1/2015 | Pereira ............ G16H 50/20 600/410 |
| 2015/0161327 | A1 | 6/2015 | Anderson |
| 2015/0353886 | A1* | 12/2015 | Alper ............ G01N 33/743 514/9.9 |
| 2016/0278688 | A1 | 9/2016 | Pierzynski et al. |
| 2017/0089820 | A1 | 3/2017 | Wong et al. |
| 2017/0107573 | A1 | 4/2017 | Beim |
| 2017/0262580 | A1 | 9/2017 | Beim et al. |
| 2018/0108431 | A1* | 4/2018 | Beim ............ G16H 50/70 |
| 2018/0114600 | A1 | 4/2018 | Roberts et al. |
| 2018/0144471 | A1 | 5/2018 | Govindjee et al. |
| 2018/0199815 | A1 | 7/2018 | Redei |
| 2018/0286508 | A1* | 10/2018 | Leontovich ........ G01N 33/6869 |
| 2019/0080800 | A1 | 3/2019 | Beim |
| 2019/0103175 | A1* | 4/2019 | Yurttas Beim ......... G16H 10/60 |
| 2019/0233898 | A1 | 8/2019 | Newman et al. |
| 2019/0252043 | A1 | 8/2019 | Elashoff et al. |
| 2019/0307417 | A1* | 10/2019 | Subbarao ............ A61B 8/483 |
| 2019/0374193 | A1 | 12/2019 | Ramachandran et al. |
| 2020/0011883 | A1* | 1/2020 | Beim ............ G01N 33/689 |
| 2020/0126233 | A1 | 4/2020 | Shinoda et al. |
| 2020/0129139 | A1 | 4/2020 | Faghih et al. |
| 2020/0227167 | A1 | 7/2020 | Soto et al. |
| 2020/0245968 | A1 | 8/2020 | Nellur Prakash et al. |
| 2020/0279635 | A1* | 9/2020 | Letterie ............ G16H 50/50 |
| 2020/0340059 | A1 | 10/2020 | Beim |
| 2020/0349709 | A1 | 11/2020 | Iwata et al. |
| 2020/0395117 | A1* | 12/2020 | Schnorr ............ G06N 3/088 |
| 2021/0366577 | A1* | 11/2021 | Koller ............ G16B 40/20 |
| 2022/0044822 | A1* | 2/2022 | Li ............ G01N 33/689 |

FOREIGN PATENT DOCUMENTS

| | | |
|---|---|---|
| EP | 2 440 141 A1 | 4/2012 |
| EP | 3 169 811 A1 | 5/2017 |
| EP | 3 363 368 A1 | 8/2018 |
| EP | 3 408 796 A1 | 12/2018 |
| EP | 3 482 328 A1 | 5/2019 |
| EP | 3 701 415 A1 | 9/2020 |
| EP | 3 751 513 A1 | 12/2020 |
| JP | 2010-502338 A | 1/2010 |
| WO | WO-2013/074058 A1 | 5/2013 |
| WO | WO-2013/095878 A1 | 6/2013 |
| WO | WO-2014/062393 A1 | 4/2014 |
| WO | WO-2015/044751 A | 4/2015 |
| WO | WO-2016/149759 A1 | 9/2016 |
| WO | WO-2017/019788 A1 | 2/2017 |
| WO | WO-2018/080120 A1 | 5/2018 |
| WO | WO-2018/222006 A1 | 12/2018 |
| WO | WO-2019/060882 A1 | 3/2019 |
| WO | WO-2019/233308 A1 | 12/2019 |
| WO | WO-2020/118790 A1 | 6/2020 |
| WO | WO-2020/251714 A1 | 12/2020 |

OTHER PUBLICATIONS

Tronci et al., Patient-Specifi Models from Inter-Patient Biological Models and Clinical Records, 2014, Formal Methods in Computer-Aided Design (Year: 2014).*

Qui et al., Personalized prediction of live birth prior to the first in vitro fertilization treatment: a machine learning method, 2019, Journal of Translational Medicine (Year: 2019).*

Letterie et al., Artificial intelligence in in vitro fertilization: a computer decision suport system for day-to-day management of ovarian stimulation during in vitro fertilization, Oct. 2020, Fertility and Sterility, vol. 114, No. 5 (Year: 2020).*

Wang et al., A Knowledge-Based Decision Support System for In Vitro Fertilization Treatment, 2020, IEEE International Conference on E-health Networking, Application & Services (HEALTHCOM) (Year: 2020).*

Davar et al., The effect of 24 hours delay in oocyte maturation triggering in IVF/ICSI cycles with antagonist protocol and not-elevated progesterone: A randomized control trial, Jul. 2017, Int J Reprod BioMed, vol. 15 No. 7 (Year: 2017).*

Rustamov et al., How much variation in oocyte yield after controlled ovarian stimulation can be explained? A multilevel modelling study, 2017, Human Reproduction Open (Year: 2017).*

Abbara et al., Follicle Size on Day of Trigger Most Likely to Yield a Mature Oocyte, Apr. 25, 2018, Frontiers in Endocrinology (Year: 2018).*

Arce, J.C. et al., (2014). "Ovarian response to recombinant human follicle-stimulating hormone: a randomized, antimullerian hormone-stratified, dose-response trial in women undergoing in vitro fertilization/ intracytoplasmic sperm injection," Fertil. Steril. 102:1633-1640.

Fanton, M. et al. (2022). "An interpretable machine learning model for predicting the optimal day of trigger during ovarian stimulation," Fertil. Steril. 118:101-108.

Fanton, M. et al. (2022). "An interpretable machine learning model for individualized gonadotropin starting dose selection during ovarian stimulation," RBMO, 19 total pages.

Hariton, E. et al. (2017). "Total number of oocytes and zygotes are predictive of live birth pregnancy in fresh donor oocyte in vitro fertilization cycles," Fertil. Steril. 108:262-268.

Hariton, E. et al., (2021). "A machine learning algorithm can optimize the day of trigger to improve in vitro fertilization outcomes," Fertil. Steril. 116:1227-1235.

International Search Report dated Jul. 8, 2022, for PCT Application No. PCT/US2022/022373, filed on Mar. 29, 2022, 2 pages.

Letterie, G. et al. (2020). "Artificial intelligence in in vitro fertilization: a computer decision support system for day-to-day management of ovarian stimulation during in vitro fertilization," Fertil. Steril. 114:1026-1031.

Polyyzos, N.P. et al. (2018). "Cumulative live birth rates according to the number of oocytes retrieved after the first ovarian stimulation for in vitro fertilization/intracytoplasmic sperm injection: a multi-center multinational analysis including ~15,000 women," Fertil Steril. 110:661-670.

Sunkara, S.K. et al. (2011). "Association between the number of eggs and live birth in IVF treatment: an analysis of 400 135 treatment cycles," Hum. Reprod. 26:1768-1774.

Wang, R. et al. (2019), "Artificial intelligence in reproductive medicine," Reproduction 158:R139-R154.

Written Opinion of the International Searching Authority dated Jul. 8, 2022, for PCT Application No. PCT/US2022/022373, filed on Mar. 29, 2022, 8 pages.

* cited by examiner

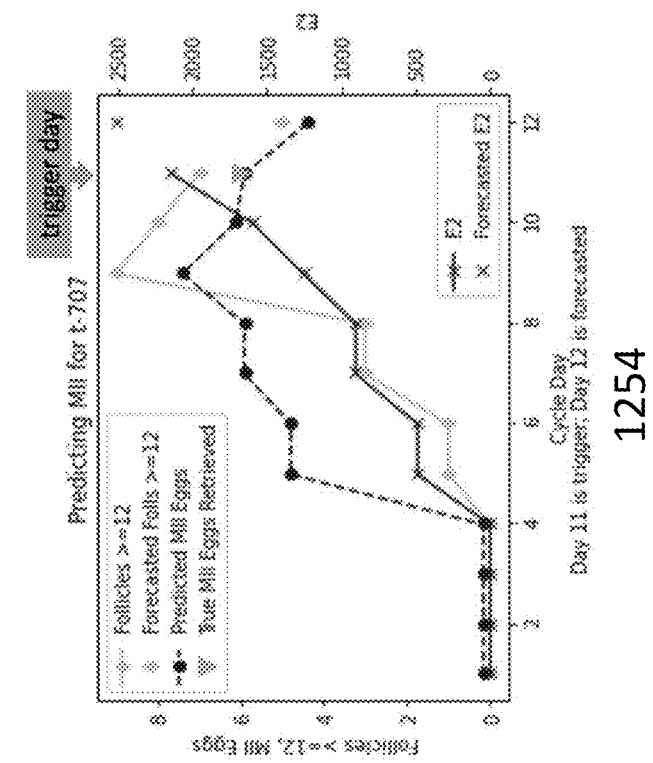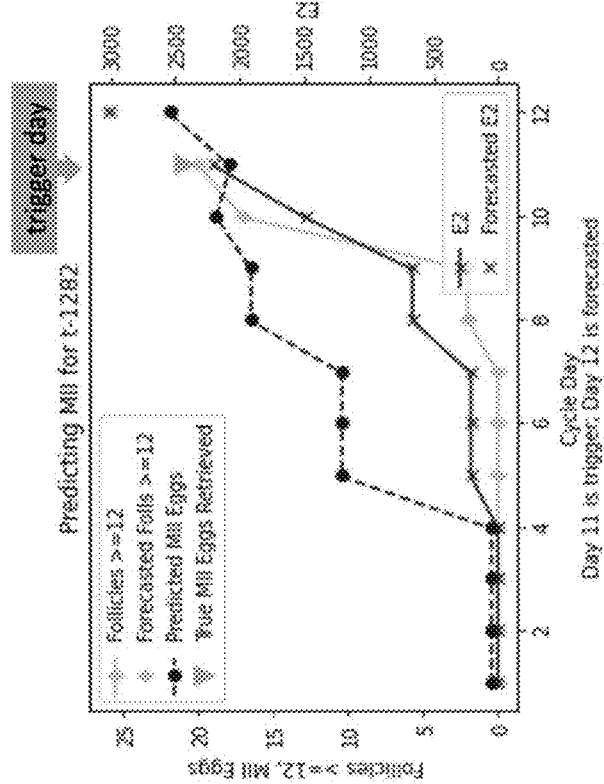
FIG. 12B

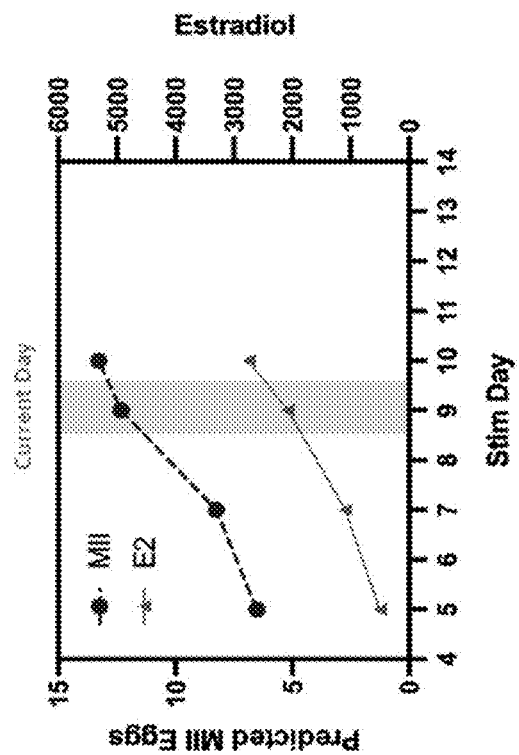
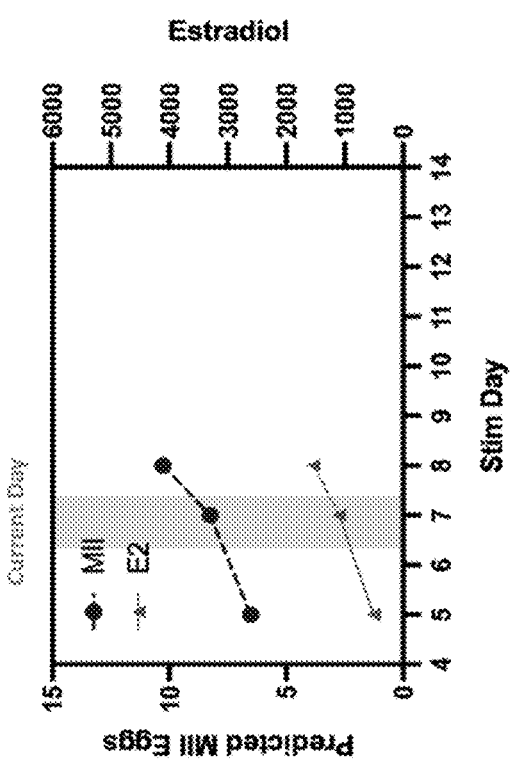
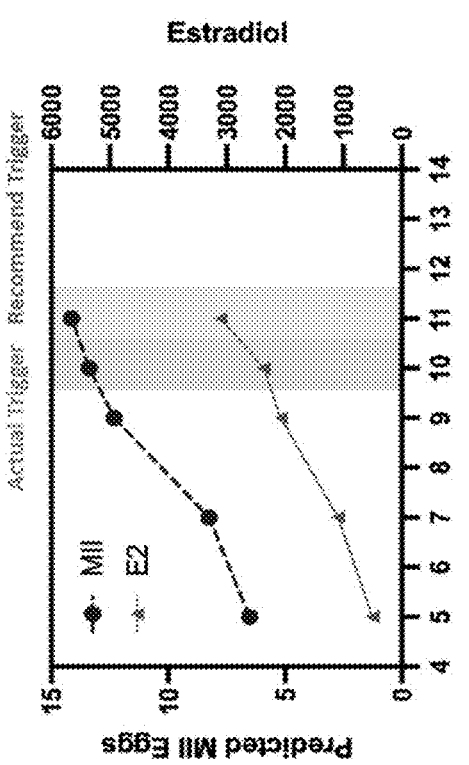
FIG. 17A
FIG. 17B
FIG. 17C

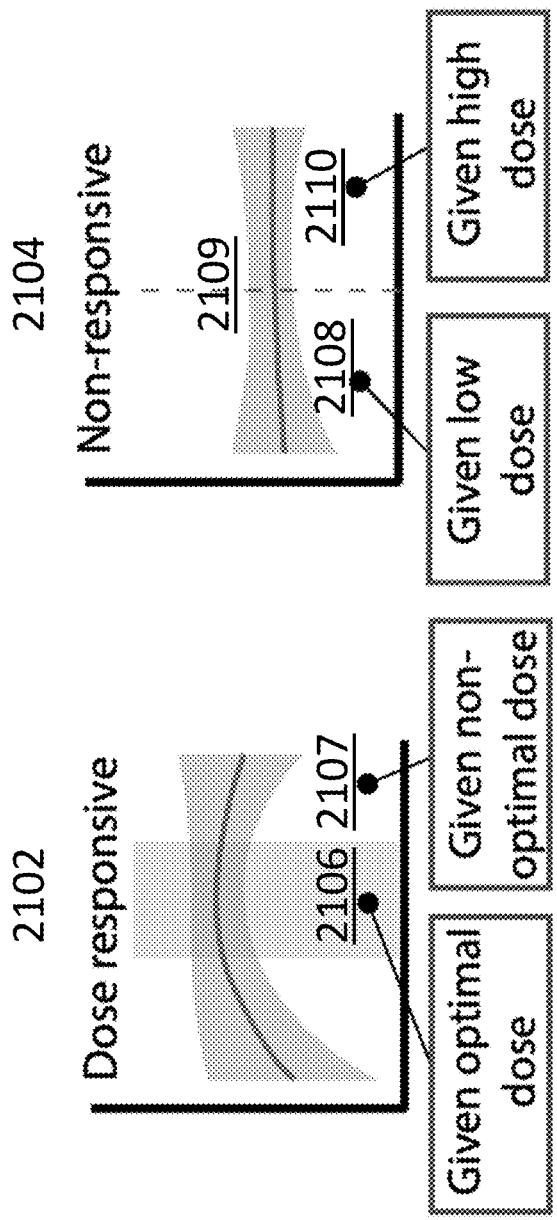

MACHINE LEARNING FOR OPTIMIZING OVARIAN STIMULATION

CROSS-REFERENCE TO RELATED APPLICATIONS

This application claims priority to and benefit of U.S. Provisional Application No. 63/256,343 filed Oct. 15, 2021 and U.S. Provisional Application No. 63/209,327 filed Jun. 10, 2021, the disclosure of each of which is incorporated herein by reference in its entirety.

TECHNICAL FIELD

This invention relates generally to the field of optimizing ovarian stimulation.

BACKGROUND

In vitro fertilization (IVF), a widely known assisted reproductive technology, involves several complex steps such as ovarian stimulation, egg/oocyte retrieval, fertilization, embryo development, and embryo transfer. Each step of the IVF treatment can play an important role towards the successful development and transfer of an embryo, thereby leading to a successful pregnancy and a potential live birth. For instance, harvesting as many mature eggs as possible during the ovarian stimulation stage may maximize the probability of fertilization and consequently the probability of embryo development and transfer that may ultimately lead to a live birth. Accordingly, in order to obtain viable embryos for transfer that may lead to a successful pregnancy, the number of mature eggs may need to be optimized (e.g., eggs may need to be maximized or otherwise eggs may need to reach an ideal, suitable, desirable, or/or the like outcome) at the ovarian stimulation stage.

In order to optimize the number of mature eggs, generally, a reproductive endocrinologist (RE) may prescribe a stimulation protocol to a patient including follicle stimulating hormone (FSH) and/or luteinizing hormone (LH). Stimulating with FSH and LH may promote multi-follicular growth. This in turn may maximize the number of mature eggs that can be harvested from the patient. The RE may assess the patient and based on the RE's experience, may prescribe a stimulation protocol for the patient. Through the ovarian stimulation phase, the RE may monitor the patient's response and may modify, lengthen, shorten, and/or cancel the stimulation protocol according to the patient's response. Therefore, prescribing a stimulation protocol or modifying and/or canceling the stimulation protocol may be subjective based on the RE's assessment and experience. It may be possible that two REs may prescribe different stimulation protocols for the same patient based on their individual experiences.

More recently, some existing methods use models generated from some data of previous patients to help REs make clinical decisions. For example, some existing methods use models that may output a protocol to be selected for a specific patient, an amount of dosage of medication to be prescribed to a specific patient, suggestions to modify a protocol that has been prescribed to a specific patient, or a day to end the ovarian stimulation phase. More specifically, these methods may predict clinical decisions that the REs may make to maximize the number of mature eggs. Such existing methods may have several drawbacks. For example, a model that is trained to predict clinical decisions may be optimizing for a decision that is most common, but is not necessarily the right decision to yield the optimum number of mature eggs.

Accordingly, there is an unmet need for new and improved methods to standardize the process of ovarian stimulation while optimizing the number of mature eggs for a patient.

SUMMARY

Generally, a computer-implemented method for optimizing ovarian stimulation may include receiving patient-specific data associated with a patient and predicting an egg outcome for the patient for each of a plurality of treatment options. The prediction may be based on at least one predictive model trained using prior patient-specific data associated with a plurality of prior patients. The method may further include providing the predicted egg outcomes to a medical professional for selecting among the plurality of treatment options. The predicted egg outcome may provide useful information regarding characteristics of an egg-related result of the treatment option in relation to ovarian stimulation, such as number of eggs retrieved, number of mature eggs, maturity yield, number of post-mature eggs, number of fertilized eggs, number of embryos, number of blastocysts, number of usable blastocysts, number of euploid blastocysts, fetal heartbeat (e.g., resulting from an egg), and/or live birth rate (e.g., resulting from an egg).

The one or more predictive models used to predict egg outcome may receive as input various kinds of patient-specific data and may be trained on such patient-specific data associated with prior patients. For example, suitable patient-specific data may include age, body mass index, ethnicity, diagnosis of infertility, prior pregnancy history, prior birth history, information relating to one or more prior IVF treatments (e.g., data retrieved during ovarian stimulation, number of eggs retrieved, number of mature eggs, number of successfully fertilized eggs, number of blastocysts, number of usable blastocysts, pregnancy outcome, and live birth outcome, etc.) and/or tone or more treatment variables (e.g., type of medication, a type of hormonal trigger injection to cause follicle maturation, and number of cycle(s) associated with the patient, etc.).

Various predictive models may be configured to predict egg outcome associated for various kinds of treatment options. For example, in some variations, the at least one predictive model may be configured to provide the predicted egg outcome associated with each of a plurality of candidate doses of one or more ovarian stimulation medications (e.g., FSH, LH, etc.) administered to the patient. In at least these variations, the patient-specific data may include one or more baseline measurements selected from the group consisting of: measurements of estradiol (E2), measurements of luteinizing hormone (LH), measurements of progesterone (P4), measurements of follicle stimulating hormone (FSH), measurements of anti-mullerian hormone (AMH), and measurements of antral follicle count (AFC). In some variations, the at least one predictive model may be configured to provide the predicted egg outcome associated with each of a first dose of ovarian stimulation medication and a second dose of ovarian stimulation medication higher than the first dose (e.g., a low dose and a high dose, respectively. Additionally or alternatively, in some variations, the at least one predictive model may be configured to provide the predicted egg outcome associated with each of a first dose ratio of multiple ovarian stimulation medications and a second dose ratio of multiple ovarian stimulation medications, wherein the first dose ratio is different than the second dose ratio. For example, the at least one predictive model may be used to predict egg outcome associated with a first FSH/LH dose ratio, and egg outcome associated with a second FSH/LH different from the first LSH/LH dose ratio.

In some variations, in predicting egg outcome associated with different candidate ovarian stimulation medication doses, the method may include identifying a set of prior patients similar to the patient based on the patient-specific data via a similarity matching technique (e.g., incorporating a KNN model), where the at least one predictive model may include a predictive dose response curve generated based on the prior patient-specific data associated with the prior patients. The dose response curve may predict the egg outcome varying with dose of one or more ovarian stimulation medications administered to the patient. In some variations, the method may further include classifying the patient as one of: (i) a dose-responsive patient having predicted egg outcomes that substantially vary with the dose of one or more ovarian stimulation medications administered to the patient, and (ii) a dose non-responsive patient having predicted egg outcomes that do not substantially vary with dose of one or more ovarian stimulation medications administered to the patient, wherein the classification is based at least in part on a shape of the dose response curve. In some variations, when the patient is classified as a dose-responsive patient, recommending an optimal dose of the one or more ovarian stimulation medications to be administered to the patient, based on a point of the dose response curve associated with a predicted maximum egg outcome. Additionally or alternatively, the method may include displaying the predictive dose responsive curve on a display, such as to aid a medical professional in selecting among the candidate doses of ovarian stimulation medication(s). In some variations, the method may further include displaying a confidence interval around the dose response curve, and/or displaying a cost estimate for administering different doses of one or more ovarian stimulation medications in accordance with the dose response curve.

As another example, in some variations, the at least one predictive model may additionally or alternatively include a first predictive model and a second predictive model for use evaluating candidate hormonal trigger days (e.g., day on which a hormonal trigger injection is administered to the patient to cause follicle maturation in the patient). In these variations, the method may include predicting, via the first predictive model, a first egg outcome resulting from administering a hormonal trigger injection on a first candidate hormonal trigger day, and predicting, via the second predictive model, a second egg outcome resulting from administering the hormonal trigger injection on a second candidate hormonal trigger day. The first and/or second egg outcomes may be displayed on a display, such as to aid a medical professional in selecting among the candidate hormonal trigger days.

For example, the first day may be a current day (day on which the first predictive model is run) and the second day may be a future day (e.g., the day after the current day, or two days after the current day). In these variations, the patient-specific data may include, for example, current day follicle size(s) and/or other follicle metric(s), current day estradiol (E2) level for the patient, and/or current day progesterone (P4) for the patient. The predicted egg outcome may, for example, include number of eggs retrieved, number of mature eggs, number of fertilized eggs, and/or number of usable blastocysts. The first predictive model and/or the second predictive model may include, for example, a recurrent neural network or a linear regression model. The recurrent neural network may, for example, be configured to forecast E2 level and/or forecast follicle metric(s) for the patient at a future date. The linear regression model may, for example, be configured to predict the first and/or second outcome based at least in part on E2 level and/or follicle metric(s) for the patient.

Generally, in some variations, a computer-implemented method for optimizing an ovarian stimulation process may include receiving patient-specific data associated with a patient, identifying a set of prior patients similar to the patient based on the patient-specific data via a similarity matching technique, and generating a predictive dose response curve based on prior patient-specific data associated with the prior patients, wherein the dose response curve predicts egg outcome varying with dose of one or more ovarian stimulation medications (e.g., FSH, LH) administered to the patient. In at least these variations, the patient-specific data may include one or more baseline measurements selected from the group consisting of: measurements of estradiol (E2), measurements of luteinizing hormone (LH), measurements of progesterone (P4), measurements of follicle stimulating hormone (FSH), measurements of anti-mullerian hormone (AMH), and measurements of antral follicle count (AFC). In some variations, the at least one predictive model may be configured to provide the predicted egg outcome associated with each of a first dose of ovarian stimulation medication and a second dose of ovarian stimulation medication higher than the first dose (e.g., a low dose and a high dose, respectively. Additionally or alternatively, in some variations, the at least one predictive model may be configured to provide the predicted egg outcome associated with each of a first dose ratio of multiple ovarian stimulation medications and a second dose ratio of multiple ovarian stimulation medications, wherein the first dose ratio is different than the second dose ratio. For example, the at least one predictive model may be used to predict egg outcome associated with a first FSH/LH dose ratio, and egg outcome associated with a second FSH/LH different from the first LSH/LH dose ratio.

In some variations, in predicting egg outcome associated with different candidate ovarian stimulation medication doses, the method may include identifying a set of prior patients similar to the patient based on the patient-specific data via a similarity matching technique (e.g., incorporating a KNN model), where the at least one predictive model may include a predictive dose response curve generated based on the prior patient-specific data associated with the prior patients. The dose response curve may predict the egg outcome varying with dose of one or more ovarian stimulation medications administered to the patient. In some variations, the method may further include classifying the patient as one of: (i) a dose-responsive patient having predicted egg outcomes that substantially vary with the dose of one or more ovarian stimulation medications administered to the patient, and (ii) a dose non-responsive patient having predicted egg outcomes that do not substantially vary with dose of one or more ovarian stimulation medications administered to the patient, wherein the classification is based at least in part on a shape of the dose response curve. In some variations, when the patient is classified as a dose-responsive patient, recommending an optimal dose of the one or more ovarian stimulation medications to be administered to the patient, based on a point of the dose response curve associated with a predicted maximum egg outcome. Additionally or alternatively, the method may include displaying the predictive dose responsive curve on a display, such as to aid a medical professional in selecting among the candidate doses of ovarian stimulation medication(s). In some variations, the method may further include displaying a confidence interval around the dose response curve, and/or displaying a cost estimate for administering different doses of one or more ovarian stimulation medications in accordance with the dose response curve.

Generally, in some variations, a method for optimizing an ovarian stimulation process may include receiving patient-specific data associated with a patient, predicting, via a first predictive model, a first egg outcome resulting from administering a hormonal trigger injection on a first candidate hormonal trigger day, and predicting, via a second predictive model, a second egg outcome resulting from administering the hormonal trigger injection on a second candidate hormonal trigger day, where the hormonal trigger injection is configured to cause follicle maturation in the patient. The first and/or second egg outcomes may be displayed on a display, such as to aid a medical professional in selecting among the candidate hormonal trigger days.

For example, the first day may be a current day (day on which the first predictive model is run) and the second day may be a future day (e.g., the day after the current day, or two days after the current day). In these variations, the patient-specific data may include, for example, current day follicle size(s) and/or other follicle metric(s), current day estradiol (E2) level for the patient, and/or current day progesterone (P4) for the patient. The predicted egg outcome may, for example, include number of eggs retrieved and/or number of mature eggs. The first predictive model and/or the second predictive model may include, for example, a recurrent neural network or a linear regression model. The recurrent neural network may, for example, be configured to forecast E2 level and/or forecast follicle metric(s) for the patient at a future date. The linear regression model may, for example, be configured to predict the first and/or second outcome based at least in part on E2 level and/or follicle metric(s) for the patient.

Generally, a computer-implemented method may include receiving patient-specific data associated with a patient, and predicting at least one egg outcome for the patient based on at least one predictive model and the patient-specific data. The patient-specific data may include a follicle size classified into a bin from a plurality of predetermined bins, where each bin of the plurality of predetermined bins may be associated with a respective range of follicle sizes, and where the at least one predictive model may be trained using prior patient-specific data associated with a plurality of prior patients. In some variations, the patient-specific data may include an E2 level for the patient, and the method may further include predicting at least one egg outcome based on the E2 level. In some variations, the method may further include displaying the predicted egg outcome on a display (e.g., to a medical professional).

The plurality of bins may be associated with any suitable sets of follicle size ranges. For example, in some variations at least one bin of the plurality of bins may be associated with at least a first follicle size range of about 10 mm or less, a second follicle size range of about 11 mm-13 mm, a third follicle size range of about 14 mm-15 mm, a fourth follicle size range of about 16 mm-17 mm, a fifth follicle size range of about 18 mm-19 mm, a sixth follicle size range of greater than about 20 mm, or any suitable subset thereof.

Generally, in some variations, a computer-implemented method may include receiving patient-specific data associated with a patient, predicting an egg outcome for the patient for each of a plurality of days based on at least one predictive model and patient-specific data, where the at least one predictive model may be trained using prior patient-specific data associated with a plurality of prior patients, and displaying a trend of the predicted egg outcomes for the plurality of days on a display. The predicted egg outcome may, for example, include at least one of number of eggs retrieved and number of mature eggs. Additionally or alternatively, the predicted egg outcome may include at least one of maturity yield, number of post-mature eggs, number of fertilized eggs, number of embryos, number of blastocysts, number of usable blastocysts, number of euploid blastocysts, fetal heartbeat, and live birth rate.

Generally, a method of treatment may include providing patient-specific data associated with a patient, receiving a predicted egg outcome associated with each of a plurality of treatment options, wherein at least one predicted egg outcome is generated with at least one predictive model in accordance with any of the methods described above, selecting a treatment option based on the predicted egg outcomes; and administering an ovarian stimulation medication in accordance with the selected treatment option.

BRIEF DESCRIPTION OF THE DRAWINGS

FIG. 4 is an exemplary variation of a display that displays an Electronic Medical Record (EMR) that is connected to an RE Application via a browser plug-in.

FIG. 12B illustrates a prediction of egg outcomes at a future date using a combination of techniques.

FIGS. 17A-17C illustrate another example of implementing one or more models described herein to predict a trigger day for a patient so as to maximize egg outcome.

FIG. 21A illustrates an example curve that associates egg outcome with dosage amount for a dose-responsive patient.

FIG. 21B illustrates an example curve that associates egg outcome with dosage amount for a dose non-responsive patient.

FIGS. 22A and 22B illustrate an example workflow displayed on a display via an RE Application that an RE can view to assist treatment during an ovarian stimulation.

FIG. 23 illustrates an example patient dashboard displayed on a display of a suitable computing device.

DETAILED DESCRIPTION

Figure 1:
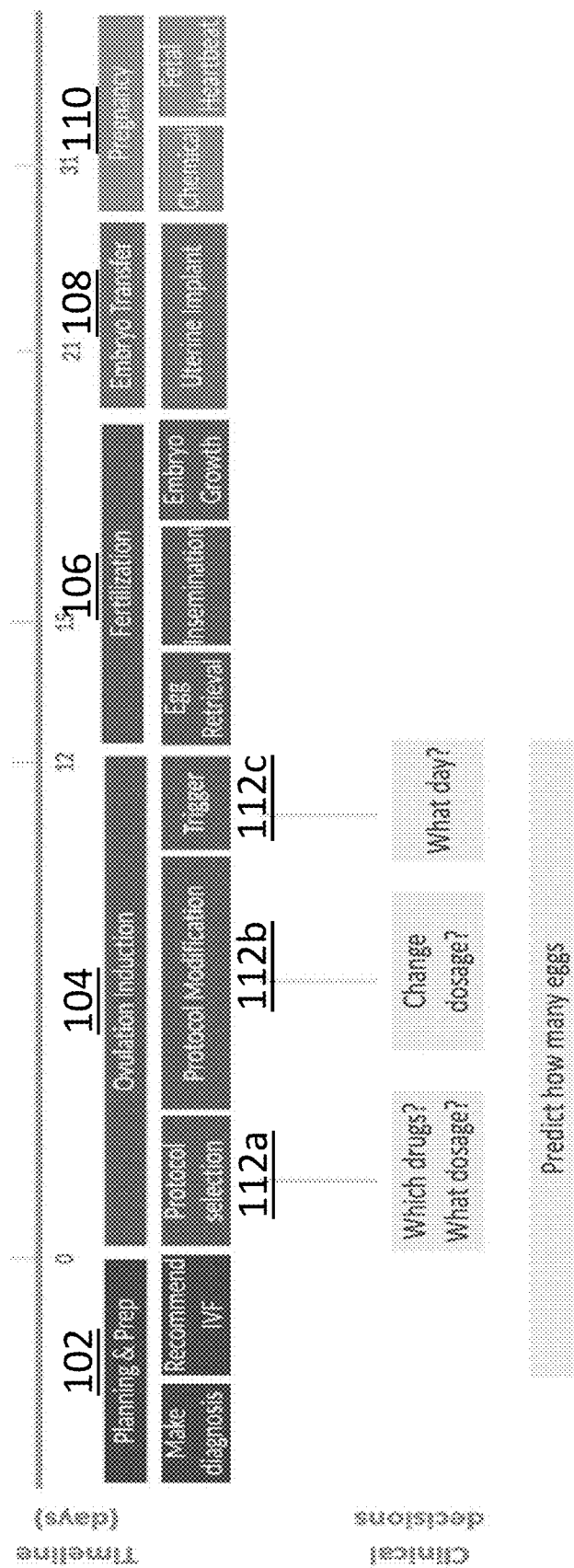
FIG. 1 illustrates exemplary treatment decision points during ovarian stimulation.

Non-limiting examples of various aspects and variations of the invention are described herein and illustrated in the accompanying drawings.

In vitro fertilization (IVF) is a complex reproductive assisted technology that involves fertilization of eggs outside the body in a laboratory setting. A typical IVF cycle includes an ovarian stimulation phase. The goal during the ovarian stimulation phase is to harvest as many mature eggs as possible. During this phase, a patient may be prescribed medication and/or injections that stimulate ovaries to promote multi-follicular growth. Each follicle may include an egg that could potentially mature. A final trigger injection given to a patient that includes hormones that can cause developing follicles to mature may mark the end of the ovarian stimulation phase.

Following ovarian stimulation, a reproductive endocrinologist (RE) and/or a physician may retrieve the eggs from the ovary of the patient (e.g., egg retrieval phase). The eggs may then be fertilized (e.g., fertilization phase) in a laboratory setting. Once fertilized, the embryos may begin to develop (e.g., embryo development phase). The RE may then select the most viable embryo for embryo transfer (e.g., embryo transfer phase).

During each phase of the IVF treatment, there may be a risk of egg or embryo loss due to factors such as maturation failure (e.g., post maturity, pre maturity, etc.), fertilization failure, developmental arrest, or detection of genetic abnormalities. A viable embryo that remains unaffected by these factors may lead to a successful pregnancy and consequently a live birth. Therefore, in order to maximize the probability of a live birth, the ovarian stimulation phase may need to be optimized. For example, by optimizing (e.g., maximizing number of mature eggs or otherwise obtaining an ideal/most suitable/desired number of mature eggs) the number of mature eggs during the ovarian stimulation phase, the probability of a live birth may be maximized.

Mature eggs are developed from follicles. A follicle is a small sac of fluid in the ovaries that contains a developing egg. Typically, during a regular menstrual cycle, several follicles (each of which may contain an egg) may grow. However, usually only a single dominant follicle reaches maturity. The dominant follicle may grow to a stage when it is ready to release a mature egg. This usually occurs around 12-14 days into the monthly menstrual cycle. During an ovarian stimulation stage of an IVF cycle, a patient may be prescribed hormones in order to promote multi-follicular development so that numerous mature eggs can be retrieved. The combination of drugs, dosages, and/or injections prescribed to promote the multi-follicular development may constitute a stimulation protocol.

Some commonly used stimulation protocols include Antagonist Protocol, Long Protocol, and Flare Protocol. Each of these stimulation protocols may share three common functions: (1) the use of gonadotropins such as follicle stimulating hormone (FSH) and luteinizing hormone (LH) to stimulate multi-follicular growth, (2) the use of gonadotropin releasing hormone (GnRH) agonists or antagonists to suppress premature ovulation, and (3) a final hormonal trigger injection to help the eggs undergo meiosis and prepare for release at the right moment.

Conventionally, an RE assesses a patient and prescribes a stimulation protocol for a patient. FIG. 1 illustrates certain decision points faced by an RE during the ovarian stimulation phase. As shown in FIG. 1, at the start of an IVF cycle (e.g., planning and preparation phase 102) and prior to the ovarian induction phase 104, an RE may make a diagnosis and recommend an IVF cycle. In some variations, the patient undergoes fertility testing that may show base level hormones in the patient. Based on the patient's pregnancy history and the results of the fertility testing, the RE may make a diagnosis for the patient. This may include whether or not to recommend IVF treatment for the patient.

Once an IVF treatment and an IVF cycle are recommended for the patient, the treatment may proceed to the ovarian stimulation phase. During the ovarian stimulation phase, the RE may be faced with multiple decisions that may affect the outcome of the IVF cycle and the health of the patient. One such decision may include determining the stimulation protocol (e.g., 112a) to be prescribed for the patient. For example, the RE may determine the drugs to be used and the starting dosage of the drugs. After the stimulation protocol (e.g., 112a) has been selected, the RE may monitor the patient regularly to assess the response of the patient to the stimulation protocol. Based on the patient's response, the RE may modify the stimulation protocol (e.g., 112b) and/or may cancel the IVF cycle. This may be the next clinical decision that the RE may have to make during the ovarian stimulation phase. For example, if the patient's response to the stimulation protocol is lower than expected, the RE may increase the dosage of gonadotropins. Conversely, if the patient's response to the simulation protocol is higher than expected, the RE may decrease the dosage of gonadotropins. Furthermore, if the patient's response to the simulation protocol is too high or too low, then the RE may cancel the IVF cycle. The final clinical decision during the ovarian stimulation phase may include determining when to prescribe the final trigger injection (e.g., 112c) to the patient that helps the eggs undergo meiosis and prepare to be released. The final trigger injection may cause developing follicles to mature. The day on which the final trigger injection (e.g., 112c) is prescribed may be pivotal to the outcome of the IVF cycle.

After the final trigger injection is administered, the eggs may be retrieved during the fertilization phase 106. During the fertilization phase 106, the retrieved eggs may be fertilized. The embryos may be analyzed as they grow to determine one or more viable embryos for transfer. A viable embryo may be transferred during the embryo transfer phase 108 which may subsequently lead to a pregnancy 110.

Traditionally, the clinical decisions made during the ovulation induction phase 102 may be made based on the RE's experience and the RE's assessment of the patient. However, these clinical decisions may be subjective and specific to each individual RE's experience. It may be possible that two different REs may make different decisions for the same patient. For instance, two different REs may prescribe different stimulation protocols for the same patient. Similarly, one RE may choose to cancel the IVF protocol based on the patient's response to the stimulation protocol, while a different RE may choose to modify the stimulation protocol based on the patient's response to the stimulation protocol. These decisions may be highly subjective, thereby making it difficult to standardize the ovarian stimulation phase.

Some existing methods use data from previous patients to generate one or more models that may predict the clinical decisions for the REs. Such models may replace the decisions that the RE may make. This can be challenging since replacing or superseding the clinical judgment of an RE may not always result in a successful IVF outcome. For instance, for a complicated or unusual case, the data available (e.g., data used to generate the model(s)) may be limited. Consequently, the predictions that the model(s) make may not be accurate. However, an RE with several years of training and experience may be better equipped to make clinical decisions for such complicated and rare cases to result in a more desirable patient outcome. Furthermore, other factors that may not be apparent in the data available, such as variability in clinic policies, clinic offerings, and patient context such as unknown genetic disease that may lead to unexplained fertility issues, etc., may be essential to making the best clinical decisions for the patient. In addition, existing methods and models use black-box approaches to predict clinical decisions for the REs. Such approaches typically do not generate interpretable results.

Accordingly, what is needed is a technology that can augment or further inform the RE's decisions as opposed to replacing them. The technology described herein develops and implements machine-learning models (also referred to herein as "predictive models") to augment clinical decisions made by REs. These machine-learning models may be trained on diverse and high-quality data. Instead of replacing the RE's decisions, these machine-learning models may, for example, provide helpful second opinions and/or augment the RE's decision. Furthermore, for unusual or complicated cases, the machine-learning models may be used in conjunction with an RE's decisions so as to provide a more accurate prediction that may result in a successful IVF outcome. The predictions are generated such that the results may be easily interpreted by the REs.

The technology described herein uses machine-learning to predict egg outcome in contrast to clinical decisions for REs. The egg outcome may be used as additional information to augment the RE's decision. Some non-limiting examples of egg outcome may include number of eggs, number of mature eggs, maturity yield, number of post-mature eggs, number of fertilized eggs, number of embryos, number of blastocysts, number of euploid blastocysts, fetal heartbeat, chemical pregnancy rate, live birth rates, live birth rates accumulated across successive transfers, a combination thereof, and/or the like.

In some variations, a computer-implemented method may include receiving patient-specific data that may be associated with a plurality of prior patients. The patient-specific data may include data relating to ovarian stimulation. A predictive model may be trained based on the patient-specific data. The computer-implemented method may include receiving a first patient-specific data associated with a first patient undergoing an IVF treatment (e.g., an IVF cycle). The computer-implemented method may include predicting an egg outcome for the first patient based on an implementation of the predictive model for the first patient-specific data associated with the first patient.

System Overview

Figure 2:
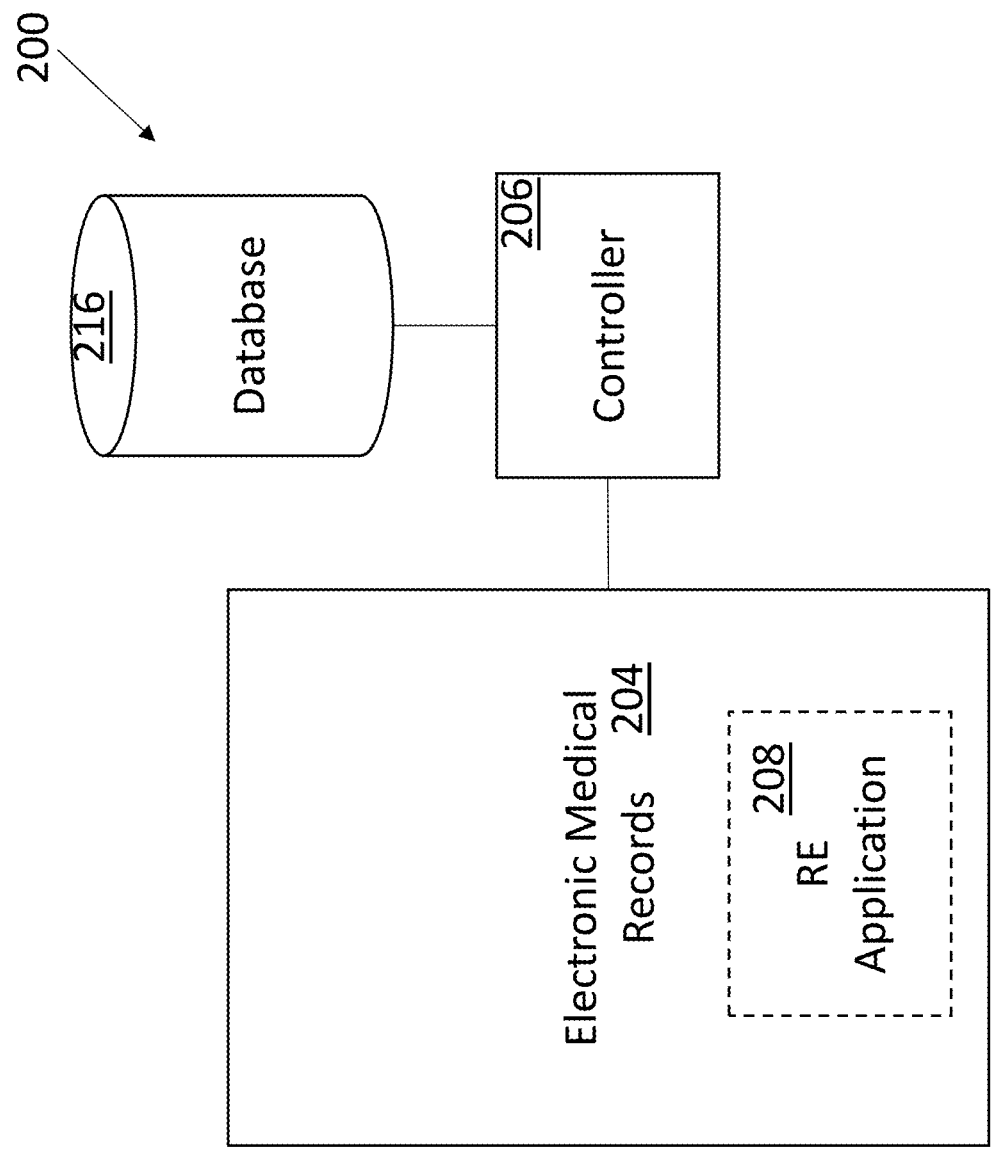
FIG. 2 illustrates an overview of an exemplary variation of a system for assisting treatment during ovarian stimulation.

FIG. 2 illustrates an overview of an exemplary variation of a system 200 for assisting REs during the ovarian stimulation phase. The system 200 may access and/or retrieve data from reliable electronic medical records (EMR) 204. A controller 206 may implement machine-learning models using the data retrieved from EMR 204. The machine-learning models may predict an egg outcome for a patient. The predictions from the machine-learning models may be transmitted to an RE application 208 being implemented on a suitable computing device. In some variations, the RE application 208 may interface with the EMR 204. In some variations, the predictions from the machine-learning models may be stored in a database 216. In some variations, these predictions may be accessed from the database 216 at a future time to further improve the accuracy of the machine-learning models. An RE may access the predictions on the RE application 208 to augment their clinical decisions.

The EMR 204 may be a reliable database such as eIVF™ patient portal, Artisan™ fertility portal, Babysentry™ management system, EPIC™ patient portal, IDEAS™ from Mellowood Medical, etc., or any suitable electronic medical record management software. In some variations, the EMR 204 may be associated with a specific clinic. In such variations, the EMR 204 may be configured to interface with one or more servers associated with the specific clinic. In some variations, the EMR 204 may be hosted on a cloud-based platform (e.g., Microsoft Azure®, Amazon® web services, IBM® cloud computing, etc.).

In some variations, the EMR 204 may be associated with a specific clinic. For example, the EMR 204 from a specific clinic may not be shared with other hospitals, pharmacies, practitioners, etc. Additionally or alternatively, the EMR 204 may be configured to access databases associated with each clinic. The EMR 204 may automatically extract relevant information from a patient's chart and might match it against a database of de-identified medical records. Accordingly, the relevant data across several entities (e.g., clinics, hospitals, pharmacies, practitioner, etc.) may be extracted from the EMR 204 without compromising the privacy of the patients (e.g., by maintaining Health Insurance Portability and Accountability Act regulations).

The EMR 204 may be accessed via a computing device. Some non-limiting examples of the computing device include computers (e.g., desktops, personal computers, laptops etc.), tablets and e-readers (e.g., Apple iPad®, Samsung Galaxy® Tab, Microsoft Surface®, Amazon Kindle®, etc.), mobile devices and smart phones (e.g., Apple iPhone®, Samsung Galaxy®, Google Pixel®, etc.), etc. For example, EMR 204 may be stored on a memory associated with the computing device. Alternatively, the EMR 204 may be accessed online through a web browser (e.g., Google®, Mozilla®, Safari®, Internet Explorer®, etc.) rendered on the computing device. In yet another alternative variation, the EMR 204 may be stored on a third-party database that may be accessed via the computing device.

Patient-specific data may be extracted from the EMR 204. Patient-specific data extracted from the EMR 204 may refer to: (1) data associated with one or more patients that may include the description, content, values of records, a combination thereof, and/or the like; and/or (2) metadata providing context for the said data. For example, patient-specific data extracted from the EMR 204 may include one or both the data and metadata associated with patient records.

Some non-limiting examples of patient-specific data extracted from the EMR 204 may include: (a) patient information such as age, body mass index, race, ethnicity, diagnoses or causes of infertility, prior IVF history, prior uterine surgery information, prior intrauterine insemination (IUI) history, prior pregnancy or live birth history from natural conception, and/or the like; (b) data relating to prior IVF cycles and/or treatments such as baseline measurements of drugs and hormones, stimulation protocol, response to stimulation protocol, number of eggs retrieved, number of mature eggs, number of successfully fertilized eggs, pregnancy outcome, and live birth outcome during the prior IVF cycles and/or treatments; (c) baseline measurements such as measurements of estradiol (E2), luteinizing hormone (LH), progesterone (P4), follicle stimulating hormone (FSH), anti-mullerian hormone (AMH), antral follicle count (AFC), and/or the like; (d) treatment variables such as type of medication and brands (e.g., for gonadotropins (FSH and LH), GnRH agonists and antagonists, and final trigger injection), amount of drug dosage (e.g., starting dosage, ending dosage, daily dosage, and total drugs), number of cycle days, and/or the like; (e) response to stimulation protocol such as daily measurements of follicle metrics (e.g., follicle counts and sizes), E2 and P4 levels, and/or the like.

In some variations, patient-specific data may also include ultrasound images of the follicle, uterine, etc. The ultrasound images may provide information such as follicle count, follicle size, presence of fibroids in uterine, etc.

A controller 206 communicably coupled to the EMR 204 may extract the patient-specific data (e.g., from the EMR 204). In some variations, the controller 206 may include one or more servers and/or one or more processors running on a cloud platform (e.g., Microsoft Azure®, Amazon® web services, IBM® cloud computing, etc.). The server(s) and/or processor(s) may be any suitable processing device configured to run and/or execute a set of instructions or code, and may include one or more data processors, image processors, graphics processing units, digital signal processors, and/or central processing units. The server(s) and/or processor(s) may be, for example, a general purpose processor, a Field Programmable Gate Array (FPGA), an Application Specific Integrated Circuit (ASIC), and/or the like.

In some variations, the controller 206 may include a processor (e.g., CPU). The processor may be any suitable processing device configured to run and/or execute a set of instructions or code, and may include one or more data processors, image processors, graphics processing units, physics processing units, digital signal processors, and/or central processing units. The processor may be, for example, a general purpose processor, a Field Programmable Gate Array (FPGA), an application Specific Integrated Circuit (ASIC), and/or the like. The processor may be configured to run and/or execute application processes and/or other modules, processes and/or functions associated with the system and/or a network associated therewith. The underlying device technologies may be provided in a variety of component types (e.g., MOSFET technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The controller 206 may use the patient-specific data extracted from the EMR 204 to train one or more machine-learning models. The machine-learning model(s) may predict egg outcome for a patient. For example, the patient-specific data may be used to train a machine-learning model for selecting a stimulation protocol for a patient. The machine-learning model may predict the egg outcome of various stimulation protocols (e.g., Antagonist Protocol, Long Protocol, Flare Protocol, etc.) for the patient. This may help the RE with the clinical decision of determining which stimulation protocol to prescribe to the patient. In a similar manner, the patient-specific data may be used to train a machine-learning model for determining a starting dose of FSH to be prescribed to a patient. The machine-learning model may predict the egg outcome for various starting doses of FSH. This may help the RE with the clinical decision of determining what the starting dosage of FSH should be prescribed for the patient. In yet another alternative variation, the patient-specific data may be used to train a machine-learning model for determining a day on which the patient may be administered the final trigger injection. The machine-learning model may predict the egg outcome for different days on which the final trigger injection may be administered. The RE may use this information for determining the day on which the final trigger injection should be administered for the patient.

In some variations, the machine learning model(s) may augment the RE's clinical decision(s), but do not predict the clinical decisions themselves. For example, the output of the machine learning model(s) may not be a prediction of the stimulation protocol to be described, a prediction of modifications to be made to the stimulation protocol, or a prediction of determining when the final trigger injection may be administered. Rather, in some variations the output of the machine learning model(s) is an egg outcome, where the machine learning model(s) equip the REs to make a more informed decision using the egg outcome for various scenarios. For example, in this manner, such machine learning model(s) whose output is an egg outcome may help the REs verify their individual assessment of their clinical decisions rather than replacing their decisions altogether. Alternatively, in some variations, the machine learning model(s) may output one or more clinical decisions themselves.

Figure 3:
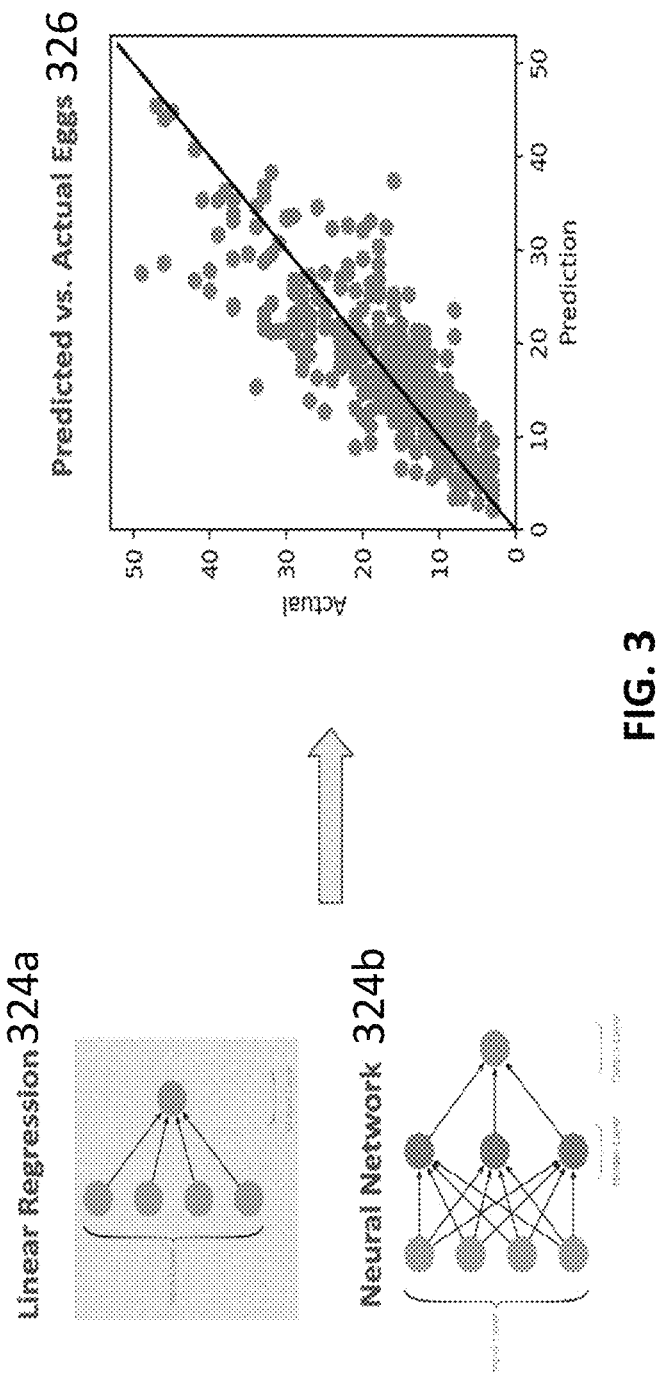
FIG. 3 is an exemplary variation of a linear regression model and a neural network that predict egg outcomes for patients.

In some variations, the machine-learning models may be a series of regression models. As a non-limiting example, the machine-learning models may be a series of regression models for selecting a stimulation protocol for a patient, determining a starting dose of FSH to be prescribed to a patient, determining a day on which a patient may be administered the final trigger injection, and/or the like. In some variations, the regression models may be linear regression models. Additionally or alternatively, the machine-learning models may be a feedforward neural network and/or a recurrent neural network. As described above, the machine-learning models may predict egg outcome for a patient. FIG. 3 is an exemplary variation of a linear regression model 324a and a neural network 324b. The linear regression model 324a and the neural network 324b may predict egg outcome (e.g., number of eggs, number of mature eggs, etc.) for various patients as seen in graph 326. Graph 326 shows the number of predicted eggs vs. actual eggs retrieved from various patients. As seen in graph 326, the predicted egg outcome is close to the actual egg outcome. As an example, the neural network 324b may be a feedforward neural network. For instance, the feedforward neural network may be a 3-layer network with ReLU activation and dropout, trained with a gradient descent optimizer to minimize the mean squared error.

In some variations, the accuracy of the machine-learning model(s) may improve as more patient-specific data becomes available to train the machine-learning model(s). For example, referring to Table 1, before the ovarian stimulation phase after a patient has been accepted for IVF, the patient-specific data available to train the model may include diagnosis, age, BMI, amount of FSH and Estradiol associated with various prior patients. The R-squared value for predictions of egg outcome at this stage shows a value of 0.28, implying that the predicted egg outcome and the actual egg outcome may not be too similar. However, during the next stage before the ovarian stimulation, the patient-specific data may additionally (e.g., in addition to age, BMI, amount of FSH and Estradiol, etc.) include baseline AFC and baseline AMH. The R-squared value for predictions of egg outcome at this stage shows a value of 0.45. During the ovarian stimulation, in addition to age, BMI, amount of FSH and Estradiol, baseline AFC, and baseline AMH, the patient-specific data may also include the type of stimulation protocol, cycle days, and the amount of dosages of medication associated with the various prior patients. The R-squared value for predictions of egg outcome at this stage shows a value of 0.50. After the ovarian stimulation and before the egg retrieval, the patient-specific data may additionally include the number of follicles. The R-squared value for predictions of egg outcome at this stage shows a value of 0.70. Accordingly, as seen in Table 1, the predictions improve as more patient-specific data becomes available.

TABLE 1

| Stage | Patient-Specific data | R-squared | Mean Absolute Error (#eggs) |
|---|---|---|---|
| Accepted for IVF | Diagnosis, age, BMI, FSH, Estradiol | 0.28 | 5.88 |
| Before Stimulation | +Baseline AFC, Baseline AMH | 0.45 | 4.98 |
| Stimulation | +Protocol, cycle days, dosages, | 0.50 | 4.78 |
| Before retrieval | +Number of follicles | 0.70 | 3.60 |

In some variations, the output of the machine-learning model(s) may be stored in a database 216. More specifically, the egg outcome for a patient and patient-specific data (e.g., patient information, data relating to prior IVF cycles and/or treatments, baseline measurements, treatment variable, response to stimulation protocol, etc.) associated with the patient may be stored in the database 216. This data can be incorporated to update the training data of the machine-learning model(s). That is, in addition to already existing patient-specific data, the machine-learning model(s) can be trained on data associated with a patient currently undergoing the IVF treatment. This in turn may improve the accuracy of prediction for the machine-learning model(s).

As discussed above, the output of the machine-learning model(s) and patient-specific data associated with each patient may be stored in the database 216. The database 216 may be accessed at any suitable time to improve the machine-learning model(s) implemented by the controller 206. In some variations, the database 216 may be stored in a memory device such as a random access memory (RAM), a memory buffer, a hard drive, an erasable programmable read-only memory (EPROM), an electrically erasable read-only memory (EEPROM), a read-only memory (ROM), Flash memory, and the like. In some variations, the database 216 may be stored on a cloud-based platform such as Amazon web Services®.

The output of the machine-learning model(s) may be accessible to the REs via an application software (referred to herein as "RE Application" 208) executable on the computing device. In some variations, the computing device may be the computing device through which the EMR 204 is accessed. More specifically, the RE Application 208 may be connected to the EMR 204 so as to extract patient-specific data and the output of the machine-learning model(s) in real-time. In some variations, the RE Application 208 may be connected to the EMR 204 through a website portal connection. Additionally or alternatively, the RE Application 208 may be connected to the EMR 204 as a direct plug-in (e.g., a browser plug-in) to the EMR 204. In some variations, the RE Application 208 may be connected to the EMR 204 via the computing device (discussed above) through which the EMR 204 may be accessed. For instance, the RE Application 208 may be connected to the computing via an Application Programming Interface (API) that in turn may connect the computing device to the EMR 204. Additionally or alternatively, the RE Application 208 may be rendered on the computing device through a web browser (e.g., Google®, Mozilla®, Safari®, Internet Explorer®, etc.). The web browser may also connect the RE Application 208 to the EMR 204.

In some variations, the RE Application 208 (e.g., web apps, desktop apps, mobile apps, etc.) may be pre-installed on the computing device. Alternatively, the RE Application 208 may be rendered on the computing device in any suitable way. For example, in some variations, the RE Application 208 (e.g., web apps, desktop apps, mobile apps, etc.) may be downloaded on the computing device from a digital distribution platform such as an app store or application store (e.g., Chrome® web store, Apple® web store, etc.). Additionally or alternatively, the computing device may render a web browser (e.g., Google®, Mozilla®, Safari®, Internet Explorer®, etc.) on the computing device. The web browser may include browser extensions, browser plug-ins, etc. that may render the RE Application 208 on the computing device. In yet another alternative variation, the browser extensions, browser plug-ins, etc. may include installation instructions to install the RE Application 208 on the computing device.

Figure 4:
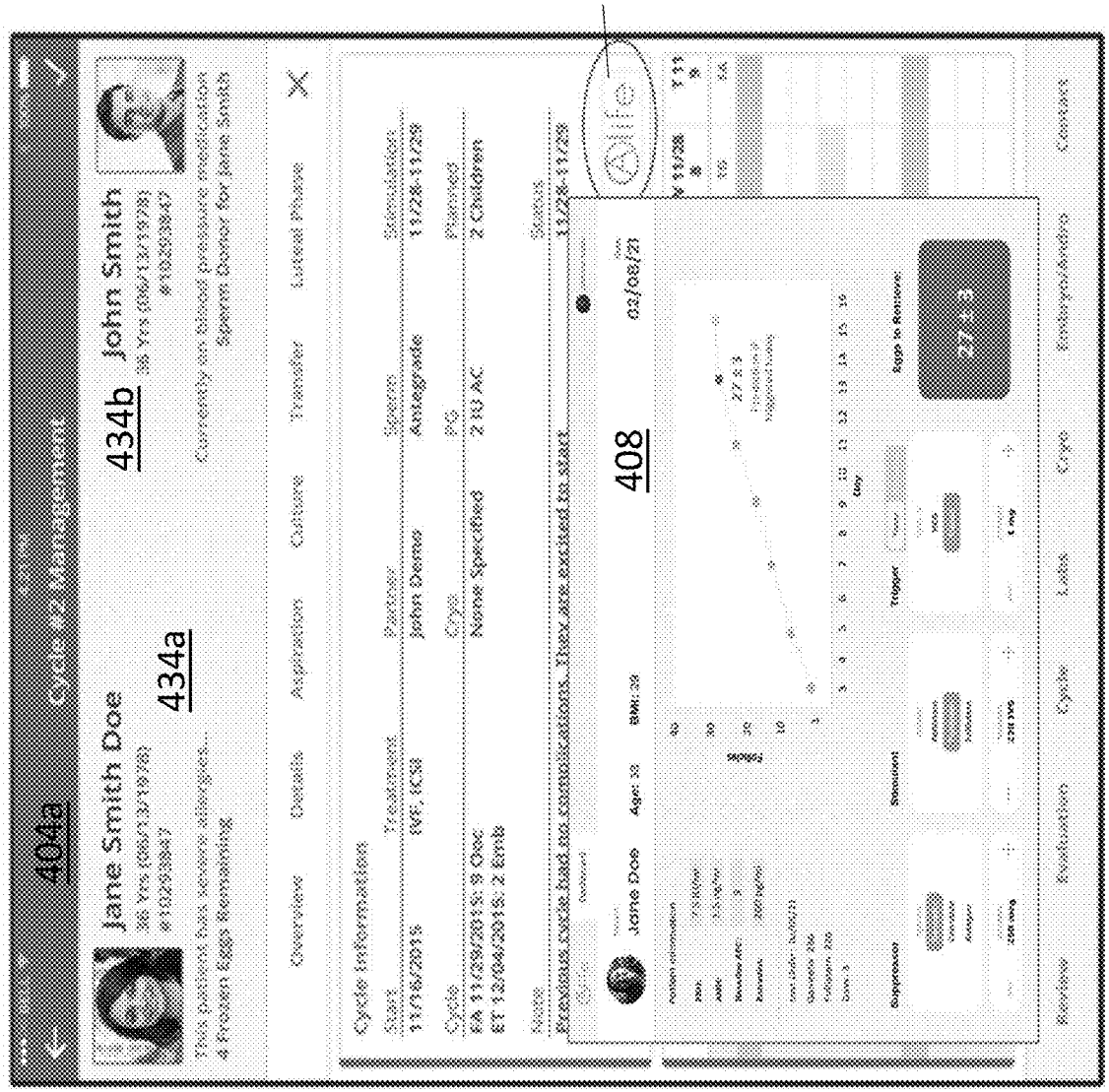

The output of the machine-learning model(s) may be accessed by any user (e.g., patient, RE, other clinicians, etc.) via the RE Application 208 in real-time. For example, the REs may access the output of the machine-learning model(s) via the RE Application 208 in real-time. Additionally, the REs may access, review, and/or edit the patient-specific data associated with the patient in real-time through the EMR 204 connected to the RE Application 208. FIG. 4 is an exemplary variation of a display 432 that displays an EMR 404a. The EMR 404a is connected to a RE Application 408 via a browser plug-in 436.

In FIG. 4, the display 432 may include an EMR 404a associated with a patient "Jane Smith Doe" 434a undergoing the IVF treatment. In some variations, the EMR 404a may also include information associated with the sperm donor (e.g., "John Smith" 434b). The display 432 may include a browser plug-in 436 (e.g., widget, radio button, etc.) that may connect the EMR 404a to the RE Application 408. For example, clicking and/or pressing the browser plug-in 436 may open a pop-up window of the RE Application 408. The RE Application 408 may include one or more outputs of the machine-learning model(s). For example, the RE Application 408 may include prediction of egg outcome for the patient "Jane Smith Doe" 434a. In this manner, a RE can access the patient-specific data (e.g., EMR 404a) associated with "Jane Smith Doe" 434a and simultaneously access the outcome of the machine-learning model(s) by simply clicking and/or pressing the browser plug-in 436.

Figure 5:
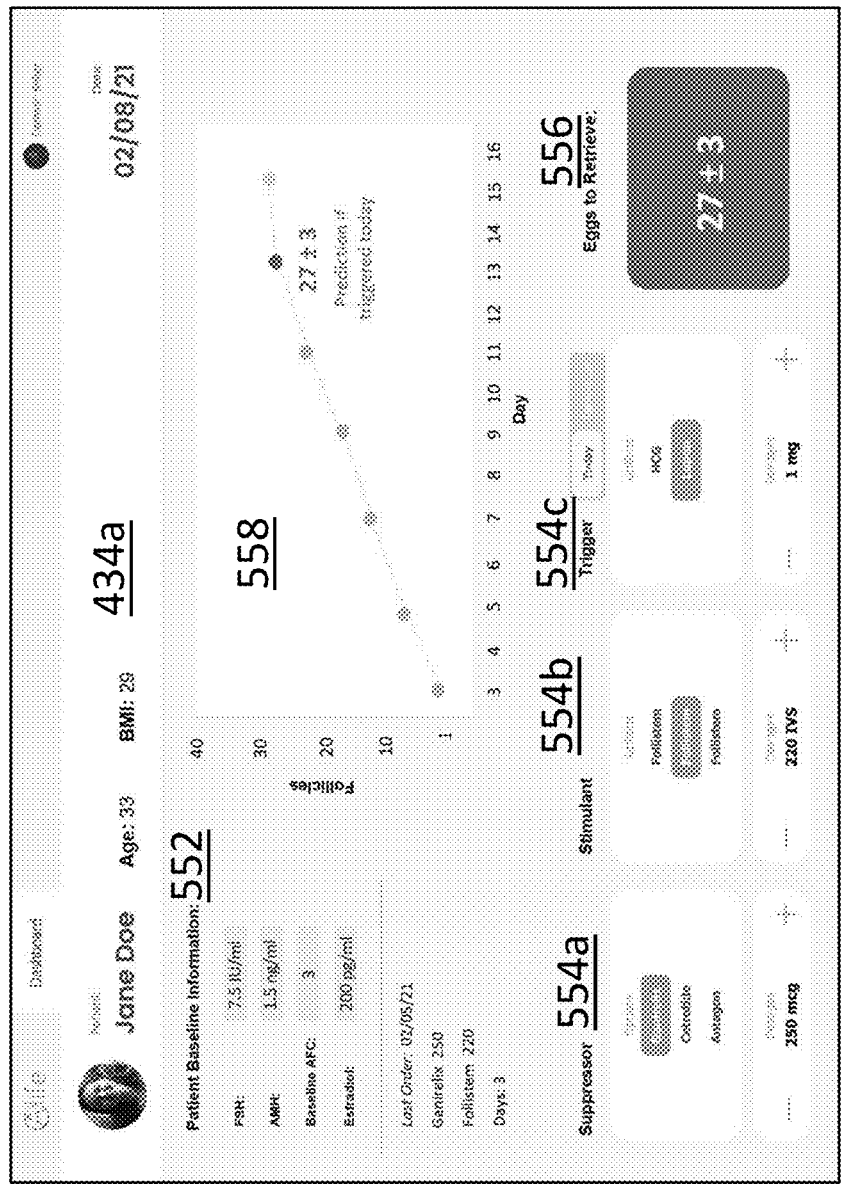
FIG. 5 illustrates an exemplary variation of an RE Application being displayed on a display.

FIG. 5 illustrates an exemplary variation of an RE Application 408 being displayed on a display (e.g., display 432 in FIG. 4). Clicking and/or pressing the browser plug-in 436 may pop open the RE application 408. The RE Application 408 may include patient-specific data associated with "Jane Smith Doe" 434a. In some variations, the RE Application 408 may include baseline measurements 552 such as the levels of FSH, AMH, AFC, Estradiol, etc. In some variations, the RE Application may enable an RE to select a suitable amount of suppressor 554a, a suitable amount of stimulant 554b, a suitable amount of hormone in the final trigger injection 554c, and/or a day on which the final trigger injection is to be administered. Such selection may be made before the beginning of the ovarian stimulation phase or during the ovarian stimulation phase.

For instance, an RE may click on the "+" button located below suppressor 554a to increase the amount of suppressor. Alternatively, an RE may click the "−" button located below suppressor 554a to decrease the amount of suppressor. By altering the measurements of suppressor 554a, stimulant 554b, and hormone 554c, the RE may view in real-time the egg outcome 556 for the various measurements. More specifically, the RE may be able to view in real-time how the egg outcome 556 may be altered for various measurements of suppressor 554a, stimulant 554b, and hormone 554c.

Additionally or alternatively, the RE may be able to change the day on which the final trigger injection is to be administered (e.g., by clicking on the toggle button above hormone 554c). Changing the day may change the egg outcome 556. In some variations, RE Application 408 may also display a graph 558 illustrating the egg outcome for various days of a menstrual cycle. This may provide the RE with the necessary information to determine the day on which the final trigger injection is to be administered.

In some variations, the RE may close the RE Application 408 at any time. The RE Application 408 may be re-opened at any time. On reopening, the graph 558 may be updated to reflect the latest egg outcome. As discussed above, the RE may further modify the patient-specific data to determine how the modifications may affect the prediction and the final outcome.

Exemplary Method to Predict Egg Outcome

Figure 6:
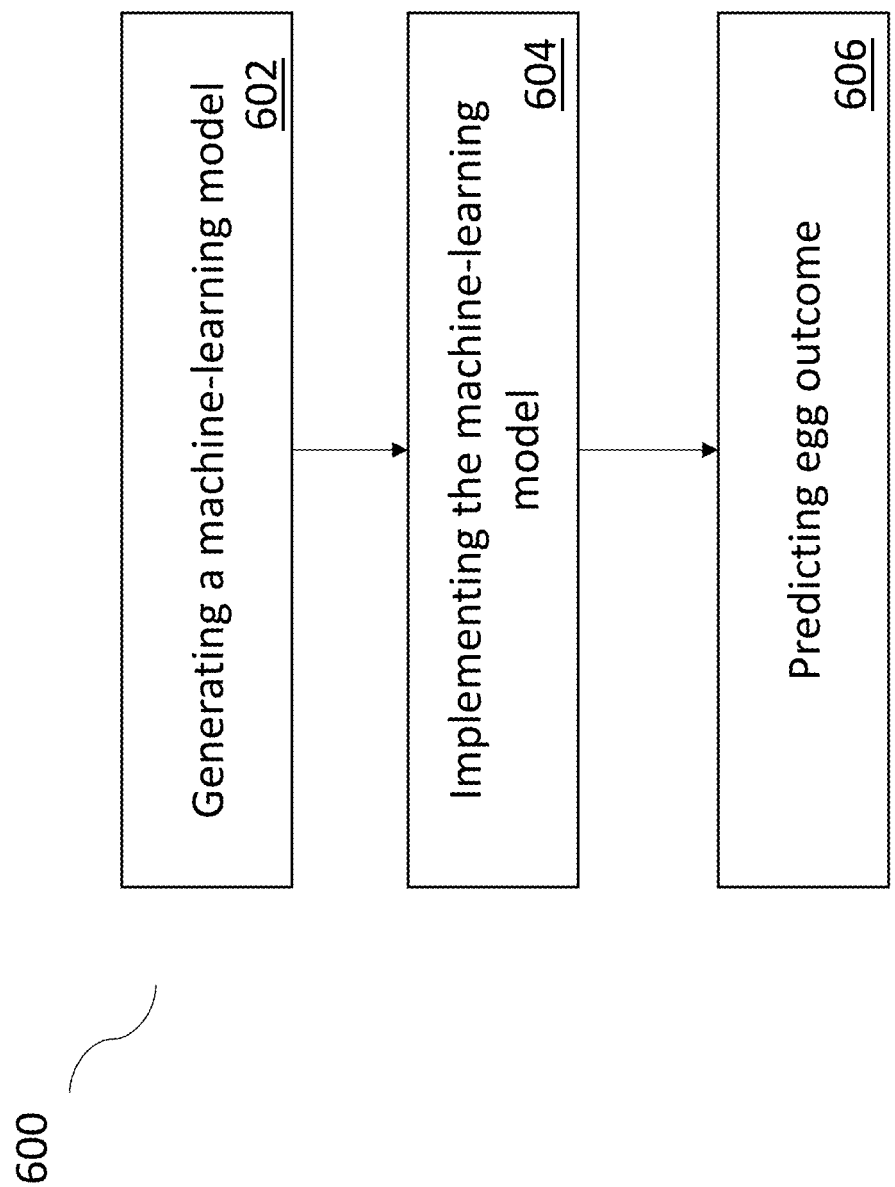
FIG. 6 is a flow diagram illustrating an exemplary variation of a method to predict egg outcome.

FIG. 6 is a flow diagram illustrating an exemplary variation of a method 600 to predict egg outcome. At 602, the method includes receiving patient-specific data from EMRs. A controller (e.g., controller 206 in FIG. 2) may receive patient-specific data from EMRs (e.g., EMR 204 in FIG. 2). The patient-specific data may include a vast amount of data associated with previous patients. For example, the patient-specific data may include patient information, ultrasound images, data relating to prior IVF cycles and/or treatments, baseline measurements, treatment variable, response to stimulation protocol, etc. associated with previous patients.

The patient-specific data may be used to train machine-learning model(s). In some variations, the machine-learning model(s) may be linear regression models. Alternatively, the machine-learning model(s) may include a neural network such as feedforward neural network, recurrent neural network, etc. Alternatively, the machine learning model(s) may include K-nearest-neighbors (KNN).

When a patient is undergoing IVF treatment, patient-specific data associated with the patient may be received at the controller. At 604, the method may include implementing the machine-learning model(s) for the patient undergoing the IVF treatment. This may include, for example, implementing a linear regression model and/or a neural network trained on patient-specific data obtained from EMR. The linear regression model and/or the neural network may be implemented for the data associated with the patient. For example, the linear regression model and/or the neural network may be implemented for the patient's age, race, body mass index, previous IVF history, pregnancy, live birth, etc.

At 606, implementing the machine-learning model(s) may cause the method 600 to predict an egg outcome. The egg outcome may include number of eggs, number of mature eggs, maturity yield, number of post-mature eggs, number of fertilized eggs, number of embryos, number of blastocysts, number of euploid blastocysts, fetal heartbeat, chemical pregnancy rate, live birth rates, a combination thereof, and/or the like. For instance, the machine-learning model(s) may predict the egg outcome for various stimulation protocols for the patient. Similarly, the machine-learning model(s) may predict the egg outcome for various baseline dosages of medication for the patient. In a similar manner, the machine-learning model(s) may predict the egg outcome for various days on which the final trigger injection is to be administered for the patient. Additionally or alternatively, the machine-learning model(s) may predict the egg outcome for various amounts of hormone to be included in the final trigger injection.

As the patient is undergoing the ovarian stimulation, the patient's response to the stimulation protocol may be observed. The machine-learning model(s) may be implemented to account for the response of the patient. The stimulation protocol may be canceled and/or altered based on the patient's response. This may include varying the dosage of medication based on how the patient responds to the baseline amount of medication.

Some non-limiting examples of machine-learning models and their implementation are further described as below.

Stimulation Protocol Selection Model

In some variations, a stimulation protocol selection model may be trained on patient information such as age, prior IVF history, prior intrauterine insemination (IUI) history, prior pregnancy or live birth history from natural conception and/or baseline measurements such as anti-mullerian hormone (AMH), antral follicle count (AFC), body mass index, race, ethnicity, ultrasound images, and/or the like. In some variations, the training data may additionally include contextual information such as cost of IVF treatment, cost restrictions for the patient, other patient-specific needs, etc.

In some variations, the stimulation protocol selection model may be a linear regression model. In some variations, the stimulation protocol selection model may implement K-nearest neighbors (KNN) technique. The stimulation protocol selection model may incorporate the patient-specific data (e.g., patient information, baseline measurements, contextual information) discussed above to predict egg outcome for a patient. The egg outcome may be number of eggs and/or number of matured eggs that may be retrieved from the patient.

Typically, REs may make clinical decisions on the type of stimulation protocol to prescribe to a patient. If a patient is an average responder, REs will most likely prescribe Antagonist protocol. In some variations, the RE may know that the patient is an average responder if the current IVF cycle is not the first IVF cycle with the RE. However, in variations in which the current IVF cycle is the first IVF cycle, the RE may assess the type of responder the patient might be based on patient information. If a patient has had a previous low response (e.g., in a previous IVF cycle), or is expected to have a low response, then the RE may prescribe an alternative protocol.

To augment the clinical decision relating to the type of stimulation protocol, the stimulation protocol selection model may predict the egg outcome for a specific protocol (e.g., Antagonist protocol). If the egg outcome is less than a first threshold value, then the patient may be classified as a low responder. However, if the egg outcome is between a certain range that may be higher than the first threshold value, then the patient may be classified as a medium responder. In contrast, if the egg outcome is higher than a second threshold value (e.g., greater that the highest value of the range classified as a medium responder), then the patent may be classified as a high responder. In some variations, the RE may choose the first threshold value, the range, and/or the second threshold value. The REs may therefore customize the classifications so as to tailor the stimulation protocol towards specific patients. For example, the RE may choose a threshold of fewer than 5 eggs to indicate a low response in some patients, but a threshold of fewer than 8 eggs to indicate a low response in other patients.

If a patient is classified as a low responder, then the RE may select an alternative stimulation protocol. The stimulation protocol selection model may then be implemented for the alternative stimulation protocol. The stimulation protocol selection model may optimize the egg outcome for the patient using the alternative stimulation protocol. For example, if the patient is a low responder, the stimulation protocol model may optimize the egg outcome for the patient using the alternative stimulation protocol.

In some variations, if a patient has already undergone an IVF cycle, the RE's initial selection of the stimulation protocol, the patient's response to the stimulation protocol, and/or modification to the stimulation protocol may be incorporated into the stimulation protocol selection model. This may provide for a more accurate prediction during subsequent IVF cycles. In some variations, separate prediction models may be generated by incorporating detailed previous IVF history for the patient. Such prediction models may be tailored for the patient and may be comparatively more accurate during the second, third, or later IVF cycle.

Figure 26:
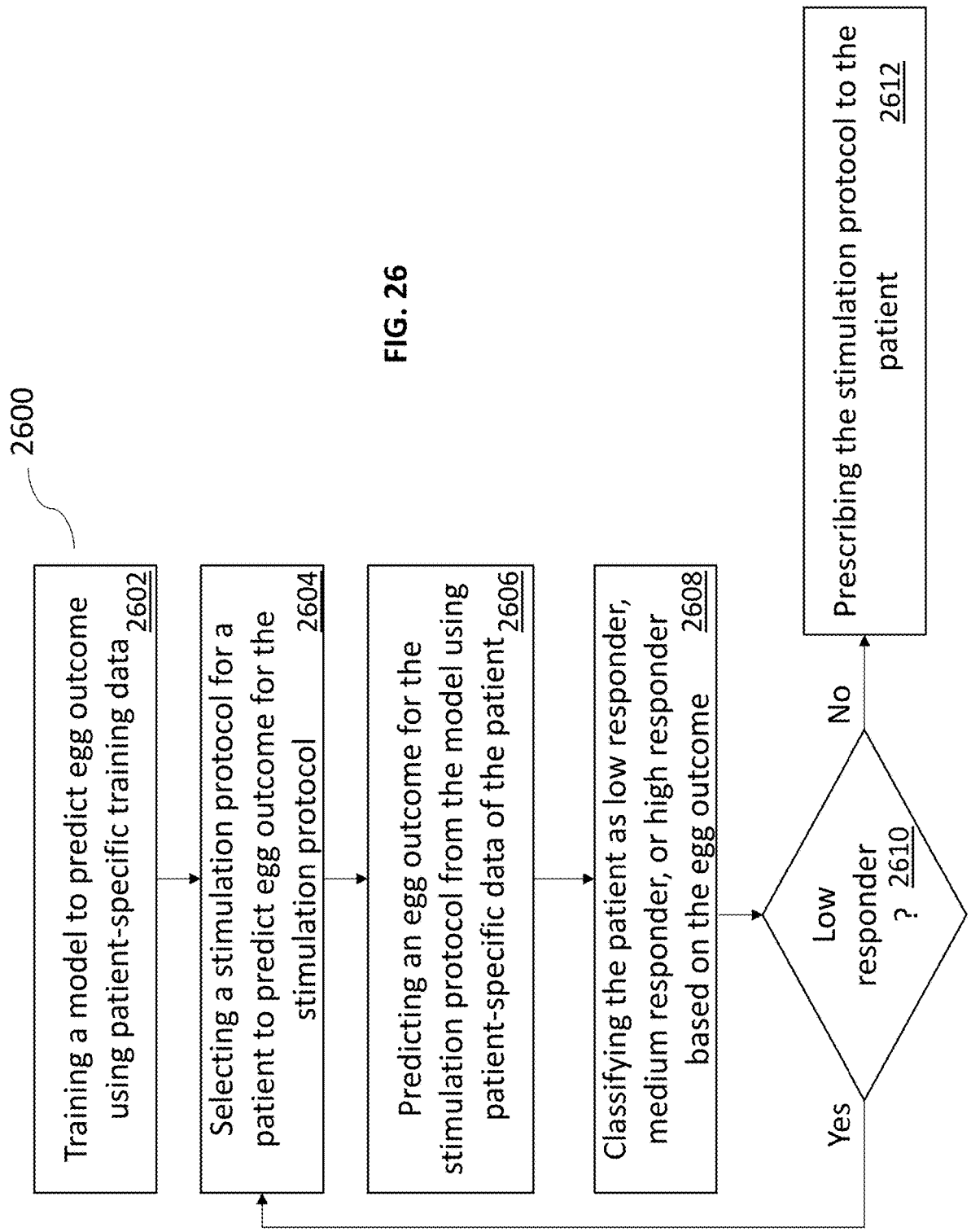
FIG. 26 is a flow diagram illustrating an exemplary variation of a method for prescribing a stimulation protocol to a patient.

FIG. 26 is a flow diagram illustrating an exemplary variation of a method 2600 for providing a stimulation protocol to a patient. At 2602, the method 2600 may include training a model (e.g., linear regression model, KNN model, etc.) to predict egg outcome for a patient using patient-specific training data, as further described in detail herein. The patient-specific training data may include patient information for various patients who may have previously undergone one or more IVF cycles. The patient information may include, for example, information such as age, prior IVF history, prior intrauterine insemination (IUI) history, prior pregnancy or live birth history from natural conception and/or baseline measurements such as anti-mullerian hormone (AMR), antral follicle count (AFC), body mass index, race, ethnicity, ultrasound images, prior stimulation protocol that was selected, egg outcome related to the stimulation protocol, cost of IVF treatment, cost restrictions associated with each patient, and/or the like.

At 2604, the method 2600 may include for a patient-of-interest (e.g., a patient starting and/or a patient undergoing IVF treatment), selecting a stimulation protocol to predict egg outcome for the stimulation protocol. For example, if a patient-of-interest has already undergone previous IVF cycles, the method 2600 may include selecting an antagonist protocol for the patient. However, if the patient-of-interest has not undergone any previous IVF cycles, the method 2600 may include selecting an alternative protocol (e.g., other than antagonist protocol) for the patient.

After selecting a stimulation protocol, at 2606, the method 2600 may include predicting an egg outcome for the selected stimulation protocol by inputting patient-specific data associated with the patient-of-interest into the trained model and implementing the trained model. At 2608, based on the predicted egg outcome, the method 2600 may include classifying the patient as a low responder, average responder, or high responder. For example, the predicted egg outcome may be compared with one or more threshold values and/or threshold ranges associated with the low responder class, average responder class, and high responder class. The patient may be classified based at least in part on this comparison.

If at 2610, the method 2600 determines that for the selected stimulation protocol, the patient has been classified as a low responder, then the method 2600 may further include selecting an alternative stimulation protocol (e.g., repeating 2604). The method 2600 may then continue in relation to the alternative stimulation protocol. If however, at 2610, the method 2600 determines that for the selected stimulation protocol, the patient has not been classified as a low responder, then the method 2600 may proceed to prescribing the selected stimulation protocol to the patient (e.g., at 2612).

FSH Dose Model

In some variations, an FSH dose model may be generated/built in order to help an RE make a decision on the amount of FSH dose (e.g., starting FSH dose, average daily FSH dose, total FSH dose, and/or the like) to be prescribed to a patient. For instance, the FSH dose model may predict the egg outcome for varying dose of FSH. Once the FSH model is generated and/or trained, in order to test the model, all other input variables (e.g., measurements of anti-mullerian hormone (AMH) and antral follicle count (AFC)) may be kept constant while varying the FSH dose. The forecasted egg outcome may be compared with the actual egg outcome to validate the model.

Similar to the stimulation protocol model, an FSH dose model may be trained on patient information such as age, race, ethnicity, prior IVF history, prior intrauterine insemination (IUI) history, prior pregnancy or live birth history from natural conception, ultrasound images, and/or baseline measurements such as anti-mullerian hormone (AMH), antral follicle count (AFC). Additionally, the FSH dose model may be trained on the stimulation protocol that was selected (e.g., with the help of the stimulation protocol model).

The selection of an FSH dose may involve a balance. For example, a low dose may not promote follicle growth, while a high dose may overstimulate and lead to detrimental effects on the egg quality and live birth rates. In some variations, the FSH dose model may be a linear regression model or a neural network. The linear regression model or the neural network may be trained on the patient-specific data described above. The linear regression model or the neural network may be implemented and a simulation may be run by varying the FSH dose for a patient. For example, FIG. 7A illustrates the predicted egg outcome for patient 1 and FIG. 7B illustrates the predicted egg outcome for patient 2 for varying levels of FSH dose using a neural network.

Figures 7A, 7B:
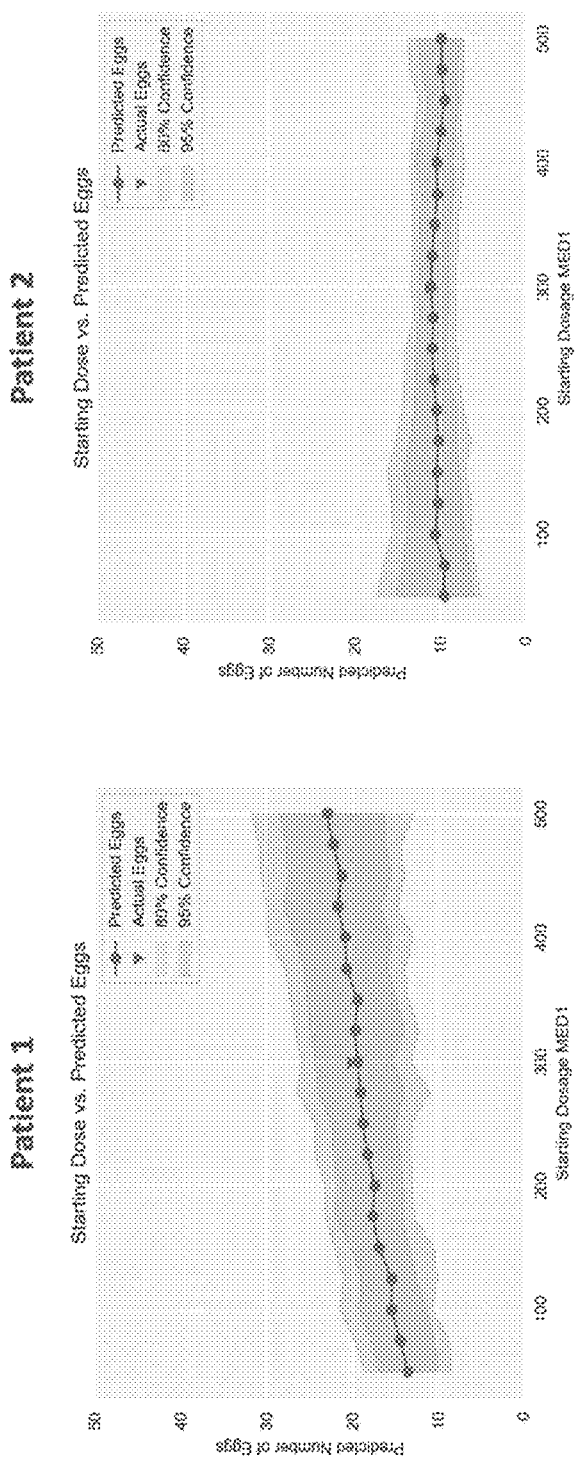
FIG. 7A illustrates the predicted egg outcome for a patient 1 for varying levels of FSH dose.
FIG. 7B illustrates the predicted egg outcome for a patient 2 for varying levels of FSH dose.

As seen in FIG. 7A and in FIG. 7B, the predicted egg outcome and the actual egg outcome are the same for patient 1 and patient 2 when the FSH dose for patient 1 and for patient 2 is 300 international units. FIG. 7A and FIG. 7B also illustrate a confidence interval of 80% and 95% for each prediction point. The simulation may be run by solely varying the FSH dose while keeping other patient-specific data constant.

A challenge to using a linear regression model may be that in some cases, the FSH dose may be negatively correlated to egg outcome. In some cases, the egg outcome may increase as the FSH dose increases. In some scenarios, a specific FSH dose may provide an optimal egg outcome. To address this issue, K-nearest neighbors (KNN) technique may be implemented. KNN may include modeling smaller subsets of patients. For instance, multiple linear regression models may be trained. Each model may be trained with a small subset of patients. To predict the egg outcome for a new patient, the model trained with patients that are similar to the new patient may be implemented. In other examples, the KNN calculates the mean or median number of eggs directly from the smaller subset of similar patients, without using a linear regression model.

A set of most similar patients that are similar to the patient-of-interest (e.g., new patient) may be identified by comparing pair-wise distances in a feature vector space, where a feature vector includes one or more parameters such as age, BMI, race/ethnicity, diagnosis, AFC, AMH, prior history, and/or others. For example, the feature vector may include all of such parameters, or the feature vector may include any suitable subset of such parameters (e.g., age and AFC, or AFC and AMH, etc.). Additionally or alternatively, the parameters in the feature vector may be weighted (e.g., with a respective coefficient) to reflect the importance of each parameter (e.g., a first weight for a first parameter and a second weight for a second parameter, where the first weight is greater than a second weight when the first parameter is more important than the second parameter for establishing patient similarity). After identifying the set of similar patients, the egg outcomes can be calculated for each FSH dose used for that set of similar patients. Accordingly, the egg outcome of the set of most similar patients may help predict the egg outcome for the patient-of-interest.

In some variations, an optimization may be performed to identify the best performing distance metrics (e.g., Euclidean distance, Manhattan distance, and/or the like), neighbor weights (e.g., uniform-weighted, distance-weighted, etc.), and number of neighbors. For example, a KNN model may use the Manhattan distance, 60-80 neighbors, and distance-based weighting.

In some variations, the similarity matching (e.g., matching a set of similar patients to a patient-of interest) may be distance based. Additionally or alternatively, similarity matching may include implementing a combination of heuristics. For example, patients with similar diagnosis may be grouped together with the patient-of-interest. The distance calculation in such a scenario may be performed after the heuristics. In some variations, the KNN model may predict the egg outcome (e.g., number of eggs retrieved, number of mature eggs, etc.) by calculating the weighted average from the set of K neighbors that may be most similar to the patient-of-interest.

Figure 8:
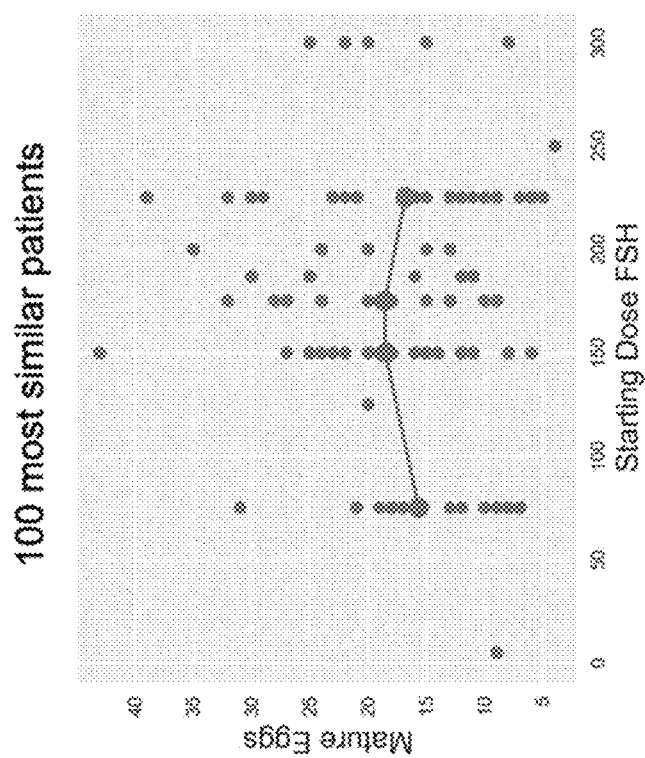
FIG. 8 illustrates the implementation of a similarity model for identifying the optimal baseline FSH dose for a patient in terms of highest egg outcome.

The performance of the KNN model may be evaluated in terms of R-squared ($R^2$) and mean absolute error (MAE). Once the similarity model (e.g., model implementing KNN technique) is generated, the similarity model may be implemented for FSH dose selection by (a) querying the K most similar patients, and then (b) calculating the most commonly-used FSH dose and the most successful FSH dose in terms of highest egg outcome (e.g., number of eggs and mature eggs retrieved). The FSH dose can be the starting dose, average daily dose, total dose, and/or the like. FIG. 8 illustrates the implementation of a similarity model for identifying the optimal FSH dose for a patient in terms of highest egg outcome (e.g., number of mature eggs retrieved). For the patient shown in FIG. 8, the optimal baseline dose may be between 150-200 international units.

In some variations, a similarity model may be generated and implemented to determine whether the patient is an FSH dose-responsive patient (responsive to the dose of FSH in that the patient's egg outcome is predicted to change substantially based on the dose medication given) or an FSH dose non-responsive patient (non-responsive to the dose of FSH in that patient's egg outcome is not predicted to change substantially based on the dose of medication given). For example, the similarity model may determine a set of similar patients (e.g., by implementing KNN matching or other suitable matching techniques). The set of similar patients may be K suitable number of patients such as for example, 10 patients, 25 patients, 50 patients, 75 patients, 90 patients, 100 patients, etc. The K (e.g., suitable number of patients) most similar patients may be queried to determine the number of eggs retrieved for various FSH dosage. A curve may be fitted for the patient for whom the amount of optimal FSH dosage is being identified based on the data (e.g., number of eggs retrieved for various FSH dosage) for the K most similar patients. The curve may then be analyzed to determine whether the patient is an FSH dose-responsive patient or an FSH dose non-responsive patient. For example, if the number of eggs retrieved significantly increases with an increasing FSH dosage based on the curve, the patient may be identified as an FSH dose-responsive patient. However, if the number of eggs retrieved does not significantly vary with increasing FSH dosage based on the curve, the patient may be identified as an FSH dose non-responsive patient. Therefore, the KNN technique may predict the egg outcome for the cases with negative correlation to the baseline FSH dose. The KNN technique may also predict the optimal FSH dose for maximum egg outcome. In some variations, a regression line or polynomial may fit the data to visualize the trend between the dose and the response. In some variations, the regression line may be constrained such that it has a specific shape. For example, when fitting the data, the regression line may be constrained such that the curve has a concave shape downwards. In some variations, multiple curves may be generated for a single patient to relate the response of the patient to one or more kinds of medications. For example, a curve may be fitted to analyze whether the patient is responsive or non-responsive to FSH. Similarly, another curve may be fitted to analyze whether the patient is responsive or non-responsive to LH. In some variations, the curve may be fitted using ratios between different medications and the egg outcome. For example, the curve may be fitted using the ratios between FSH and LH and the egg outcome. In some variations, a three-dimensional response curve may be fitted to simultaneously relate multiple medications to egg outcome.

Figure 20:
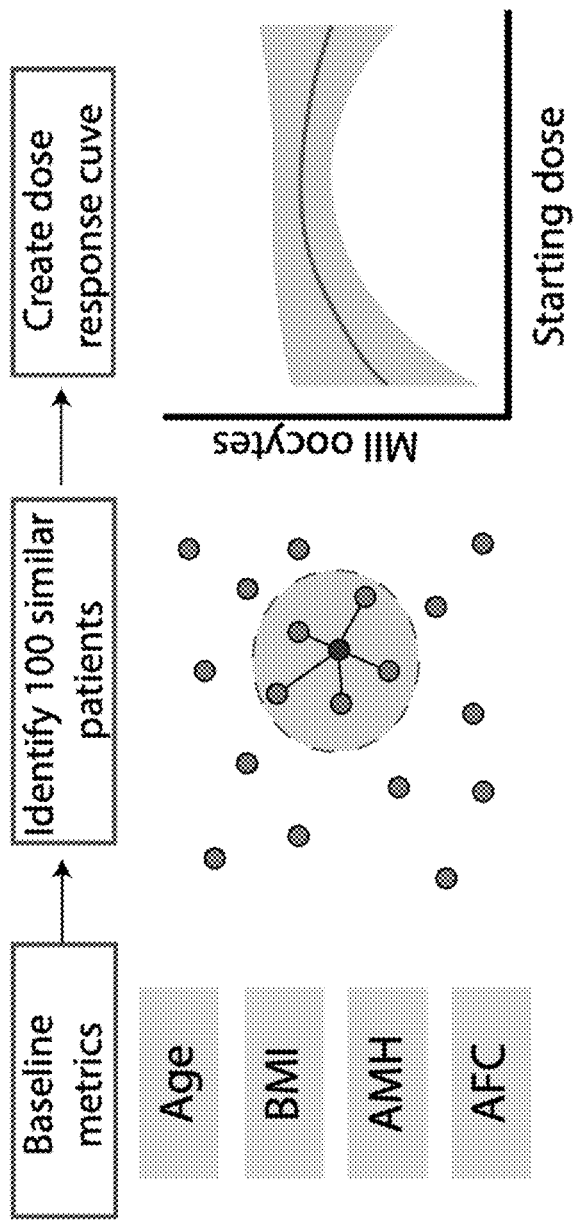
FIG. 20 illustrates generation of an example curve that associates egg outcome with dosage amount to determine whether a patient is dose responsive or dose non-responsive.

FIG. 20 illustrates generation of an example dose-response curve to determine whether a patient is dose responsive or dose non-responsive. A similarity model may be implemented for the patient to identify similar patients. For example, similar patients may be identified by comparing feature vectors that represent metrics such as age, BMI, race/ethnicity, diagnosis, AFC, AMH, prior history, and/or others. As shown in FIG. 20, one hundred (or other suitable number) similar patients may be identified for the patient for whom the curve is to be fitted (e.g., patient-of-interest). A trend line between starting dose and the egg outcome may be fitted for these similar patients, with confidence intervals shown to indicate uncertainty in the prediction. Although FIG. 20 illustrates a trend line between starting dose and oocytes, it should be readily be readily understood that the curve may be fitted for other outcomes such as blastocysts, cumulative live birth, etc. or for other dose variables such as total dose, dose per day, etc.

As discussed above, the similarity model may be implemented to determine whether a patient is dose responsive or whether a patient is dose non-responsive. For example, a patient may be classified as dose responsive or dose non-responsive based on the shape of the fitted curve. In some variations, the model may also recommend an amount of dose (e.g., starting dose, total dose, dose per day, etc.) for a particular patient to the RE. This recommendation may be based on the curve. For example, the curve may be used to identify what amount of dose would lead to maximum egg outcome. Additionally or alternatively, the curve may be used to identify a minimum dose to reach a specific outcome. The patient may be recommended an amount of dose based on these values identified from the curve. The recommendation may be based on whether the patient has been classified as dose responsive or dose non-responsive. For example, if the patient is dose responsive, the patient may be recommended a dose that would maximize the egg outcome. However, if the patient is dose non-responsive, the patient may be recommended a minimum dose (e.g., a low dose) to reach a specific egg outcome so as to reduce patient costs and/or pharmaceutical waste.

FIG. 21A illustrates an example curve 2102 that associates starting dose with egg outcome for a dose responsive patient. The curve 2102 and curve 2104 may be used to identify a recommended dosage for the dose responsive patient and the dose non-responsive patient. As seen in FIG. 21A, for the dose responsive patient, the optimal dose from the curve 2102 is a dosage amount 2106. This is at the peak of the curve 2102 indicating that the egg outcome would be maximum for dosage amount 2106. If the patient were recommended a dosage higher than dosage amount 2016, such as for example dosage amount 2107, the egg outcome would be reduced. Therefore, recommending the patient dosage 2107 would be a non-optimal dose. As such, a dose responsive patient may be recommended a dosage amount 2106 in order to maximize egg outcome.

FIG. 21B illustrates an example curve 2104 that associates starting dose with egg outcome for a dose non-responsive patient. For the dose non-responsive patient, the egg outcome does not change significantly between a low dose such as dosage 2108 and a high dose such as dosage 2110. Put differently, the patient does not respond significantly to changes in the amount of dosage. The slightly optimal dose from curve 2104 is at 2109, but the predicted egg outcome does not significantly increase with increasing dosage beyond dosages 2018 2109. If the patient were recommended a dosage 2110, the egg outcome is predicted to be substantially the same as dosages 2108 and 2109. Therefore, little benefit in terms of egg outcome is expected to be obtained by increasing dosage beyond dosages 2108 and 2109. As such, a recommended treatment for such a patient may include administering the low dosage 2108 to reduce patient costs or pharmaceutical wastage.

In some variations, multiple curves may be generated iteratively to optimize multiple variables. For example, the similarly model may identify a specific desired region of a curve. A secondary curve may be created within the desired region using another variable. For example, within an optimal region of a curve relating starting FSH dosage amount to egg outcome, a secondary curve may be created within that region that relates LH dosage amount to egg outcome.

In some variations, the KNN technique described above may be similarly implemented for stimulation protocol technique (described above).

As discussed above, in some variations, to address the negative correlation to egg outcome, the FSH dose model may be a neural network. The neural network may be trained on the patient-specific data described above. The neural network may be implemented and a simulation may be run by varying the FSH dose for a patient. The confidence intervals for the neural network may be generated by performance inference conducted multiple times with node dropout. One or more nodes may be randomly dropped from the neural network to measure the performance of the neural network so as to generate the confidence intervals.

An RE may look at the egg outcome for varying FSH doses in order to confirm the dose for patients and/or modify the dose for the patient.

Similar to the stimulation protocol, in some variations, if a patient has already undergone an IVF cycle, the RE's initial selection of FSH doses, the patient's response to the FSH doses, and/or modification to the FSH doses may be incorporated into the stimulation protocol selection model. This may provide for a more accurate prediction during subsequent IVF cycles. In some variations, separate prediction models may be generated by incorporating detailed previous IVF history for the patient. Such prediction models may be tailored for the patient and may be comparatively more accurate during the second, third, or later IVF cycle.

Figure 27:
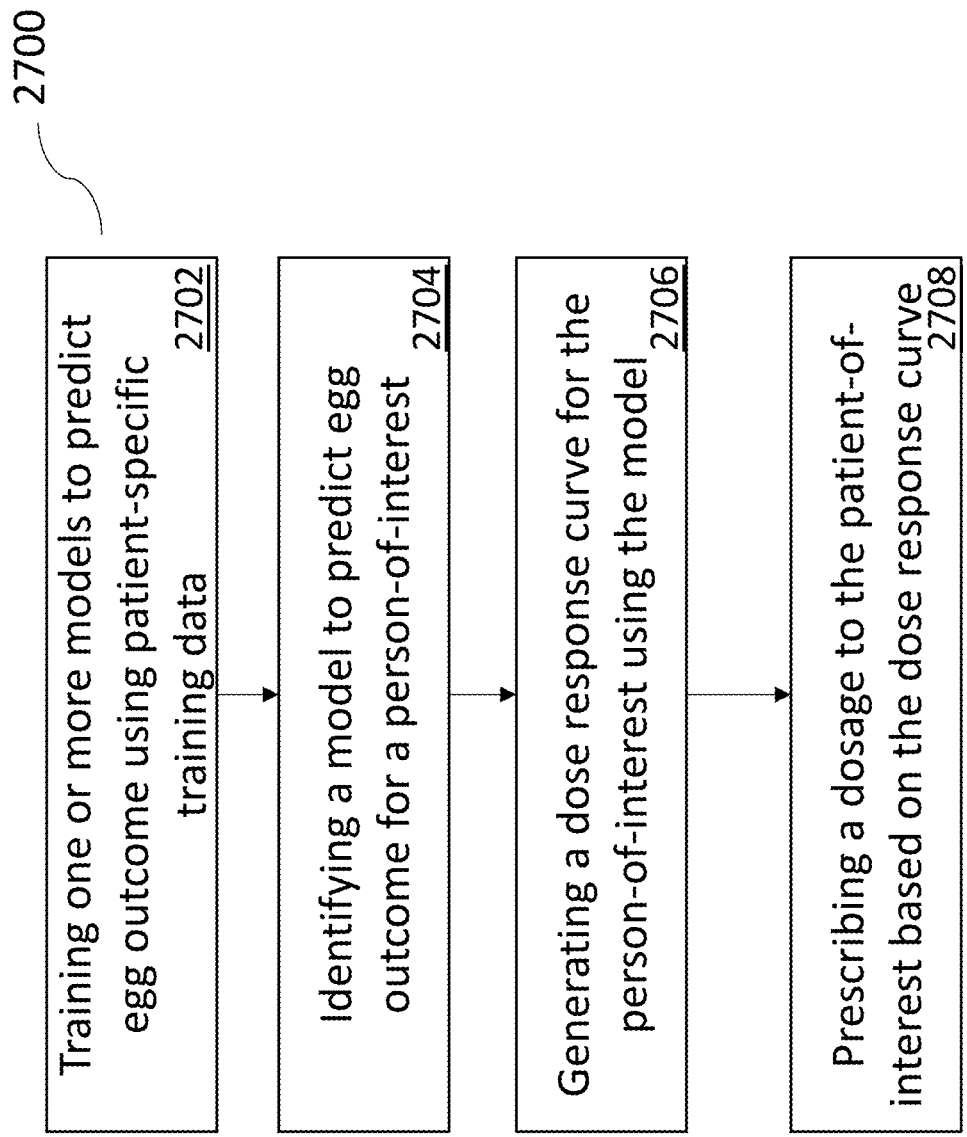
FIG. 27 is a flow diagram illustrating an exemplary variation of a method for prescribing dosage (e.g., an FSH dosage) to a patient-of-interest.

FIG. 27 is a flow diagram illustrating an exemplary variation of a method 2700 for prescribing dosage of a medication in relation to a stimulation protocol (e.g., an FSH dosage) to a patient-of-interest. The method 2700 may include generating subsets of patient-specific training data based on similarity matching, as further described herein. For example, patient-specific training data may include patient information for various patients who may have previously undergone one or more IVF cycles. The patient information may include, for example, information such as age, prior IVF history, prior intrauterine insemination (IUI) history, prior pregnancy or live birth history from natural conception and/or baseline measurements such as anti-mullerian hormone (AMH), antral follicle count (AFC), body mass index, race, ethnicity, ultrasound images, egg outcome for various doses of FSH, egg outcome based on selected stimulation protocol, and/or the like. Similarity matching (e.g., using KNN technique) may be performed to identify subsets of patients from the training data such that each patient within a subset may be similar to other patients within the subset. In this manner, multiple subsets of patient-specific training data may be generated.

At 2702, the method 2700 may include training one or more models using the subsets of patient-specific training data, as further described herein. For example, a first model may be trained using a first subset of patient-specific training data and a second model may be trained using a second subset (different from the first subset) of patient-specific training data. As discussed above, each subset of the patient-specific training data may include patient-specific data of similar patients.

At 2704, the method 2700 may include identifying a model from the one or more trained models for a patient-of-interest. For example, to prescribe medication and/or dosage amounts for a patient-of-interest, the method 2700 may perform similarity matching to identify a model that may be best suited for the patient-of-interest. For instance, the identified model may be a model that may have been trained with a subset of patient-specific training data from patients that may be similar to the patient-of-interest. At 2706, a dose response curve may be generated for the patient-of-interest using the identified model. The dose response curve may help identify whether the patient-of-interest is dose responsive or dose non-responsive. For example, the dose response curve may be fitted for the patient-of-interest based on egg outcome for similar patients (e.g., patients from the subset of patient-specific training data that was used to train the identified model). At 2708, the method 2700 may include prescribing a dosage for the patient-of-interest using the dose response curve that was generated for the patient as described above.

Trigger Day Selection Model

During the course of the ovarian stimulation, a patient may be monitored closely. In some variations, measurements of E2, P4, follicle metrics, such as overall follicle count, overall follicle size, representative metrics of follicle size (e.g., mean, average, median, etc.), respective follicle count for each of a predetermined number of size(s), bins, and/or ranges, etc. for the patient may be recorded. Measurements may, for example, be taken every 2 or 3 days, or in accordance with any suitable schedule (e.g., regular schedule or irregular schedule). As discussed above, one of the clinical decisions that an RE may have to make is a determination of a day on which the final trigger injection may be administered. Administering the final trigger injection too early may not allow smaller follicles to reach maturity, while administering the final trigger injection too late may be detrimental to the maturity of the eggs or may cause follicular atresia.

In some variations, the trigger day selection model may be trained on patient information such as age, race, ethnicity, ultrasound images, prior IVF history, prior intrauterine insemination (IUT) history, prior pregnancy or live birth history from natural conception and/or baseline measurements such as anti-mullerian hormone (AMH), antral follicle count (AFC), and stimulation protocol that was selected. Additionally, the trigger day selection model may be trained on measurements of E2, P4, and/or follicle metrics that may be taken on a regular schedule (e.g., daily, every-other-day, etc.) or on an irregular schedule (e.g., days 5, 7, 9, and 10 of the cycle).

In some variations, the trigger day selection model may be a regression model that incorporates the patient-specific data discussed above. In some variations, if patient-specific data including E2 measurements, P4 measurements, and/or follicle metrics are incorporated for multiple days, then the trigger selection model may be a recurrent neural network, or long-short-term-memory (LSTM) neural network, to better account for changes over time. The trigger day selection model may predict the egg outcome (e.g., number of eggs retrieved and/or number of mature eggs retrieved) for various days. In some variations, the follicle sizes may be grouped into different bins. An example set of bins is shown in Table 2 below, though it should be understood that these are only exemplary in nature, and other suitable follicle size ranges may be grouped to define different suitable sets of bins. Furthermore, although Table 2 indicates a total of six bins, any suitable number of bins may be used (e.g., three, four, five, six, seven, or more than seven bins). For example, in some variations, follicle sizes corresponding to Bin 1 may be omitted from the set listed in Table 2, such that Bins 2-6 are used. As another example, in some variations, follicle sizes corresponding to Bin 6 may be omitted, such that Bins 1-5 are used. As yet another example, in some variations follicle sizes corresponding to Bins 1 and 6 may be omitted, such that Bins 2-5 are used.

TABLE 2

| Bin | Follicle Size |
|---|---|
| 1 | ≤10 mm |
| 2 | 11 mm-13 mm |
| 3 | 14 mm-15 mm |
| 4 | 16 mm-17 mm |
| 5 | 18 mm-19 mm |
| 6 | ≥20 mm |

Additionally or alternatively, the follicle sizes may be grouped as maximum size, minimum size, average size, median size, etc. Grouping into bins may reduce some of the noise or measurement error associated with measurements of the sizes of each individual follicle. Additionally, grouping may provide the added benefit of model interpretability without compromising performance of the model.

For various stimulation days before the final trigger injection is administered, the recorded E2 measurements, P4 measurements, and follicle metrics may be incorporated into the regression model. In some variations, a rate of change of follicle size may be incorporated into the regression model. In scenarios in which the ovarian stimulation continues for an additional couple of days (e.g., additional day or two), growth trends may be determined.

Figures 9A, 9B:
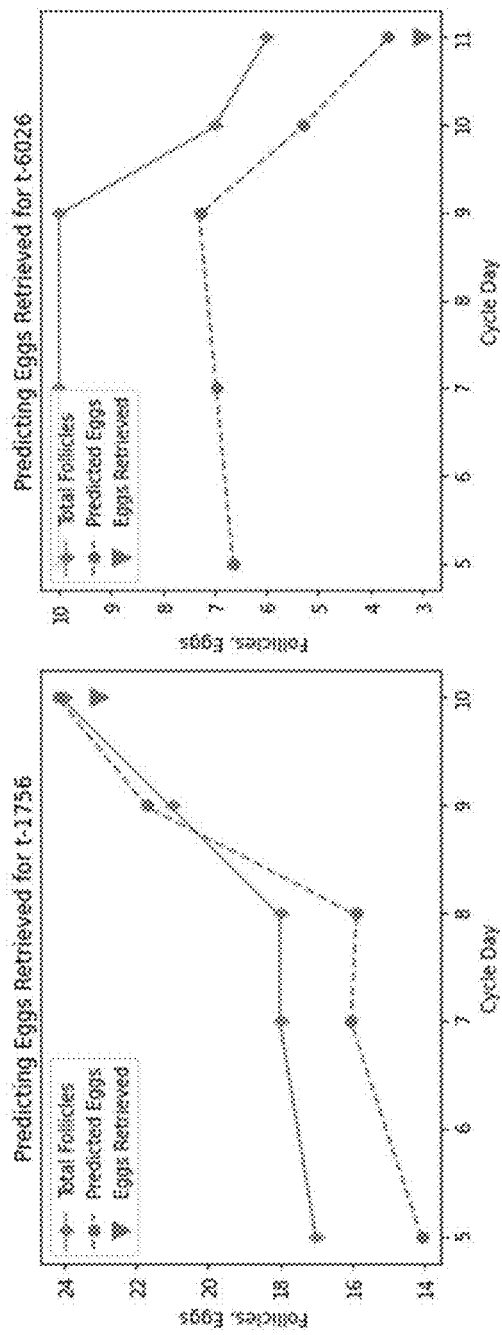
FIG. 9A illustrates the predicted egg outcome for a patient 1 for each day of the cycle.
FIG. 9B illustrates the predicted egg outcome for a patient 2 for each day of the cycle.

When the trigger selection model is deployed, the egg outcome (e.g., number of eggs retrieved, number of mature eggs retrieved, number of successfully fertilized eggs) may be predicted at each day of the stimulation (e.g., days on which blood work and/or ultrasound measurements have been recorded). FIG. 9A and FIG. 9B illustrates the predicted egg outcome for two example patients for each day of the cycle. The shapes of the growth trends may be used to approximately forecast what may happen if the stimulation were to continue for another day or two.

Figure 10:
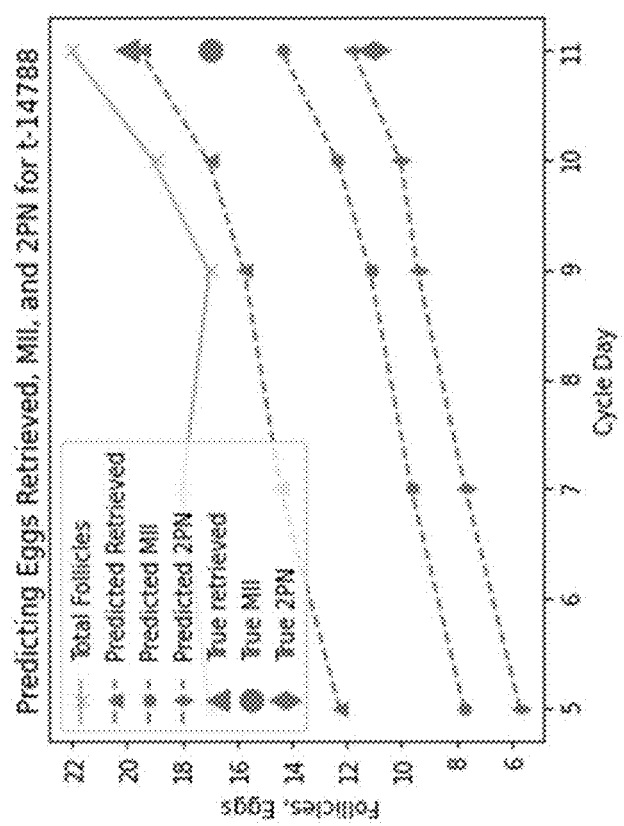
FIG. 10 illustrates various predicted egg outcomes for different cycle days by deploying a multi-output regression model.
Figure 11C:
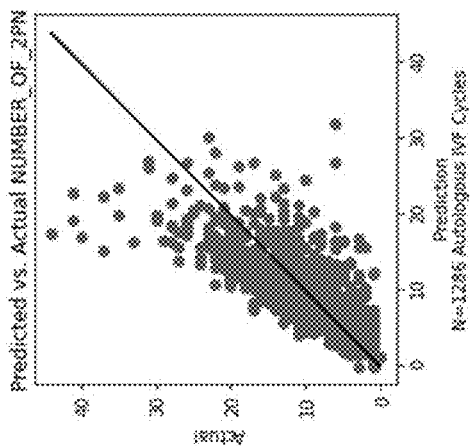
FIG. 11C illustrates predicted egg outcomes for a patient by deploying an independent regression model.
Figure 11B:
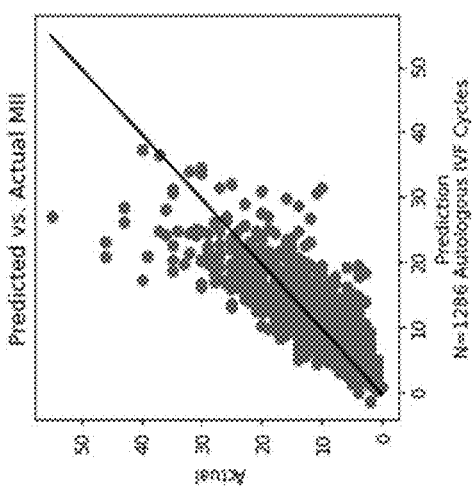
FIG. 11B illustrates predicted egg outcomes for a patient by deploying an independent regression model.
Figure 11A:
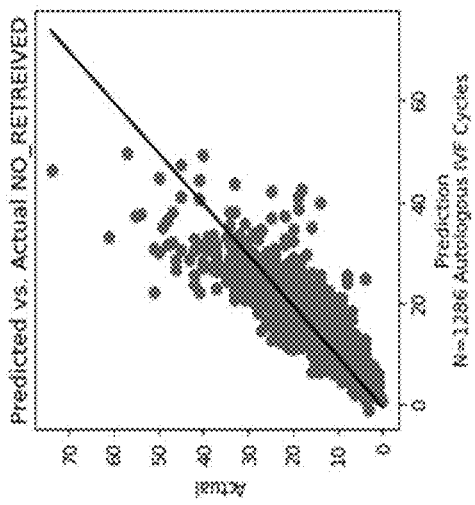
FIG. 11A illustrates predicted egg outcomes for a patient by deploying an independent regression model.

In some variations, the trigger selection model may be a multi-output regression model or may be multiple independent regression models each with a different outcome. For example, the multi-output regression model may predict various egg outcomes such as number of eggs retrieved, number of mature eggs, number of successfully fertilized eggs, etc. The multiple independent regressions models may each predict one of number of eggs retrieved, number of mature eggs, number of successfully fertilized eggs, etc. Therefore, various egg outcomes and their relationships may be captured by deploying the multi-output regression model or the multiple independent regression models. FIG. 10 illustrates various predicted egg outcomes for different cycle days by deploying a multi-output regression model. FIG. 11A, FIG. 11B, and FIG. 11C however, illustrate different egg outcomes by deploying independent multiple regression models.

Figure 12A:
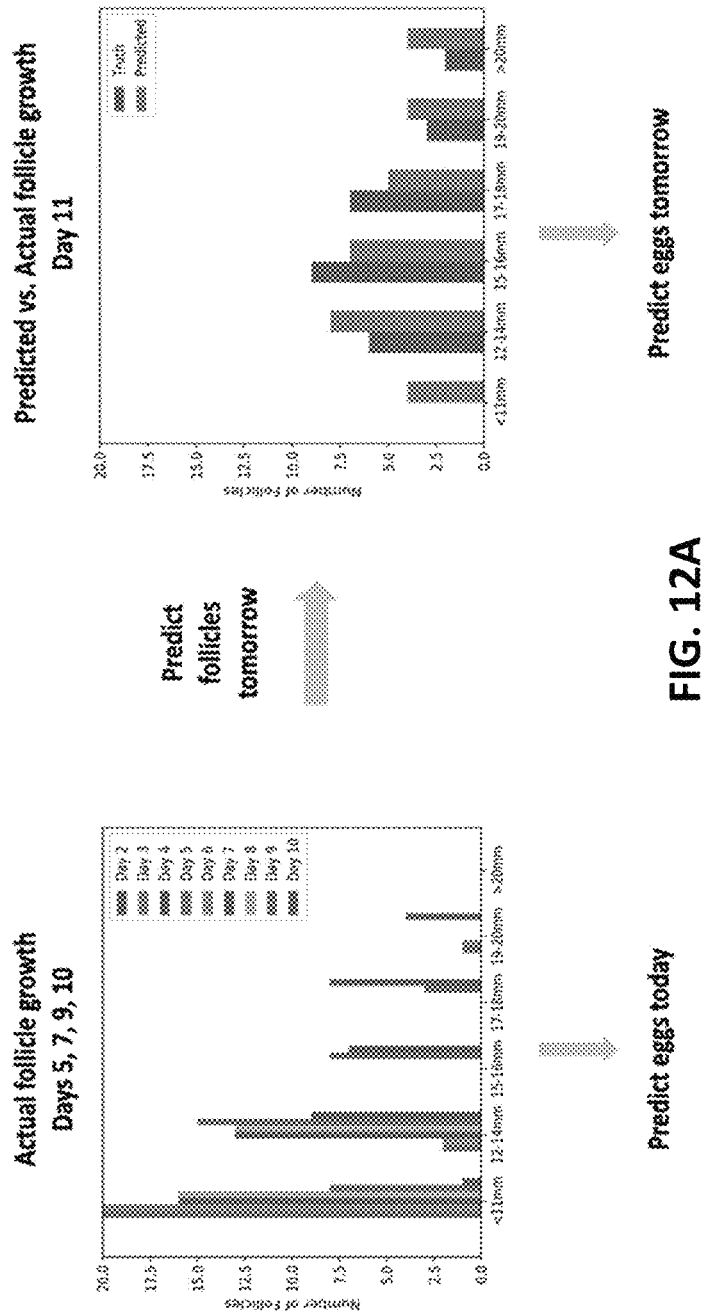
FIG. 12A illustrates a prediction of follicle counts and sizes at a future date by deploying a neural network.

In some variations, the trigger selection model may include a neural network that may forecast E2 measurements, P4 measurements, and follicle metrics one or two days into the future. This helps determine egg outcome (e.g., number of eggs retrieved and/or number of mature eggs retrieved) at those future dates. In some variations, the neural network may be a recurrent neural network, or long-short-term-memory (LSTM) neural network. FIG. 12A illustrates a prediction of egg outcome at a future date (e.g., day 11) for various follicle sizes by deploying the neural network. For example, if the follicle sizes are recorded for days 5, 7, 9, and 10 of an IVF cycle, then the neural network may (1) forecast the predicted follicle size for day 11, and may (2) calculate the predicted egg outcome if the final trigger injection were administered on day 10 compared to on day 11. This may allow for more accurate forecasting. In some variations, if the follicle sizes and the hormone levels are measured only every-other-day or on an irregular schedule, a neural network or a linear model may be trained to interpolate missing data to fill in the days where no measurements were taken. Additionally or alternatively, the missing data may be filled in by carrying forward previous day's values.

In some variations, the trigger selection model may incorporate a combination of techniques. For instance, a recurrent neural network may be used to forecast follicle metrics, as well as E2 and/or P4 values, one day into the future. An interpretable linear regression model may then be used to predict an egg outcome at two time points: (a) using the real current-day measurements of follicle metrics and E2 levels, and (b) using the forecasted next-day measurements of follicle metrics and E2 levels. This allows a comparison for the egg outcome if trigger were to happen in the current day compared to the next day. FIG. 12B illustrates a prediction of egg outcome at a future date using a combination of techniques. In 1252, a patient is predicted to have a higher number of mature eggs if they had waited one more day before triggering. In 1254, a different patient is predicted to have fewer mature eggs if they had waited one more day before triggering.

In some variations, the trigger selection model may include multiple independent regression models predicting the same outcome on different days. For example, a first regression model may predict the egg outcome if the final trigger injection were administered on current day of stimulation while a second regression model may predict the egg outcome if the final trigger injection were administered on the next day of stimulation. The trigger selection model may, for example, include a generalized linear regression model such as a linear regression model, a Poisson regression model, or a negative binomial regression model. In some variations, the input 1846 to a first linear regression model 1848*a* (predicting an egg outcome 1850*a* resulting from the trigger injection being administered on a current day) may include current day follicle metrics and/or E2 levels, while the input 1846 to a second linear regression model 1848*b* (predicting an egg outcome 1850*b* resulting from the trigger injection being administered the next day) may include previous day follicle metrics and/or E2 levels. In other words, to predict the egg outcome if triggering today, a linear regression model may use follicle metric(s) and E2 levels measured on the day of trigger. To predict the egg outcome if triggering tomorrow, a separate linear regression model may use follicle metric(s) and E2 levels measured one day prior to the day of trigger. Furthermore, an E2 forecasting model may predict next-day E2 levels using follicle metric(s) and E2 levels measured one day prior. Together, the combination of these models may permit a comparison of egg outcomes if triggering today vs. tomorrow.

Figure 18:
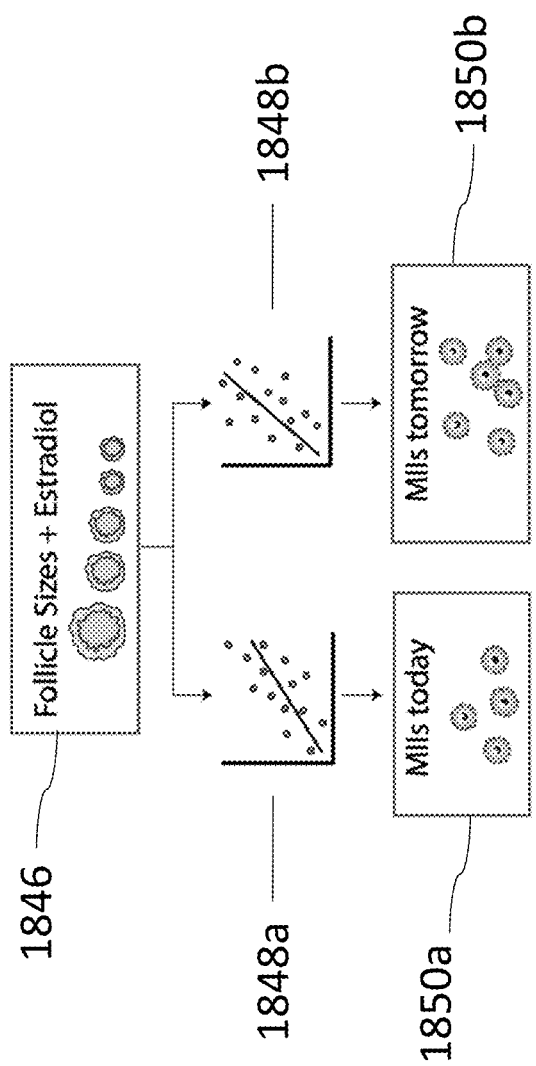
FIG. 18 illustrates prediction of egg outcome on a current day and the next day of stimulation by implementing two independent regression models.

For example, FIG. 18 illustrates prediction of egg outcome on a current day and the next day of stimulation in part by implementing two independent regression models. In FIG. 18, the input 1846 to the independent models 1848*a* and 1848*b* may be follicle metrics and E2. A first linear regression model 1848*a* may be implemented with input 1846 as described above to predict the egg outcome for a current day (e.g., today). As seen in FIG. 18, in this example, the linear regression model 1848*a* may predict the egg outcome 1850*a* for the current day to be four eggs. A second linear regression model 1848*b* may be implemented with input 1846 as described above to predict the egg outcome for the next day. As seen in FIG. 18, in this example, the linear regression model 1848*b* may predict the egg outcome 1850*b* for the next day to be six eggs. As such, the two independent regression models 1848*a* and 1848*b* may predict that the egg outcome may be four eggs if the final trigger injection were to be administered today and that the egg outcome may be six eggs if the final trigger injection were to be administered tomorrow. Accordingly, the trigger selection model may provide a tool to help RE clinical decision-making regarding determining appropriate timing for the final trigger injection.

Figure 19:
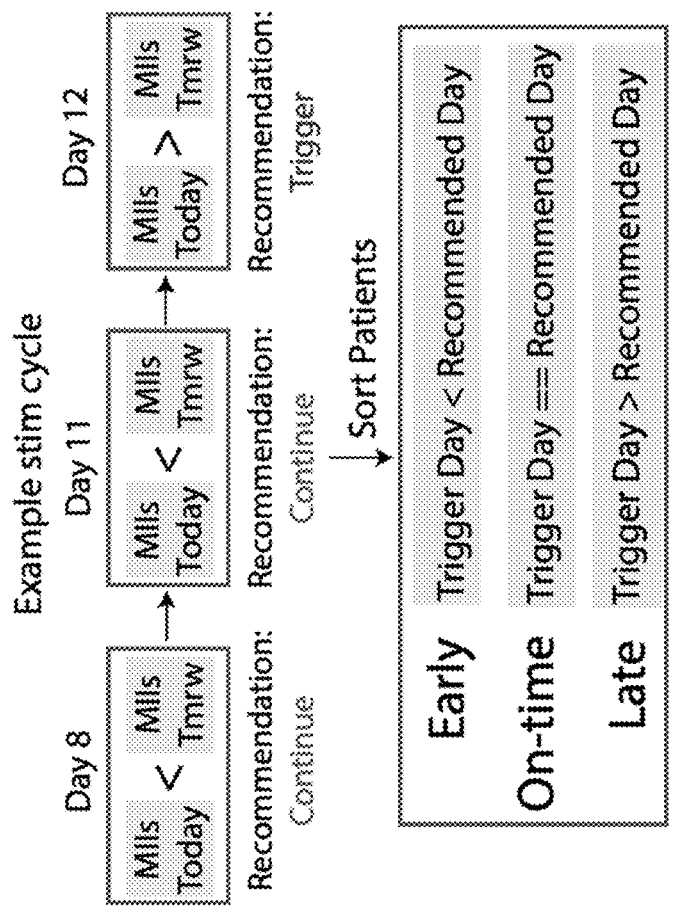
FIG. 19 illustrates recommendations given to an RE based on a trend of predicted egg outcome and classification of a patient after the final trigger injection has been administered.

In some variations, the trigger selection model may make a recommendation to the RE based on egg outcome predictions on consecutive days. For instance, the trigger selection model may predict the egg outcome on consecutive days of the stimulation. Accordingly, the trigger selection model may classify a patient as early, on-time, or late based on whether the final trigger injection was administered to the patient on the day that trigger selection model recommends administering the final trigger injection. This may allow the REs to perform retrospective analysis of the REs decision and the output from the trigger selection model. FIG. 19 illustrates recommendations given to an RE based on a trend of predicted egg outcome and classification of a patient as early, on-time, or late after the final trigger injection has been administered. For example, in FIG. 19, on Day 8, the trigger selection model predicts the egg outcome for Day 8 ("MIIs Today") and Day 9 ("MIIs Tmrw"). Based on the trend of the egg outcome (i.e., fewer eggs on Day 8 in comparison to Day 9), the trigger selection model recommends continuing the stimulation protocol, as of Day 8. Similarly, on Day 11, the trigger selection model predicts the egg outcome for Day 11 ("MIIs Today") and Day 12 ("MIIs Tmrw"), and recommends continuing the stimulation protocol since the predicted egg outcome for Day 11 is lower than the predicted egg outcome for Day 12, as of Day 11. On Day 12, the trigger selection model predicts that the egg outcome on Day 12 ("MIIs Today") would be greater than the egg outcome on Day 13 ("MIIs Tmrw"). Based on this trend where continuing the stimulation protocol beyond Day 12 is predicted to result in reduced egg outcome, the trigger selection model recommends administering the final trigger injection on Day 12. A retrospective analysis of the recommendation and the RE's decision may then be performed. For instance, the patients may be classified as early if the RE decides to administer the actual final trigger injection before the recommended day (e.g., day to administer the final trigger injection as predicted by the trigger selection model). For example, in FIG. 19, if the RE decides to administer the final trigger injection before Day 12, the patient may be classified as early. The patients may be classified as on-time if the RE decides to administer the actual final trigger injection on the same day as the recommended day. For example, in FIG. 19, if the RE decides to administer the final trigger injection on Day 12, the patient may be classified as on-time. The patient may be classified as late if the RE decides to administer the actual final trigger injection after the recommended day. For example, in FIG. 19, if the RE decides to administer the final trigger injection after Day 12, the patient may be classified as late. Similar to the stimulation protocol, in some variations, if a patient has already undergone an IVF cycle, the RE's initial selection of final trigger day may be incorporated into the trigger day selection model. This may provide for a more accurate prediction during subsequent IVF cycles. In some variations, separate prediction models may be generated by incorporating detailed previous IVF history for the patient. Such prediction models may be tailored for the patient and may be comparatively more accurate during the second, third, or later IVF cycle.

Figure 28:
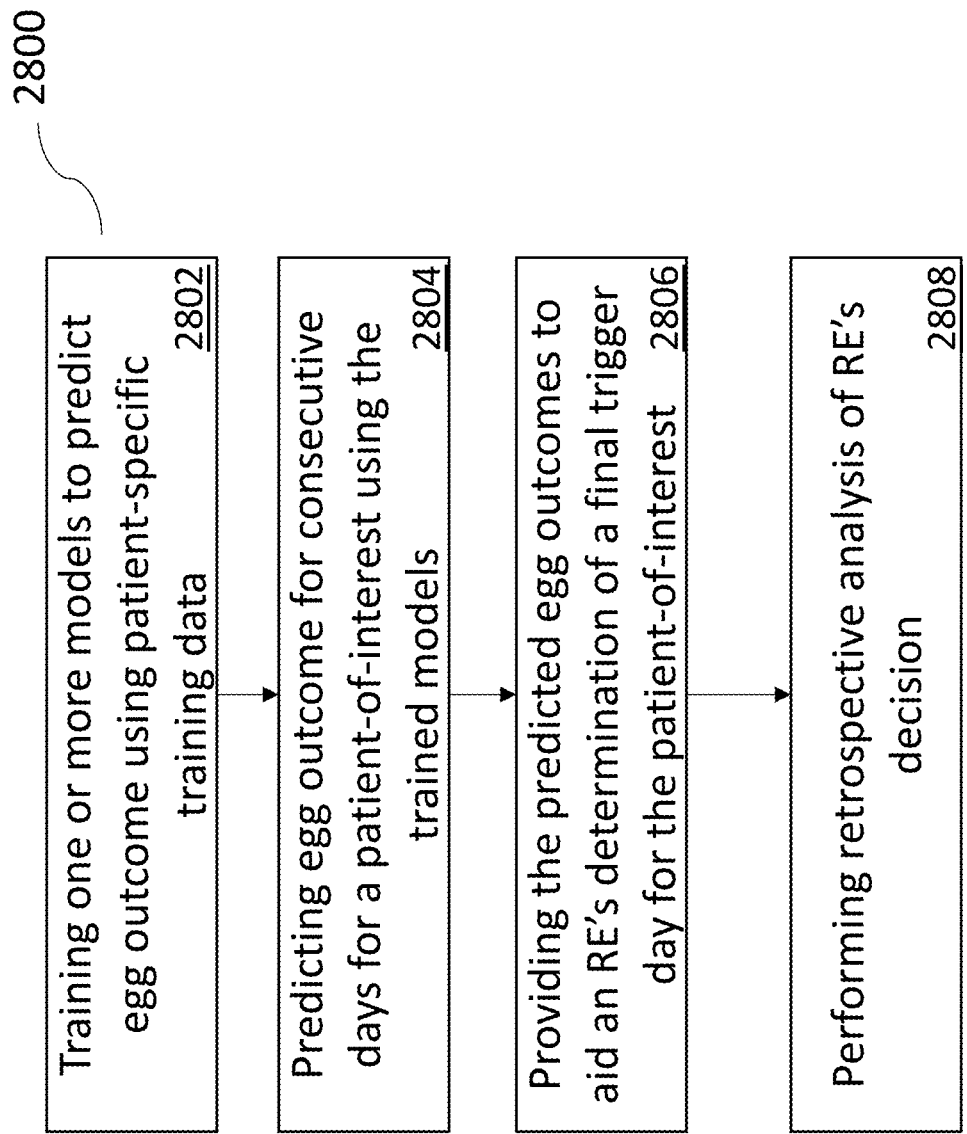
FIG. 28 is a flow diagram illustrating an exemplary variation of a method for aiding an RE's determination of a final trigger selection day for a patient-of-interest.

FIG. 28 is a flow diagram illustrating an exemplary variation of a method 2800 for assisting an RE determining a final trigger selection day for a patient-of-interest. At 2802, the method 2800 may include training one or more models (e.g., one or more linear regression models) to predict egg outcome for a patient using patient-specific training data, as further described herein. The patient-specific training data may include patient information for various patients who may have previously undergone one or more IVF cycles. The patient information may include, for example, information such as age, prior IVF history, prior intrauterine insemination (IUI) history, prior pregnancy or live birth history from natural conception and/or baseline measurements such as anti-mullerian hormone (AMI), antral follicle count (AFC), body mass index, race, ethnicity, ultrasound images, measurements of E2, P4, and/or follicle metrics that may be taken on a regular schedule (e.g., daily, every-other-day, etc.) or on an irregular schedule (e.g., days 5, 7, 9, and 10 of the cycle), and/or the like.

At 2804, the method 2800 may include predicting egg outcome for the patient-of-interest on consecutive days using the one or more trained models, as further described herein. More specifically, the method 2800 may include predicting egg outcome for each day of the consecutive days under the assumption that that particular day would be the day when the final trigger injection may be administered. For example, a first trained regression model may predict egg outcome for day 10 with day 10 as the final trigger selection day, a second trained regression model may predict egg outcome for day 11 with day 11 as the final trigger selection day, a third trained regression model may predict egg outcome for day 12 with day 12 as the final trigger selection day, etc.

At 2806, the method 2800 may include providing to an RE the predicted egg outcomes to aid the RE's determination of a final trigger selection day based on the predicted egg outcome. For example, if based on the predictions, the egg outcome increases from day 10 to day 11 but decreases from day 11 to day 12, the method may provide information to the RE that results in the RE selecting day 11 as the final trigger selection day for the patient-of-interest. At 2808, the method 2800 may also include performing retrospective analysis of the RE's decision in relation to one or more recommended trigger days provided by the model(s). For example, the method 2800 may include classifying the patient-of-interest as early, on-time, or late based on whether the final trigger injection was administered to the patient-of-interest on the day that one or more trained models recommend administering the final trigger injection. If the final trigger injection is administered before the recommended day, the patient-of-interest may be classified as early. In a similar manner, if the final trigger injection is administered after the recommended day, the patient-of-interest may be classified as late. In this manner, a retrospective analysis of the RE's decision may be performed.

Dose Adjustment Model

In some variations, during the ovarian stimulation, dose adjustments may be performed. For instance, increasing the FSH dose and/or the LH dose may increase follicle growth. Similarly, decreasing the FSH dose and/or the LH dose may slow down the dominant follicles allowing the smaller follicles to catch up.

In some variations, the dose adjustment model may be trained on patient information such as age, race, ethnicity, ultrasound images, prior IVF history, prior intrauterine insemination (IUI) history, prior pregnancy or live birth history from natural conception and/or baseline measurements such as anti-mullerian hormone (AMH), antral follicle count (AFC), and stimulation protocol that was selected. Additionally, the dose adjustment model may be trained on daily or every-other-day measurements of E2, P4, and/or follicle metrics. In some variations, the dose adjustment model may be a regression model. In some variations, the dose adjustment model may be a neural network (e.g., recurrent neural network, LSTM, etc.). The dose adjustment model may predict egg outcome for varying levels of FSH and/or LH dosages. The egg outcome may be simulated for varying levels of FSH and/or LH dosages by deploying the dose adjustment model. Based on the egg outcome, a RE may determine whether to increase or decrease the FSH and/or LH doses.

Figure 29:
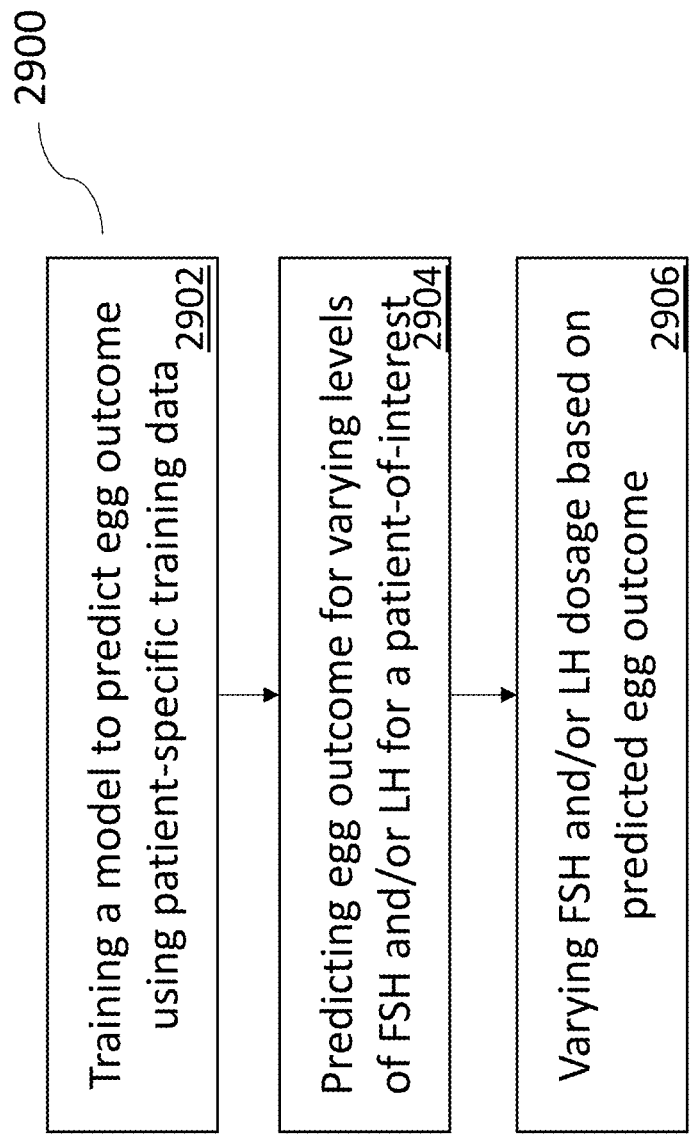
FIG. 29 is a flow diagram illustrating an exemplary variation of a method for varying FSH and/or LH dosage for a patient-of-interest.

FIG. 29 is a flow diagram illustrating an exemplary variation of a method 2900 for varying FSH and/or LH dosage for a patient-of-interest. At 2902, the method 2900 may include a model to predict egg outcome for a patient using patient-specific training data. The patient-specific training data may include patient information for various patients who may have previously undergone one or more IVF cycles. The patient information may include, for example, information such as age, prior IVF history, prior intrauterine insemination (IUI) history, prior pregnancy or live birth history from natural conception and/or baseline measurements such as anti-mullerian hormone (AMR), antral follicle count (AFC), body mass index, race, ethnicity, ultrasound images, measurements of E2, P4, follicle metrics, and/or the like.

At 2904, the method 2900 may include using the model to predict egg outcome for a patient-of-interest for varying levels of FSH and/or LH dosages, as further described herein. At 2906, the method may include recommending whether to increase or decrease the levels of FSH and/or LH dosages based on the predicted egg outcome.

Imputation Model

As discussed above, the models described herein may be trained on patient information (e.g., age, race, ethnicity, ultrasound images, prior IVF history, prior intrauterine insemination (IUI) history, prior pregnancy or live birth history from natural conception and/or baseline measurements such as anti-mullerian hormone (AMH), antral follicle count (AFC), and stimulation protocol that was selected), measurements of E2, P4, and/or follicle metrics. It may be possible that some of the training data includes erroneous data or missing information. For example, consider a patient whose data is to be included for training the models described herein. For example, if the patient was administered the final trigger selection injection on day 7 and the retrospective analysis indicates that the patient was administered the final trigger selection injection on-time. Typically, the follicle size for the patient should either increase from day 5 to day 7 or at least remain the same. However, consider that the training data included an error. That is, the training data erroneously includes decreasing follicle size from day 5 to day 7. If a model were to be trained with this erroneous data, the model may erroneously predict administering the final trigger selection injection on day 5 instead of day 7 based on the trend of the follicle size. Accordingly, the accuracy of the model may be affected with erroneous or missing data.

To address this challenge, an imputation model may be implemented to infer missing or erroneous data. For example, on the current day of stimulation, the integrity of the follicle metrics and/or follicle measurements may be evaluated using one or more of the prior days' follicle measurements, based on the assumption that the follicle measurements are most likely to either stay the same size or grow over time. For example, if the current day is day 7, the follicle measurements for day 7 may be evaluated using the follicle measurements for the preceding day 6, day 5, day 4, day 3, day 2, and day 1. If, based on this evaluation, the follicle measurements for the current day do not seem valid (e.g., the follicle measurements for day 7 are less than that for day 6), an imputation model may be implemented to impute the follicle measurements to ensure that the current day follicle measurements are valid. For example, the imputation model may estimate the values of follicle measurements for the current day based on prior days' measurements. In this manner, the accuracy of the models described herein may be improved. In some variations, the imputation model may include an optimization technique such as linear programming, nonlinear programming, convex optimization, a combination thereof, and/or the like to impute the necessary follicle data. For example, consider that the final trigger day is predicted using the trigger selection day model. As discussed above, the trigger selection day model may group the follicle sizes into different bins based on their sizes. As an example, if the current day is day 7, and the total number of follicles for day 7 is less than the total number of follicles for day 6, then this might be an indication that the total number of follicles for day 7 may not be valid. Accordingly, linear programming may be applied to determine the minimum number of follicles to be added to each follicle bin such that the number of follicles for each follicle bin increases and/or remains the same from day 6 to day 7. In this manner, imputed follicle measurements may be determined for day 7. On day 8, this process may be repeated using the imputed follicle measurements from day 7.

Safety Model

Sometimes, there may be risks associated with ovarian stimulation. For example, some patients may experience complications such as ovarian hyperstimulation syndrome (OHSS), an exaggerated response to the follicle stimulating hormones that may cause the ovaries to swell and become painful. Such complications may lead to cancelation of the stimulation cycle and may negatively affect future IVF cycles. To mitigate the complications associated with OHSS, patients who are at risk of OHSS may be prescribed a specific stimulation protocol that may lower the risk of an adverse response due to OHSS. A safety model may be implemented to prescribe a stimulation protocol for patients at risk of OHSS.

In some variations, the safety model may be trained on patient information such as age, race, ethnicity, ultrasound images, prior IVF history, prior intrauterine insemination (IUI) history, prior pregnancy or live birth history from natural conception and/or baseline measurements such as anti-mullerian hormone (AMH), antral follicle count (AFC), and stimulation protocol that was selected. Additionally, the safety model may be trained on daily or every-other-day measurements of E2, P4, and/or follicle metrics.

In some variations, the safety model may be a regression model (e.g., linear regression model). In some variations, the safety model may be a neural network (e.g., recurrent neural network, LSTM, etc.). The safety model may identify patients at risk of OHSS and may recommend a treatment plan to minimize the risk of complications. To identify patients at risk of OHSS, the safety model may use day-to-day measurements of E2, P4, and/or follicle metrics to predict whether the patient is at risk of OHSS. More specifically, if measurements of E2, P4, and/or follicle metrics exceed a threshold value and/or fall outside a normal range, it may be indicative of the patient being at risk of OHSS. The threshold value and/or the normal range may be patient specific. That is, different patients may have different threshold values and/or range that may be associated with OHSS.

Therefore, monitoring the day-to-day measurements of E2, P4, and/or follicle metrics to ensure that these measurements do not exceed a threshold value or fall outside a normal range may mitigate the risk of OHSS. The safety model may use these day-to-day measurements for a current day to predict the measurements of E2, P4, and/or follicle metrics for the next day. The predicted measurements for the next day may be analyzed to determine whether the measurements exceed the threshold value or fall outside the normal range. If the predicted measurements for the next day indicate that the measurement may fall outside the normal range, then the patient may be classified as at risk of OHSS. The stimulation protocol for such a patient may then be adjusted to mitigate the risk of OHSS.

Figure 30:
FIG. 30 is a flow diagram illustrating an exemplary variation of a method for classifying a patient-of-interest as at risk of ovarian hyperstimulation syndrome (OHSS).

FIG. 30 is a flow diagram illustrating an exemplary variation of a method 3000 for classifying a patient-of-interest as at risk of ovarian hyperstimulation syndrome (OHSS). At 3002, the method 3000 may include a model to predict egg outcome for a patient using patient-specific training data. The patient-specific training data may include, for example, patient information for various patients who may have previously undergone one or more IVF cycles. The patient information may include information such as age, prior IVF history, prior intrauterine insemination (IUI) history, prior pregnancy or live birth history from natural conception and/or baseline measurements such as anti-mullerian hormone (AMH), antral follicle count (AFC), body mass index, race, ethnicity, ultrasound images, measurements of E2, P4, follicle metrics, and/or the like.

At 3004, the method 3000 may include using the model and measurements of E2, P4, and/or follicle metrics for present day to predict measurements of E2, P4, and/or follicle metrics for the next day for a patient-of-interest, as further described herein. At 3006, the method 3000 may include comparing the predicted measurements of E2, P4, and/or follicle metrics to a predetermined threshold value and/or threshold range. In response to determining that the predicted measurements of E2, P4, and/or follicle metrics for the patient-of-interest exceeds the threshold value, the method may include classifying the patient as at risk of OHSS.

Clinic Workflow Model

IVF clinics are sometimes faced with challenges of coordinating many patient visits within a finite schedule and among a finite number of REs. Balancing a clinic's patient throughput to ensure workload is evenly distributed may require determining the proper time to start patient cycles. For example, if multiple patients working a specific RE start their stimulation protocol cycle at the same time, it may be possible that the RE may be overloaded with multiple egg retrievals on a single day or the embryologists may be overloaded with embryo biopsies on a single day. Accordingly, it may be important to predict the expected trigger day and expected cycle length for a group of incoming patients to help forecast the load of retrievals and/or biopsies, or to identify a start day for the stimulation cycle for each of these patients in order to spread out (e.g., stagger) the expected trigger days, expected egg retrieval days, and/or expected embryo biopsy days for the incoming patients. The clinic workflow model may predict the expected trigger day and the expected cycle for a group of patients.

In some variations, the clinic workflow model may be trained on patient information such as age, race, ethnicity, ultrasound images, prior IVF history, prior intrauterine insemination (IUI) history, prior pregnancy or live birth history from natural conception and/or baseline measurements such as anti-mullerian hormone (AMH), antral follicle count (AFC), and stimulation protocol that was selected. Additionally, the clinic workflow model may be trained on daily or every-other-day measurements of E2, P4, and/or follicle metrics.

In some variations, the clinic workflow model may be a regression model (e.g., linear regression model, or Poisson regression model). In some variations, the clinic workflow model may be a neural network (e.g., recurrent neural network, LSTM, etc.). For a group of patients, based on each patient's expected trigger day and expected trigger cycle, the clinic workflow model may predict a start day for each patient. In some variations, the clinic workflow model may additionally or alternatively predict necessary days for clinic visits for each patient so as to reduce the overall number of patient visits. In some variations, the clinic workflow model may prioritize the order in which the patients should meet the RE to indicate patients that may be in need for most attention. For example, patients that may need to be administered the final trigger injection urgently to avoid a reduction of egg outcome on subsequent days may be prioritized over patients that may not need to be triggered urgently. In some variations, the clinic workflow model may include an optimization technique (e.g., linear programming, convex optimization, a combination thereof, and/or the like) to schedule start dates for a group of patients after predicting the expected trigger day and expected trigger cycle for each patient.

The clinic workflow model may additionally or alternatively be used to assist with staffing within a clinic. For example, in some variations, since it can predict egg retrieval dates and/or embryo biopsy dates for a group of patients associated with a clinic, a clinic workflow model for that clinic may be used predict staffing needs for a particular day's egg retrieval and/or embryo biopsy procedures, thereby allowing a clinic to appropriately schedule staff to perform the expected procedures.

Displaying Predictions Based on the Models

Figure 22A:
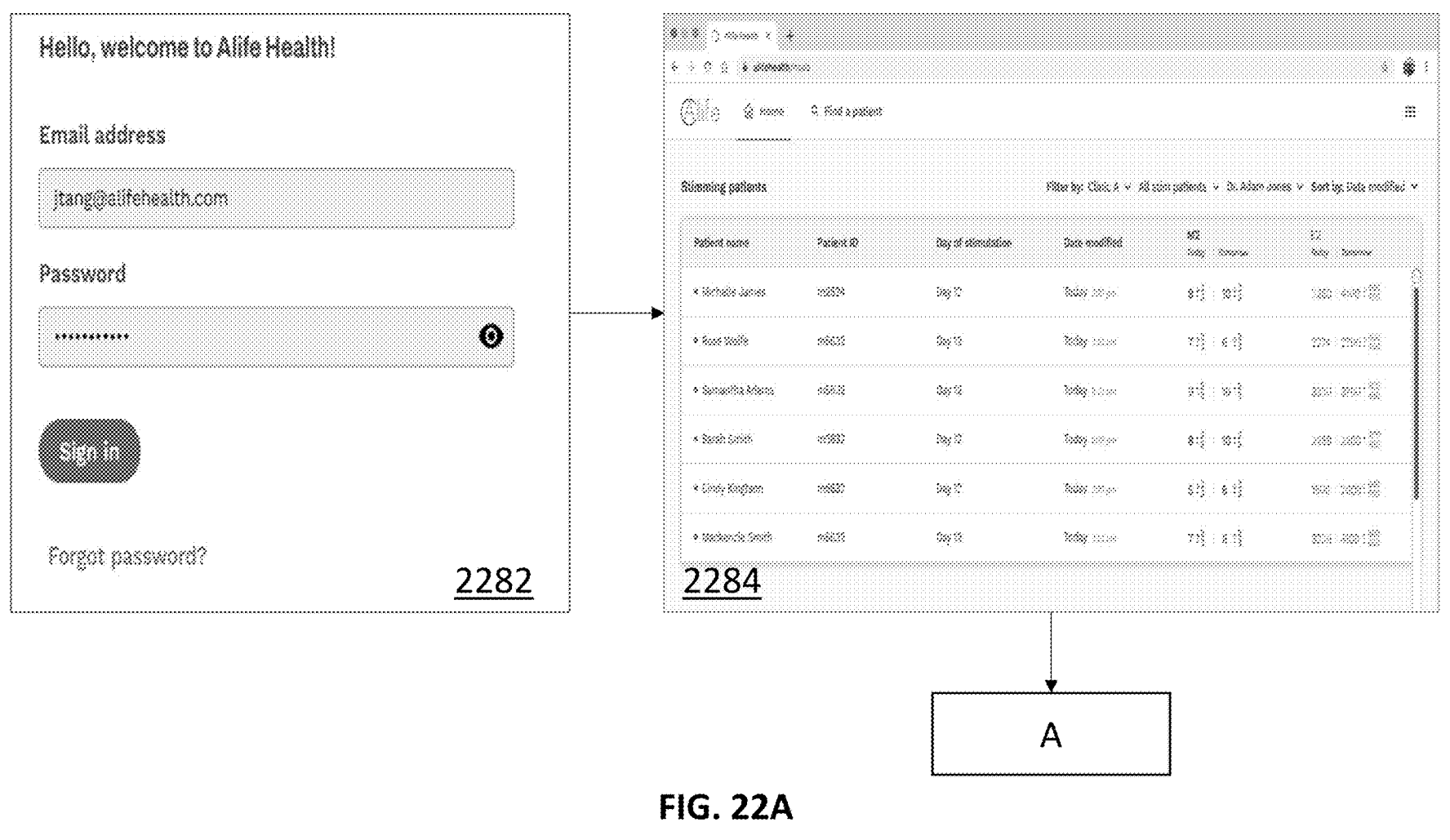
Figure 22B:
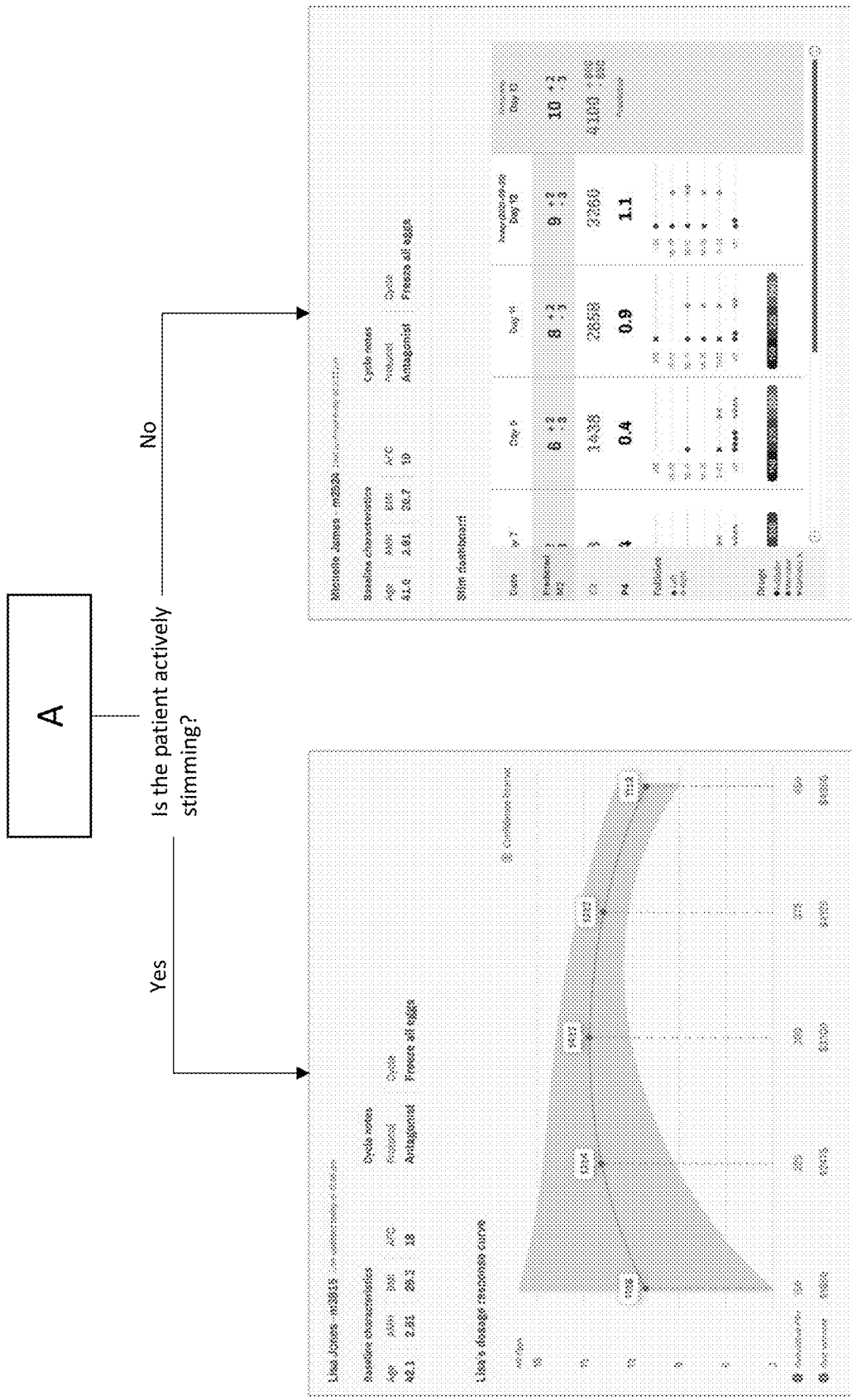

As discussed above, the technology described herein may be used by REs to augment or further inform their decisions. The models disclosed herein may provide interpretable results that the REs may view to inform their decisions. The predictions from the models may be transmitted in an interpretable form to an RE Application (e.g., RE Application 208) being implemented on a suitable computing device. As shown in FIG. 22, at 2282, when the RE Application is implemented, a login page may be displayed on a display of a suitable computing device. Users (e.g., REs, clinicians, etc.) that may be registered on the RE Application may have access to the results from the models and the data associated with the patients. Unregistered users may not have access to the RE Application, thereby providing restrictive access to the results and data associated with the RE Application. This keeps the data and results associated with the RE Application secure. In the login page, a registered RE may entered their registered email address and password such that the RE Application can authenticate the user.

Once the RE Application authenticates the RE, at 2284, the display displays a patient dashboard. FIG. 23 illustrates an example patient dashboard 2384 displayed on a display of a suitable computing device. The patient dashboard 2384 may include a list of the RE's patients. For example, the patient dashboard may include patient name, patient ID, stimulation status, and an updated timestamp (e.g., 2391). As discussed herein, the RE Application may interface with an EMR database (e.g., EMR 204). The patient name and the associated patient ID (e.g., 2292) may be populated from the EMR database. For example, in FIG. 23, "Lisa Jones" may be associated with patient ID "m3815" which may be populated from the EMR database.

The EMR database may also populate the stimulation status 2294 associated with the patient. For instance, the stimulation status may indicate whether the patient's stimulation protocol has begun. For example, in FIG. 23, "Lisa Jones" is shown to have a stimulation status "Pre stim" indicating the stimulation protocol has not begun. If the stimulation status indicates a day number, this may indicate that the stimulation protocol has begun for the patient and that the stimulation process is at the day shown on the display. For example, in FIG. 23, "Rose Wolfe" is shown to have a stimulation status "Day 12" indicating that Rose Wolfe's stimulation has begun and that the current day of the cycle is day 12 of the cycle. For patients actively undergoing stimulation, the patient dashboard 2384 may provide a preview 2396 of some predictions. For example, the patient dashboard 2384 may display the egg outcome (e.g., mature oocytes) predicted for today and for the next day. For instance, in FIG. 23, the mature oocytes predicted for "Rose Wolfe" actively undergoing stimulation (e.g., stimulation status shown as "Day 12") for today is "8.9" and the mature oocytes for tomorrow is "10.2." In some variations, the patient dashboard may also display the E2 measurements for today and the E2 measurement prediction for tomorrow. For example, the E2 measurements for "Rose Wolfe" for today is shown to be "3260" and the E2 measurements predicted for tomorrow is shown to be "4100." The patient dashboard 2384 may also include a filter 2398. For example, the patient list may be filterable by clinic, stimulation status, and by RE.

Figure 24:
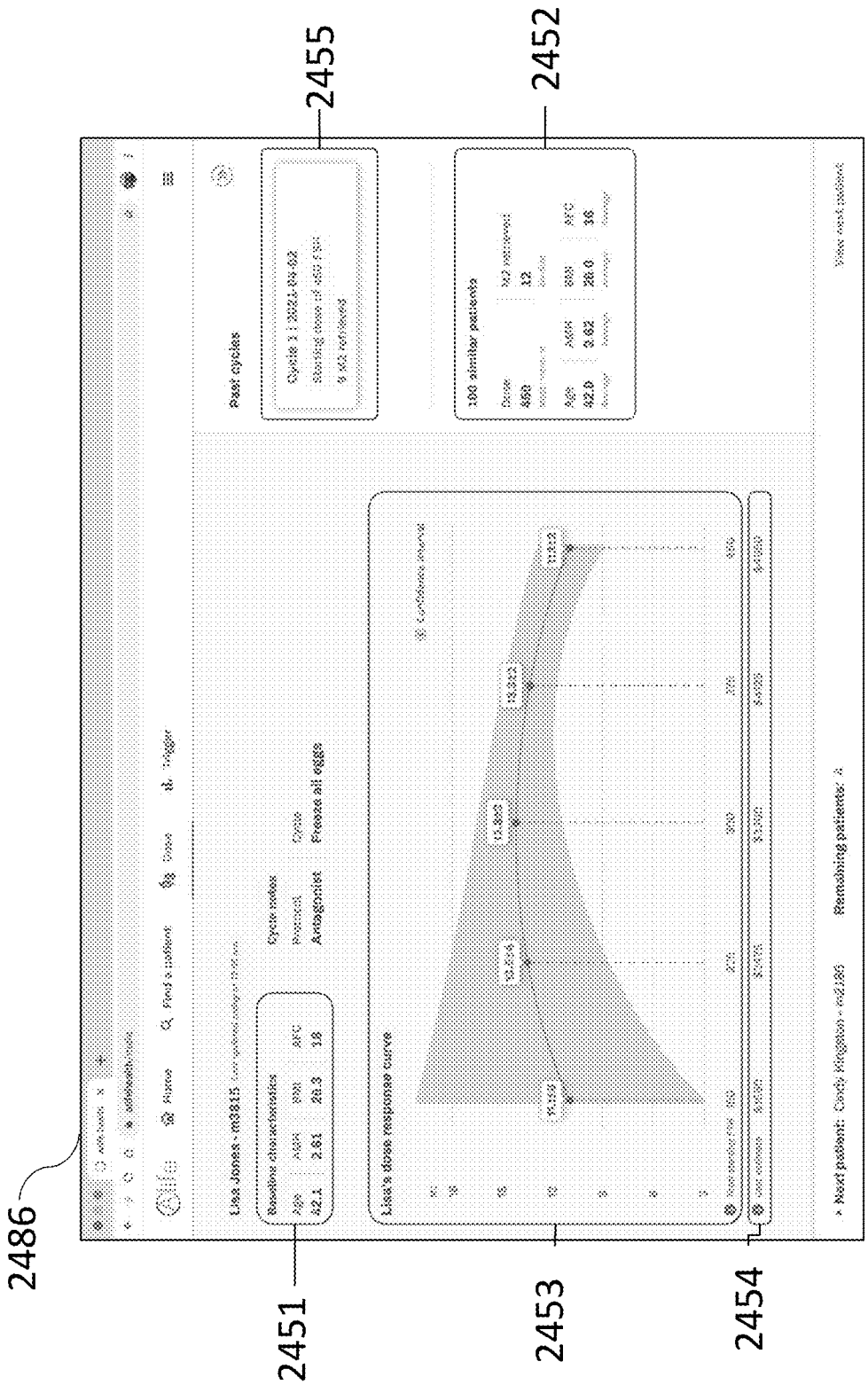
FIG. 24 illustrates an example starting dose page displayed on a display of a suitable computing device.

Referring back to FIG. 22, if the patient is not actively undergoing stimulation (e.g., stimulation status at 2284 is "Pre stim"), then the RE Application at 2286 displays a starting dose page. FIG. 24 illustrates an example starting dose page displayed on a display of a suitable computing device. For example, in FIG. 23, "Lisa Jones" was shown to not be actively undergoing stimulation (e.g., stimulation status at 2284 is "Pre stim"). FIG. 24 shows the starting dose page for "Lisa Jones." The starting dose page 2486 displays the patient's baseline characteristics (e.g., 2451). For example, the starting dose page 2486 shows age, BMI, anti-mullerian hormone (AMH), and measurements of antral follicle count (AFC)) associated with "Lisa Jones." These baseline characteristics may be inputs to the FSH dose model as discussed above.

As discussed herein, the FSH dose model may include a similarity model that identifies patients that are similar to the patient-of-interest. The dose response curve (e.g., the curve fitted using the data of the similar patients) may indicate whether the patient-of-interest is dose responsive or dose non-responsive. In FIG. 24, the statistics of the patients that are similar to "Lisa Jones" may be displayed (e.g., 2452). As shown in FIG. 24, the FSH dose model may use historical patient cycle data of 100 similar patients. The statistics of these similar 100 patients is shown in 2452. The dose response curve may be fitted/generated for "Lisa Jones" based on these statistics 2452. More specifically, the FSH dose response model may use the baseline characteristics 2451 for "Lisa Jones" and the statistics 2452 of the 100 similar patients to generate the dose response curve 2453. The dose response curve 2453 may depict the egg outcome (e.g., number of mature oocytes) for various starting doses of FSH for "Lisa Jones." The shaded region in the dose response curve 2453 may depict the confidence interval at each dose increment. As seen in FIG. 24, the optimal starting dose for "Lisa Jones" is "300." Additionally, the starting dose page 2486 may also display the cost estimates 2454 for different starting doses that may be projected through a eleven day stimulation cycle. In FIG. 24, the cost estimate for "Lisa Jones" for a starting FSH dose of "300" is "$3300."

In some variations, the starting dose page 2486 may also display whether the patient has had a past cycle (e.g., 2455). Clicking on the past cycle may trigger a summary page for that past cycle of the patient.

Figure 25:
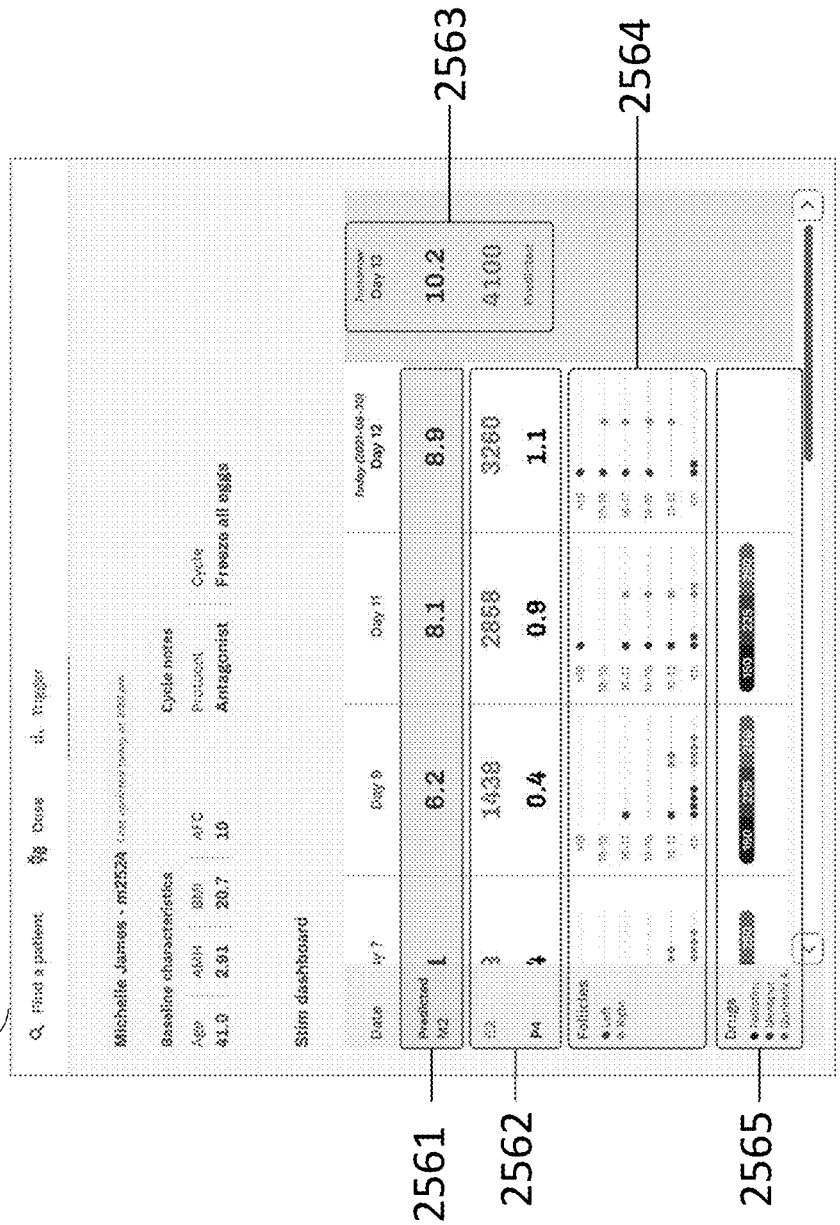
FIG. 25 illustrates an example trigger page displayed on a display of a suitable computing device.

Referring back to FIG. 22, if the patient is actively undergoing stimulation (e.g., stimulation status at 2284 is a day such as "Day 12"), then the RE Application at 2288 displays a trigger page. FIG. 25 illustrates an example trigger page displayed on a display of a suitable computing device. For example, in FIG. 23, "Michelle James" was shown to actively undergo stimulation (e.g., stimulation status at 2284 is "Day 12"). FIG. 25 shows the trigger page 2588 for "Michelle James." The trigger page 2588 includes the baseline characteristics such as age, BMI, anti-mullerian hormone (AMH), and measurements of antral follicle count (AFC)) associated with "Michelle James." These baseline characteristics may be inputs to the trigger selection model as discussed above. The trigger page 2588 enables REs to select the optimal day to administer the final trigger injection to maximize the egg outcome (e.g., mature oocyte yield). For example, the trigger page 2588 provides egg outcome predictions for different trigger days. In FIG. 25, "Michelle James" is shown to be on day 12 of the stimulation protocol. The egg outcome for day 7, day 9, day 11, and day 12 (e.g., 2561) are shown on the trigger page 2588. The trigger page 2588 also shows the E2 and P4 measurements for each of the different trigger days (e.g., 2562). Additionally, the trigger page also includes the egg outcome prediction and E2 measurements for the next day (e.g., 2563). In FIG. 25, since the current day is day 12, the predictions of egg outcome and E3 measurements for day 13 are shown. The trigger page 2588 also provides a visual display of follicle measurements (e.g., 2564) for the different trigger days and the drugs administered on each of the different trigger days (e.g., 2565).

Exemplary Method of Treatment

Figure 13:
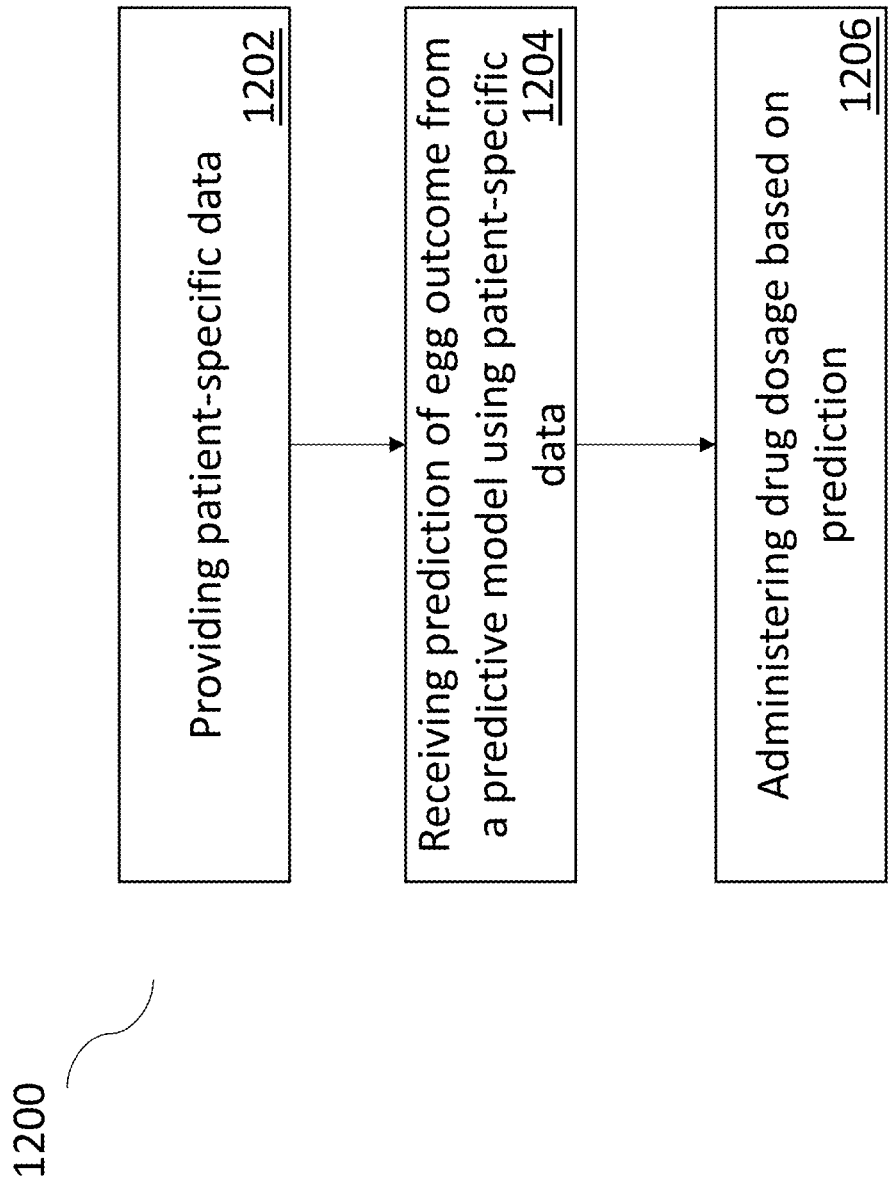
FIG. 13 is a flow diagram of an exemplary method of treatment using the machine-learning model(s) described herein.

FIG. 13 is a flow diagram of an exemplary method of treatment using the machine-learning model(s) described herein. The method 1200 includes providing patient-specific data to a controller (e.g., controller 206 in FIG. 2). The patient-specific data may include patient information, data relating to prior IVF cycles and/or treatments, baseline measurements, treatment variable, response to stimulation protocol, a combination thereof, and/or the like. The controller may generate one or more machine-learning model(s) to predict egg outcome for a patient, such as that described above.

At 1204, the method includes receiving egg outcome from the machine-learning models using the patient specific data. For instance, the method may include receiving egg outcome from a first predictive model relating to a stimulation protocol selection. Additionally or alternatively, the method may include receiving egg outcome from a second predictive model relating to FSH dose model. Additionally or alternatively, the method may include receiving egg outcome from a third predictive model relating to trigger day selection model.

The egg outcome may be predicted by varying one or more of the patient-specific data. For instance, the first predictive model may include K-nearest neighbors (KNN) technique. The first predictive model may predict the stimulation protocol that may provide optimal egg outcome. Similarly, the second predictive model may include K-nearest neighbors (KNN) technique. The second predictive model may predict the FSH dose that may provide optimal egg outcome. In some variations, the third predictive model include a combination of techniques. For instance, a recurrent neural network may be used to forecast follicle metrics, as well as E2 and/or P4 values, one day into the future. An interpretable linear regression model may then be used to predict an egg outcome.

At 1206, the method may include administering drug dosage to a patient based on egg outcome. For instance, a stimulation protocol may be selected for the patient by implementing the first predictive model. The selected stimulation protocol may include amount of drug dosage to be administered to the patient on a day-to-day basis. Additionally or alternatively, the amount of baseline FSH dose may be selected for the patient by implementing the second predictive model. Additionally or alternatively, the day on which the final trigger injection is to be administered for the patient may be selected by implementing the third predictive model.

In some variations, administering the drug dosage may further include monitoring the response of the patient. For instance, the response of the patient to the selected stimulation protocol may be monitored. Based on the patient response, the stimulation protocol may be modified and/or canceled. For instance, if the patient shows low response to a selected stimulation protocol, the first predictive model may be updated to account for the low response. The selected stimulation protocol may be modified based on the updated predictive model.

EXAMPLES

As discussed above, several variables (e.g., amount of FSH dosage, trigger day, stimulation protocol, etc.) may be predictive of egg outcome for a patient. Some non-limiting examples of these variables may include patient's personal information such as age, BMI, etc., patient's past IVF cycle information such as number of cycles, stimulation protocol, diagnosis, etc., baseline dose measurements such as of measurements of estradiol (E2), measurements of luteinizing hormone (LH), measurements of progesterone (P4), measurements of follicle stimulating hormone (FSH), measurements of anti-mullerian hormone (AMH), and measurements of antral follicle count (AFC), etc., stimulation protocol such as follicle sizes, etc., day of trigger, a combination thereof, and/or the like.

Figures 14A, 14B:
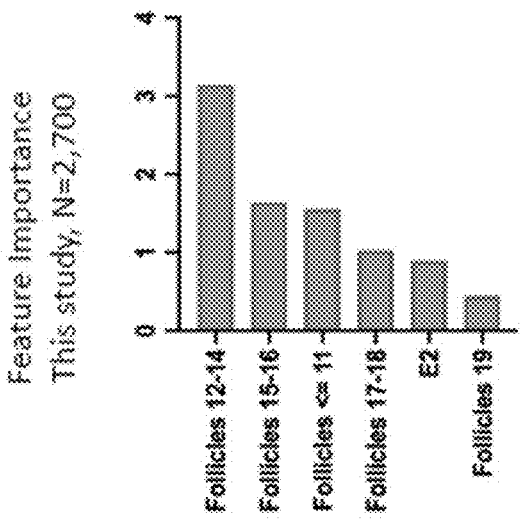
FIGS. 14A-14C illustrate an example of statistically significant variables that may be predictive of the egg outcome for a patient.
Figure 14C:
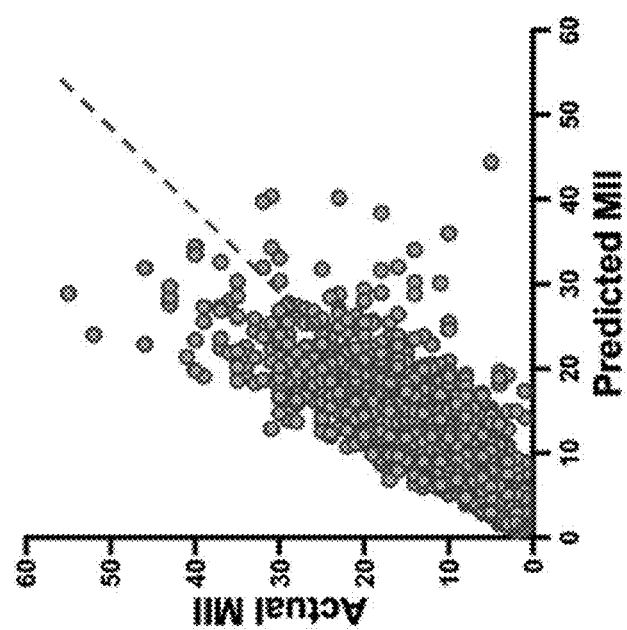

In some variations, it may be possible to identify the most indicative parameters and/or the most statistically significant parameters/variables that may be predictive of the egg outcome for a patient. For example, the most significant variables may be identified by applying recursive feature elimination, where weaker features are identified and removed from the group of candidate features one at a time. FIGS. 14A-14C illustrate an example of most statistically significant variables that may be predictive of the egg outcome for a patient. As seen in FIGS. 14A and 14B, follicle sizes less than or equal to about 11 mm, follicle sizes about 12 mm-about 14 mm, follicle sizes about 15 mm-about 16 mm, follicle sizes about 17 mm-about 18 mm, follicle sizes about 19 mm about 20 mm, and measurements of estradiol may be the six most statistically significant variables that may be predictive of the egg outcome for a patient. These six most statistically significant variables may closely track the egg outcome for the patient. For example, a trigger day selection model may be implemented to determine a trigger day based on these six most statistically significant variables. For instance, the trigger day may be selected based on the follicle size measurements and the measurement of estradiol for the patient. FIG. 14C illustrates a validation of the predicted egg outcome vs. the actual egg outcome when the six most statistically significant variables are measured on the trigger day for the patient.

Figure 14D:
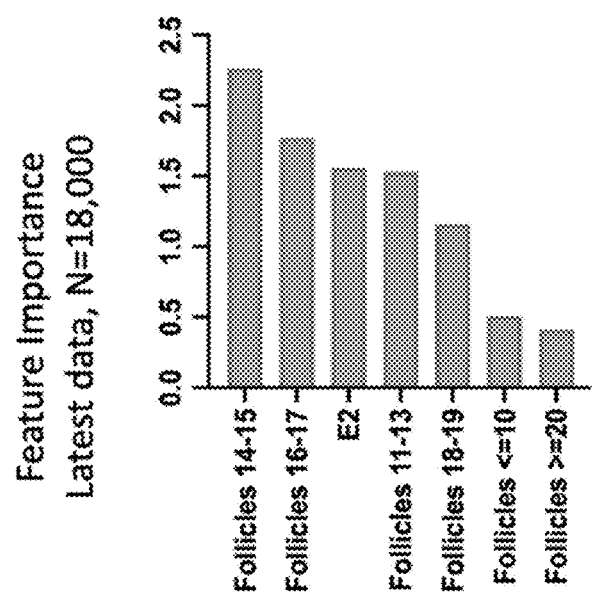
FIG. 14D illustrates another example of statistically significant variables that may be predictive of the egg outcome for a patient.

However, as described above, it should be understood that in other suitable variations, different kinds of suitable regression model parameters may exist. FIG. 14D relates to another example in which seven variables are particularly predictive of the egg outcome for a patient. Specifically, as shown in FIG. 14D, follicle sizes less than or equal to about 10 mm, follicle sizes about 11 mm-about 13 mm, follicle sizes about 14 mm-about 15 mm, follicle sizes about 16 mm-about 17 mm, follicle sizes about 18 mm-about 19 mm, follicle sizes greater than or equal to about 20 mm, and measurements of estradiol may be seven statistically significant variables that may be predictive of the egg outcome for a patient.

Figure 15A:
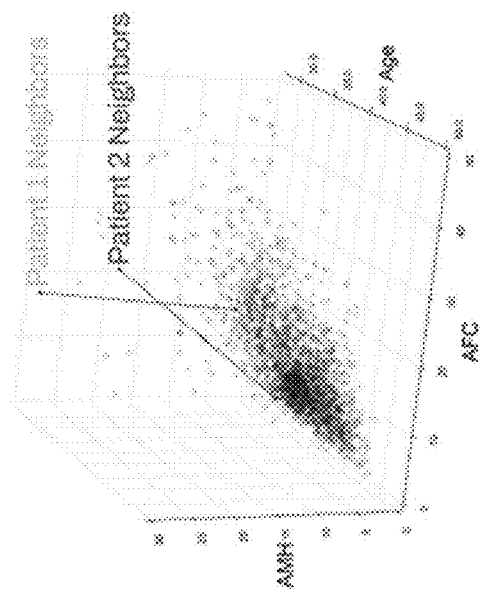
FIGS. 15A-15C illustrate an example of a similarity model described herein being implemented to determine whether a patient is an FSH dose-responsive patient or an FSH dose non-responsive patient.
Figure 15B:
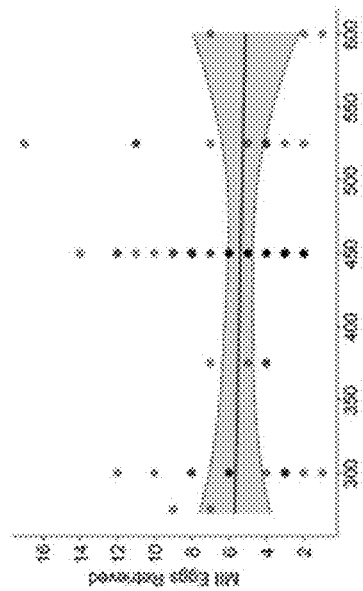
Figure 15C:
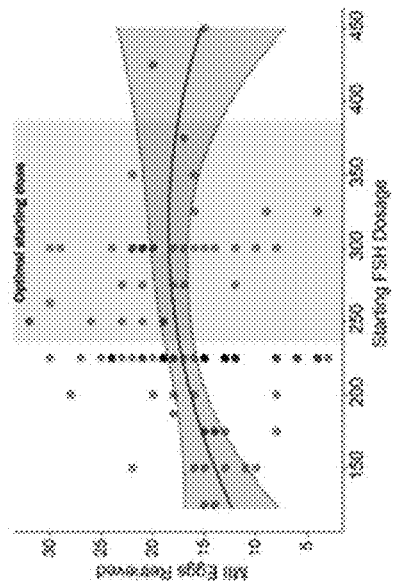

FIGS. 15A-15C illustrate an example of a similarity model being implemented to determine whether a patient is an FSH dose-responsive patient or an FSH dose non-responsive patient. In this example, the data for training/generating a regression model was collected from 4 different IVF clinics. The data was filtered for autologous non-canceled IVF retrievals. This included 7977 cycles between 2014-2020.

A KNN patient similarity model as discussed above was generated based on this data. As seen in FIG. 15A, the KNN model was used to identify 100 similar patients for patient 1 and 100 similar patients for patient 2 based on parameters such as BMI, age, baseline AMH, and baseline AFC. The 100 similar patients were used to create a dose response curve that predicts the number of eggs retrieved for various starting FSH doses. For example, the dose response curve for patient 1 is shown in FIG. 15B and the dose response curve for patient 2 is shown in FIG. 15C. The dose response curve for each of patient 1 and patient 2 were analyzed to determine whether the patients are FSH dose-responsive or FSH dose non-responsive. For example, in FIG. 15B, the number of eggs retrieved increases with an increase in FSH dosage indicating that patient 1 is dose responsive. However, in FIG. 15C, the number of eggs retrieved remains unchanged with an increase in FSH dosage indicating that patient 2 is dose non-responsive.

In some variations, as discussed above, one or more models described herein may be implemented to predict a trigger day for a patient so as to maximize egg outcome. The benefit of using the models described herein may be calculated by analyzing each patient on a regular basis (e.g., on a day-by-day basis, such as every day during administration of a stimulation protocol or every day during a subset of days of administration of a stimulation protocol). More specifically, quality of the models described herein may be estimated based on data obtained from each patient.

In some variations, the models described herein may be used to predict a trigger selection day. For example, the model may recommend continuing a stimulation protocol for a patient if the predicted egg outcome shows a two-day increase. For instance, if the egg outcome is predicted to increase from day 5 to day 7, the model may recommend continuing the stimulation protocol for the patient at least until day 7. Similarly, the model may recommend continuing a stimulation protocol for a patient if the predicted egg outcome is less than 15 (e.g., number of eggs predicted to be retrieved is less than 15) or if the amount of predicted estradiol is less than 5000. However, if the egg outcome is predicted to show a two-day decrease, the model may recommend triggering the ovarian stimulation to extract eggs. Additionally or alternatively, the predicted trigger selection day may be compared to the actual trigger day to determine whether the actual trigger is early or late. In some variations, the model may also make a recommendation of continuing or stopping a stimulation protocol based on a 1-day increase or decrease.

One or more models described herein may be used to predict a trigger day for a patient so as to maximize egg outcome. For example, estradiol and follicle sizes may be used to predict number of mature eggs. On each day of measurements during a stimulation protocol, the model may predict the egg outcome (e.g., number of mature eggs) if that day is a trigger day, forecast the estradiol and follicle sizes for the next day, and additionally predict the egg outcome if the next day is a trigger day. Such a model may be used throughout a stimulation protocol in order to guide whether to continue stimulation or trigger ovulation and reduce the likelihood of triggering ovulation either too late or too early, as described below with respect to FIGS. 16A-16D and 17A-17D.

Figure 16A:
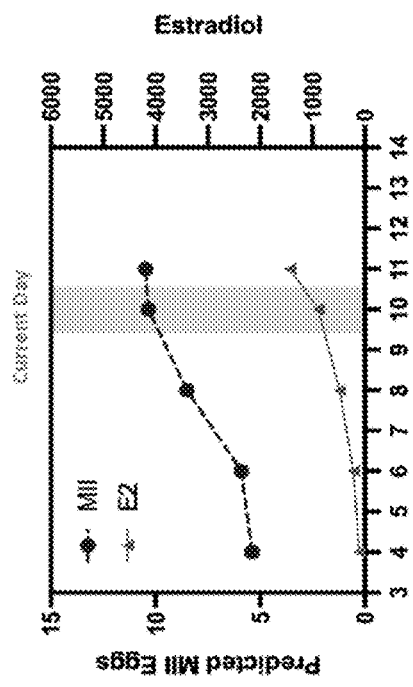
FIGS. 16A-16D illustrate an example of implementing one or more models described herein to predict a trigger day for a patient so as to maximize egg outcome.
Figure 16B:
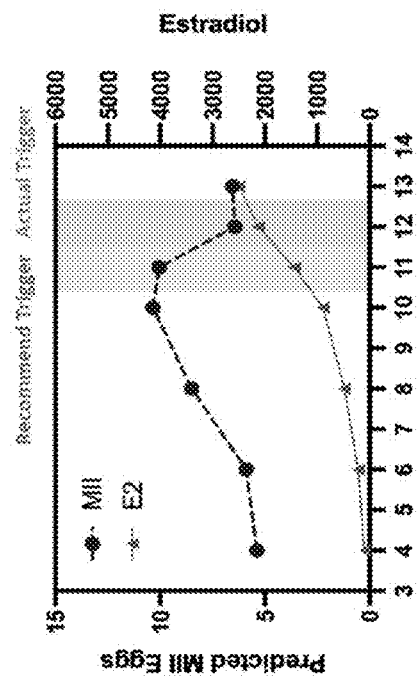
Figure 16C:
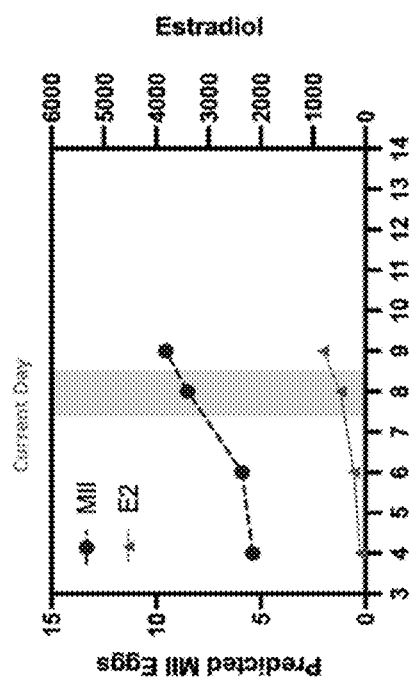
Figure 16D:
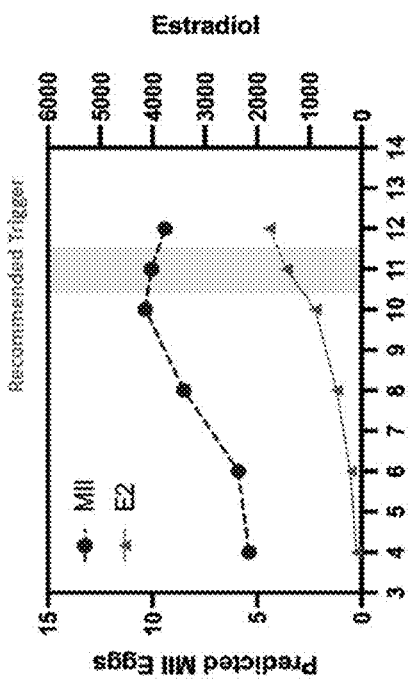

FIGS. 16A-16D illustrate an example of applying such a model to an example patient undergoing ovarian stimulation, where the circular dots represent the predicted egg outcome and the triangular symbols represent the amount of estradiol (for simplicity, follicle sizes are not shown). The dashed lines depict a prediction by the model. Estradiol and follicle measurements for this patient begin on day 4 of stimulation. As shown in FIG. 16A, on day 8 of stimulation, the model predicts the egg outcome if day 8 is the trigger day, forecasts the estradiol and follicle sizes for day 9, and predicts egg outcome if day 9 is the trigger day. Specifically, the model predicts that the egg outcome increases between day 8 and day 9, so based on this model the recommendation is to continue the stimulation protocol. Accordingly, the stimulation protocol continues through day 10 for this patient, and as shown in FIG. 16B, on day 10, the model predicts that the egg outcome will remain about the same between days 10 and 11. As shown in FIG. 16C, on day 11, the model predicts a clear decline in egg outcome for day 12 relative to that for day 11. Since this future decrease in egg outcome is predicted, the recommendation on day 11 is that day 11 should be the trigger day. If the trigger day is not selected to be day 11 and instead stimulation continues until day 12 when trigger occurs, then the actual trigger on day 12 is possibly late, as shown in FIG. 16D, thereby resulting in an undesirably reduced egg outcome.

FIGS. 17A-17C illustrate another example of implementing one or more models described herein to predict a trigger day for a patient so as to maximize egg outcome, where the circular dots represent the predicted egg outcome and the triangular symbols represent the amount of estradiol. The dashed lines depict a prediction by the model. As shown in FIG. 17A, on day 7 of stimulation, the model predicts the egg outcome if day 7 is the trigger day, forecasts the estradiol and follicle sizes for day 8, and predicts egg outcome if day 8 is the trigger day. Specifically, the model predicts that the egg outcome increases between days 7 and 8, so based on this model the recommendation is to continue the stimulation protocol. Accordingly, the stimulation protocol continues through day 9 for this patient, and as shown in FIG. 17B, on day 9, the model predicts that the egg outcome will continue to increase between days 9 and 10. As shown in FIG. 17C, on day 10, the model predicts that egg outcome will increase even further between days 10 and 11, so the recommendation is to continue the stimulation protocol and further delay the trigger. As such, if a RE selects day 10 as a trigger day, then this actual trigger on day 10 is possibly early, thereby resulting in an undesirably reduced egg outcome.

ENUMERATED EMBODIMENTS

Embodiment A1. A computer-implemented method for optimizing an ovarian stimulation process, the method comprising:
receiving patient-specific data associated with a patient; and
predicting an egg outcome for the patient for each of a plurality of treatment options for an ovarian stimulation process based on at least one predictive model and the patient-specific data, wherein the at least one predictive model is trained using prior patient-specific data associated with a plurality of prior patients.

Embodiment A2. The method of embodiment A1, further comprising providing the predicted egg outcome to a medical professional for selecting among the plurality of treatment options.

Embodiment A3. The method of embodiment A1, wherein the predicted egg outcome comprises at least one of number of eggs retrieved and number of mature eggs.

Embodiment A4. The method of embodiment A1, wherein the predicted egg outcome comprises at least one of maturity yield, number of post-mature eggs, number of fertilized eggs, number of embryos, number of blastocysts, number of usable blastocysts, number of euploid blastocysts, fetal heartbeat, and live birth rates.

Embodiment A5. The method of embodiment A1, wherein the patient-specific data comprises at least one of age, body mass index, ethnicity, diagnosis of infertility, prior pregnancy history, prior birth history, and one or more baseline measurements selected from the group consisting of: measurements of estradiol (E2), measurements of luteinizing hormone (LH), measurements of progesterone (P4), measurements of follicle stimulating hormone (FSH), measurements of anti-mullerian hormone (AMH), and measurements of antral follicle count (AFC).

Embodiment A6. The method of embodiment A1, wherein the patient-specific data comprises information relating to one or more prior in vitro fertilization (IVF) treatments associated with the patient.

Embodiment A7. The method of embodiment A6, wherein the information relating to one or more prior IVF treatments comprises at least one of data retrieved during ovarian stimulation, number of eggs retrieved, number of mature eggs, number of successfully fertilized eggs, pregnancy outcome, and live birth outcome.

Embodiment A8. The method of embodiment A1, wherein the patient-specific data comprises one or more treatment variables associated with the patient.

Embodiment A9. The method of embodiment A8, wherein the one or more treatment variables comprises a type of medication, a type of hormonal trigger injection to cause follicle maturation, and number of cycle(s) associated with the patient.

Embodiment A10. The method of embodiment A1, wherein the at least one predictive model is configured to provide the predicted egg outcome associated with each of a plurality of candidate doses of one or more ovarian stimulation medications administered to the patient.

Embodiment A11. The method of embodiment A10, wherein the one or more ovarian stimulation medications comprises follicle stimulating hormone (FSH).

Embodiment A12. The method of embodiment A10, wherein the one or more ovarian stimulation medications comprises luteinizing hormone (LH).

Embodiment A13. The method of embodiment A10, wherein the patient-specific data comprises one or more baseline measurements selected from the group consisting of: measurements of estradiol (E2), measurements of luteinizing hormone (LH), measurements of progesterone (P4), measurements of follicle stimulating hormone (FSH), measurements of anti-mullerian hormone (AMH), and measurements of antral follicle count (AFC).

Embodiment A14. The method of embodiment A10, wherein the at least one predictive model is configured to provide the predicted egg outcome associated with each of a first dose and a second dose, wherein the second dose is greater than the first dose.

Embodiment A15. The method of embodiment A10, wherein the at least one predictive model is configured to provide the predicted egg outcome associated with each of a first dose ratio of multiple ovarian stimulation medications and a second dose ratio of multiple ovarian stimulation medications, wherein the first dose ratio is different than the second dose ratio.

Embodiment A16. The method of embodiment A10, further comprising:

identifying a set of prior patients similar to the patient based on the patient-specific data via a similarity matching technique, wherein the at least one predictive model comprises a predictive dose response curve generated based on the prior patient-specific data associated with the prior patients, wherein the dose response curve predicts the egg outcome varying with dose of one or more ovarian stimulation medications administered to the patient.

Embodiment A17. The method of embodiment A16, wherein the similarity matching technique comprises a KNN model.

Embodiment A18. The method of embodiment A16, further comprising classifying the patient as one of: (i) a dose-responsive patient having predicted egg outcomes that substantially vary with the dose of one or more ovarian stimulation medications administered to the patient, and (ii) a dose non-responsive patient having predicted egg outcomes that do not substantially vary with dose of one or more ovarian stimulation medications administered to the patient, wherein the classification is based at least in part on a shape of the dose response curve.

Embodiment A19. The method of embodiment A18, further comprising, when the patient is classified as a dose-responsive patient, recommending an optimal dose of the one or more ovarian stimulation medications to be administered to the patient, based on a point of the dose response curve associated with a predicted maximum egg outcome.

Embodiment A20. The method of embodiment A16, further comprising displaying the predictive dose response curve on a display.

Embodiment A21. The method of embodiment A1, wherein the at least one predictive model comprises a first predictive model and a second predictive model, the method further comprising:

predicting, via the first predictive model, a first egg outcome resulting from administering a hormonal trigger injection on a first candidate hormonal trigger day;

predicting, via the second predictive model, a second egg outcome resulting from administering the hormonal trigger injection on a second candidate hormonal trigger day, wherein the hormonal trigger injection is configured to cause follicle maturation in the patient.

Embodiment A22. The method of embodiment A21, wherein the first day is a current day and the second day is a future day.

Embodiment A23. The method of embodiment A21, wherein the patient-specific data comprises a current day follicle metric.

Embodiment A24. The method of embodiment A21, wherein the patient-specific data comprises a current day estradiol (E2) level for the patient.

Embodiment A25. The method of embodiment A21, wherein the patient-specific data further comprises a current day progesterone (P4) level for the patient.

Embodiment A26. The method of embodiment A21, wherein the first and second predicted egg outcomes comprise at least one of number of eggs retrieved, number of mature eggs, number of fertilized eggs, and number of usable blastocysts.

Embodiment A27. The method of embodiment A21, wherein at least one of the first and second predictive models comprises a recurrent neural network or a generalized linear model.

Embodiment A28. The method of embodiment A27, wherein at least one of the first and second predictive models comprises a generalized linear model selected from the group consisting of a linear regression model, a Poisson regression model, and a negative binomial regression model.

Embodiment A29. The method of embodiment A28, wherein each of the first and second predictive models comprises a linear regression model.

Embodiment A30. The method of embodiment A27, wherein at least one of the first and second predictive models is configured to forecast E2 measurements for the patient at a future date.

Embodiment A31. The method of embodiment A27, wherein at least one of the first and second predictive models is configured to forecast a follicle metric for the patient at a future date.

Embodiment A32. The method of embodiment A27, wherein at least one of the first and second predictive models is configured to predict the first or second egg outcome based at least in part on at least one of the E2 measurement and a follicle metric.

Embodiment A33. The method of embodiment A21, further comprising displaying the first and second egg outcomes on a display.

Embodiment B1. A computer-implemented method for optimizing an ovarian stimulation process, the method comprising:

receiving patient-specific data associated with a patient;

identifying a set of prior patients similar to the patient based on the patient-specific data via a similarity matching technique; and generating a predictive dose response curve based on prior patient-specific data associated with the prior patients, wherein the dose response curve predicts egg outcome varying with dose of one or more ovarian stimulation medications administered to the patient.

Embodiment B2. The method of embodiment B1, wherein the one or more ovarian stimulation medications comprises follicle stimulating hormone (FSH).

Embodiment B3. The method of embodiment B2, wherein the dose responsive curve predicts egg outcome varying with starting dose of FSH.

Embodiment B4. The method of embodiment B1, wherein the one or more ovarian stimulation medications comprises luteinizing hormone (LH).

Embodiment B5. The method of embodiment B1, wherein the patient-specific data comprises one or more baseline measurements selected from the group consisting of: measurements of estradiol (E2), measurements of luteinizing hormone (LH), measurements of progesterone (P4), measurements of follicle stimulating hormone (FSH), measurements of anti-mullerian hormone (AMH), and measurements of antral follicle count (AFC).

Embodiment B6. The method of embodiment B1, wherein the predictive dose response curve is configured to provide the predicted egg outcome associated with each of a first dose and a second dose, wherein the second dose is greater than the first dose.

Embodiment B7. The method of embodiment B1, wherein the predictive dose response curve is configured to provide the predicted egg outcome associated with each of a first dose ratio of multiple ovarian stimulation medications and a second dose ratio of multiple ovarian stimulation medications, wherein the first dose ratio is different than the second dose ratio.

Embodiment B8. The method of embodiment B1, wherein the similarity matching technique comprises a KNN model.

Embodiment B9. The method of embodiment B1, further comprising classifying the patient as one of: (i) a dose-responsive patient having predicted egg outcomes that substantially vary with the dose of one or more ovarian stimulation medications administered to the patient, and (ii) a dose non-responsive patient having predicted egg outcomes that do not substantially vary with dose of one or more ovarian stimulation medications administered to the patient, wherein the classification is based at least in part on a shape of the dose response curve.

Embodiment B10. The method of embodiment B9, further comprising, when the patient is classified as a dose-responsive patient, recommending an optimal dose of the one or more ovarian stimulation medications to be administered to the patient, based on a point of the dose response curve associated with a predicted maximum egg outcome.

Embodiment B11. The method of embodiment B1, further comprising displaying the dose response curve on a display.

Embodiment B12. The method of embodiment B11, further comprising displaying a confidence interval around the dose response curve.

Embodiment B13. The method of embodiment B11, further comprising displaying a cost estimate for administering different doses of one or more ovarian stimulation medications in accordance with the dose response curve.

Embodiment C1. A computer-implemented method for optimizing an ovarian stimulation process, the method comprising:

receiving patient-specific data associated with a patient;

predicting, via a first predictive model, a first egg outcome resulting from administering a hormonal trigger injection on a first candidate hormonal trigger day;

predicting, via a second predictive model, a second egg outcome resulting from administering the hormonal trigger injection on a second candidate hormonal trigger day, wherein the hormonal trigger injection is configured to cause follicle maturation in the patient.

Embodiment C2. The method of embodiment C1, wherein the first day is a current day and the second day is a future day.

Embodiment C3. The method of embodiment C2, wherein the first day and the second day are consecutive days.

Embodiment C4. The method of embodiment C1, wherein the patient-specific data comprises a current day follicle metric.

Embodiment C5. The method of embodiment C1, wherein the patient-specific data comprises a current day estradiol (E2) level for the patient.

Embodiment C6. The method of embodiment C4, wherein the patient-specific data further comprises current day progesterone (P4) for the patient.

Embodiment C7. The method of embodiment C1, wherein the first and second predicted egg outcomes comprise at least one of number of eggs retrieved, number of mature eggs, number of fertilized eggs, and number of usable blastocysts.

Embodiment C8. The method of embodiment C1, wherein at least one of the first and second predictive models comprises a recurrent neural network or a generalized linear model.

Embodiment C9. The method of embodiment C8, wherein at least one of the first and second predictive models comprises a generalized linear model selected from the group consisting of a linear regression model, a Poisson regression model, and a negative binomial regression model.

Embodiment C10. The method of embodiment C8, wherein each of the first and second predictive models comprises a linear regression model.

Embodiment C11. The method of embodiment C8, wherein at least one of the first and second predictive models is configured to forecast E2 measurements for the patient at a future date.

Embodiment C12. The method of embodiment C8, wherein at least one of the first and second predictive models is configured to forecast a follicle metric measurement for the patient at a future date.

Embodiment C13. The method of embodiment C8, wherein at least one of the first and second predictive models is configured to predict the first or second egg outcome based at least in part on at least one of an E2 measurement and a follicle metric.

Embodiment C14. The method of embodiment C1, further comprising providing the first and second predicted egg outcomes to a medical professional for selecting between the first and second candidate hormonal trigger days.

Embodiment C15. The method of embodiment C14, wherein providing the first and second predicted egg outcomes comprises displaying the first and second egg outcomes on a display.

Embodiment D1. A computer-implemented method comprising:

receiving patient-specific data associated with a patient; and predicting at least one egg outcome for the patient based on at least one predictive model and the patient-specific data, wherein the patient-specific data comprise a follicle size classified into a bin from a plurality of predetermined bins, wherein each bin of the plurality of predetermined bins is associated with a respective range of follicle sizes, wherein the at least one predictive model is trained using prior patient-specific data associated with a plurality of prior patients.

Embodiment D2. The method of embodiment D1, wherein at least one bin of the plurality of bins is associated with a first follicle size range of about 10 mm or less, a second follicle size range of about 11 mm-13 mm, a third follicle size range of about 14 mm-15 mm, a fourth follicle size range of about 16 mm-17 mm, a fifth follicle size range of about 18 mm-19 mm, a sixth follicle size range of greater than about 20 mm.

Embodiment D3. The method of embodiment D2, wherein the plurality of bins comprises six bins, wherein each bin is associated with a respective one of the first follicle size range, second follicle size range, third follicle size range, fourth follicle size range, fifth follicle size range, and sixth follicle size range.

Embodiment D4. The method of embodiment D1, wherein the patient-specific data comprises an E2 level for the patient, and wherein predicting at least one egg outcome comprises predicting at least one egg outcome based on the E2 level.

Embodiment D5. The method of embodiment D1, further comprising displaying the predicted egg outcome on a display.

Embodiment E1. A computer-implemented method comprising:
  receiving patient-specific data associated with a patient;
  predicting an egg outcome for the patient for each of a plurality of days based on at least one predictive model and patient-specific data, wherein the at least one predictive model is trained using prior patient-specific data associated with a plurality of prior patients; and
  displaying a trend of the predicted egg outcomes for the plurality of days on a display.

Embodiment E2. The method of embodiment E1, wherein the predicted egg outcome comprises at least one of number of eggs retrieved and number of mature eggs.

Embodiment E3. The method of embodiment E1, wherein the predicted egg outcome comprises at least one of maturity yield, number of post-mature eggs, number of fertilized eggs, number of embryos, number of blastocysts, number of usable blastocysts, number of euploid blastocysts, fetal heartbeat, and live birth rate.

Embodiment F1. A method of treatment comprising:
  providing patient-specific data associated with a patient;
  receiving a predicted egg outcome associated with each of a plurality of treatment options, wherein at least one predicted egg outcome is generated with at least one predictive model in accordance with the method of any one of embodiments A1-A33, B1-B13, C1-C15, D1-D5, and E1-E3;
  selecting a treatment option based on the predicted egg outcomes; and
  administering an ovarian stimulation medication in accordance with the selected treatment option.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A method for optimizing an ovarian stimulation process, the method comprising:
  predicting, by a processor, a first egg outcome for a first candidate hormonal trigger day and a second egg outcome for a second candidate hormonal trigger day for a patient based on one or more predictive models having received data associated with the patient, wherein the one or more predictive models are trained using data associated with a plurality of prior patients and provide the first and second predicted egg outcomes, and wherein each of the first and the second predicted egg outcomes comprises one or more of: number of eggs retrieved, number of mature eggs, maturity yield, number of post-mature eggs, number of fertilized eggs, number of embryos, number of blastocysts, number of usable blastocysts, and number of euploid blastocysts; and
  administering a hormonal trigger injection configured to cause follicle maturation in the patient on the first candidate hormonal trigger day or on the second candidate hormonal trigger day based on the first and the second predicted egg outcomes.

2. The method of claim 1, wherein the first and second predicted egg outcomes each comprise at least one of the number of eggs retrieved and the number of mature eggs.

3. The method of claim 1, wherein the data associated with the patient comprises at least one of age, body mass index, ethnicity, diagnosis of infertility, prior pregnancy history, prior birth history, and one or more baseline measurements selected from the group consisting of: measurements of estradiol (E2), measurements of luteinizing hormone (LH), measurements of progesterone (P4), measurements of follicle stimulating hormone (FSH), measurements of anti-mullerian hormone (AMH), and measurements of antral follicle count (AFC).

4. The method of claim 1, wherein the data associated with the patient comprises information relating to one or more prior in vitro fertilization (IVF) treatments associated with the patient.

5. The method of claim 4, wherein the information relating to one or more prior IVF treatments comprises at least one of data retrieved during ovarian stimulation, number of eggs retrieved, number of mature eggs, number of successfully fertilized eggs, number of blastocysts, number of usable blastocysts, pregnancy outcome, and live birth outcome.

6. The method of claim 1, wherein the data associated with the patient comprises one or more treatment variables associated with the patient.

7. The method of claim 6, wherein the one or more treatment variables comprises a type of medication, a type of hormonal trigger injection to cause follicle maturation, and number of cycle(s) associated with the patient.

8. The method of claim 1 further comprising, providing a predictive dose response curve showing a predicted egg outcome varying with each of a plurality of candidate doses of one or more ovarian stimulation medications for the patient.

9. The method of claim 8, wherein the one or more ovarian stimulation medications comprises follicle stimulating hormone (FSH).

10. The method of claim 8, wherein the one or more ovarian stimulation medications comprises luteinizing hormone (LH).

11. The method of claim 8, wherein the data associated with the patient comprises one or more baseline measurements selected from the group consisting of: measurements of estradiol (E2), measurements of luteinizing hormone (LH), measurements of progesterone (P4), measurements of follicle stimulating hormone (FSH), measurements of anti-mullerian hormone (AMH), and measurements of antral follicle count (AFC).

12. The method of claim 8, wherein the plurality of candidate doses of the one or more ovarian stimulation medications comprises a first candidate dose and a second candidate dose, and, wherein the second candidate dose is greater than the first candidate dose.

13. The method of claim 8, wherein the plurality of candidate doses of the one or more ovarian stimulation medications comprises a first candidate dose ratio of multiple ovarian stimulation medications and a second candidate dose ratio of multiple ovarian stimulation medications, and wherein the first dose ratio is different than the second dose ratio.

14. The method of claim 8, further comprising:
identifying a set of prior patients similar to the patient based on the data associated with the patient via a similarity matching technique,
wherein the predictive dose response curve is generated based on the data associated with the set of prior patients similar to the patient.

15. The method of claim 14, further comprising classifying the patient as one of: (i) a dose-responsive patient having predicted egg outcomes that substantially vary with the plurality of candidate doses of the one or more ovarian stimulation medications for the patient, and (ii) a dose non-responsive patient having predicted egg outcomes that do not substantially vary with the plurality of candidate doses of the one or more ovarian stimulation medications for the patient, wherein the classification is based at least in part on a shape of the predictive dose response curve.

16. The method of claim 15, further comprising, when the patient is classified as a dose-responsive patient, recommending an optimal dose of the one or more ovarian stimulation medications to be administered to the patient, based on a point of the predictive dose response curve associated with a predicted maximum egg outcome.

17. The method of claim 14, wherein the similarity matching technique comprises a K-nearest neighbors technique.

18. The method of claim 1, wherein the one or more predictive models comprise a first predictive model and a second predictive model, the method further comprising: predicting the first predicted egg outcome via the first predictive model; and predicting the second predicted egg outcome via the second predictive model.

19. The method of claim 18, wherein each of the first and second predictive models comprises a generalized linear model selected from the group consisting of a linear regression model, a Poisson regression model, and a negative binomial regression model.

20. The method of claim 19, wherein at least one of the first and second predictive models is configured to predict the first or second predicted egg outcome based at least in part on at least one of an E2 level and a follicle metric.

21. The method of claim 1, wherein the first candidate hormonal trigger day is a current day and the second candidate hormonal trigger day is a future day.

22. The method of claim 21, wherein the data associated with the patient comprises a current day follicle metric for the patient.

23. The method of claim 21, wherein the data associated with the patient comprises a current day estradiol (E2) level for the patient.

24. The method of claim 21, wherein the data associated with the patient comprises a current day progesterone (P4) level for the patient.

25. The method of claim 21, wherein the first and second predicted egg outcomes each comprise at least one of the number of eggs retrieved, the number of mature eggs, the number of fertilized eggs, and the number of usable blastocysts.

26. The method of claim 1, wherein the one or more predictive models further provide a forecasted E2 level for the patient at a future date.

27. The method of claim 1, wherein the one or more predictive models further provide a forecasted follicle metric for the patient at a future date.

28. The method of claim 1, further comprising, training the one or more predictive models with the data associated with the plurality of prior patients.

29. The method of claim 1, wherein one or more of the data associated with the patient and the data associated with the plurality of prior patients is received from an electronic medical record database.

30. The method of claim 1, further comprising, transmitting a signal indicative of the first and second predicted egg outcomes to a display for visual representation.

* * * * *